(12) United States Patent
Thuring et al.

(10) Patent No.: US 8,716,293 B2
(45) Date of Patent: May 6, 2014

(54) MACROCYCLIC INTEGRASE INHIBITORS

(75) Inventors: Johannes Wilhelmus J. Thuring, Beerse (BE); Jean-Francois Bonfanti, Ande (FR)

(73) Assignee: Janssen R&D Ireland, Little Island, Co Cork (IE)

( * ) Notice: Subject to any disclaimer, the term of this patent is extended or adjusted under 35 U.S.C. 154(b) by 0 days.

(21) Appl. No.: 13/637,557

(22) PCT Filed: Apr. 1, 2011

(86) PCT No.: PCT/EP2011/055077
§ 371 (c)(1),
(2), (4) Date: Sep. 26, 2012

(87) PCT Pub. No.: WO2011/121105
PCT Pub. Date: Oct. 6, 2011

(65) Prior Publication Data
US 2013/0035341 A1    Feb. 7, 2013

(30) Foreign Application Priority Data
Apr. 2, 2010 (EP) .................... 10159060

(51) Int. Cl.
C07D 487/18 (2006.01)
C07D 498/18 (2006.01)
C07D 515/18 (2006.01)
A61K 31/529 (2006.01)
A61P 31/18 (2006.01)

(52) U.S. Cl.
USPC ............ 514/250; 540/457; 540/472; 540/477

(58) Field of Classification Search
USPC ........................... 540/457, 472, 477; 514/250
See application file for complete search history.

(56) References Cited

U.S. PATENT DOCUMENTS

| 2005/0239819 A1 | 10/2005 | Satoh et al. |
| 2008/0207618 A1 | 8/2008 | Satoh et al. |

FOREIGN PATENT DOCUMENTS

| EP | 1874117 A1 | 1/2008 |
| WO | WO 02/20930 A2 | 4/2002 |
| WO | WO 02/30426 A1 | 4/2002 |
| WO | WO 02/30931 A2 | 4/2002 |
| WO | WO 02/36734 A2 | 5/2002 |
| WO | WO 02/055079 A2 | 7/2002 |
| WO | WO 2004/035577 A2 | 4/2004 |
| WO | WO 2004/046115 A1 | 6/2004 |
| WO | WO 2004/058757 A1 | 7/2004 |
| WO | WO 2004/103278 A2 | 12/2004 |
| WO | WO 2005/028478 A1 | 3/2005 |
| WO | WO 2005/041664 A1 | 5/2005 |
| WO | WO 2005/087766 A1 | 9/2005 |
| WO | WO 2005/110414 A2 | 11/2005 |
| WO | WO 2005/110415 A1 | 11/2005 |
| WO | WO 2005/118593 A1 | 12/2005 |
| WO | WO 2006/116764 A1 | 11/2006 |

OTHER PUBLICATIONS

Singh, S.B., et al., "The Complestatins as HIV-1 Integrase Inhibitors, Efficient Isolation, Structure Elucidation, and Inhibitory Activities of Isocomplestatin, Chloropeptin I, New Complestatins, A and B, and Acid-Hydrolysis Products of Chloropeptin I", Journal of Natural Products, American Chemical Society (2001), vol. 64, No. 7, pp. 874-882.
Wai, J., et al., "Next Generation of Inhibitors of HIV01 Integrase Strand Transfer Inhibitor: Structural Diversity and Resistance Profiles", http://retroconference.org/2007/Abstracts/29783.htm CROI (2007) Abstract #87, Session 26, Oral Abstracts.
Vacca, J.P., et al., "Discovery of MK-2048: Subtle Changes Confer Unique Resistance Properties to a Series of Tricyclic Hydroxypyrrole Integrase Strand Transfer Inhibitors", http://www.iasociety.org/Abstracts/A200703234.aspx (2007) International AIDS Society—Abstract-200703234.
Johnson, V.A., et al., "Topics in HIV Medicine—Update of the Drug Resistance Mutations in HIV-1: Dec. 2009", International AIDS Society—USA, (2009), vol. 17, No. 5 pp. 138-145.
Fields, R.D., et al., "Dual-Attribute Continuous Monitoring of Cell Proliferation/Cytotoxicity", American Biotechnology Laboratory, (1993), vol. 11, pp. 48-50.
International Search report for Application No. PCT/EP2011/055077 mailed Apr. 1, 2011.

*Primary Examiner* — Bruck Kifle
(74) *Attorney, Agent, or Firm* — Michael J. Atkins

(57) ABSTRACT

Compound having formula I

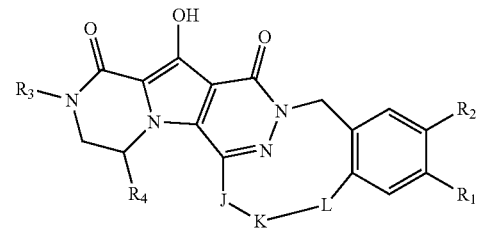

and pharmaceutically acceptable salts or solvates thereof, their pharmaceutical formulations and use as HIV inhibitors.

17 Claims, No Drawings

MACROCYCLIC INTEGRASE INHIBITORS

CROSS REFERENCE TO RELATED APPLICATIONS

This application is a national stage of PCT Application No. PCT/EP2011/055077, filed Apr. 1, 2011, which claims priority from European Patent Application No. 10159060.2, filed Apr. 2, 2010, all of which are hereby incorporated by reference in their entirety.

This invention concerns macrocyclic pyrazinopyrrolopyridazine dione derivatives having HIV (Human Immunodeficiency Virus) replication inhibiting properties, the preparation thereof and pharmaceutical compositions comprising these compounds.

BACKGROUND

Initially, treatment of HIV infection consisted of monotherapy with nucleoside derivatives and although successful in suppressing viral replication, these drugs quickly lost their effectiveness due to the emergence of drug-resistant strains. It became clear that a high mutation rate combined with rapid replication made HIV a particularly challenging target for antiviral therapy. The introduction of combination therapy of several anti-HIV agents improved therapeutic outcome. The current standard of care is the so-called HAART (Highly Active Anti-Retroviral Therapy), which offers a powerful and sustained viral suppression. HAART typically involves a combination of nucleoside or nucleotide reverse transcriptase inhibitors (NRTIs or NtRTIs respectively) with a non-nucleoside reverse transcriptase inhibitor (NNRTI), a protease inhibitor (PI), and an integrase inhibitor or entry inhibitor. Current guidelines for antiretroviral therapy recommend at least a triple combination therapy regimen even for initial treatment. Although HAART is capable of suppressing HIV up to undetectable levels, resistance can emerge due to compliance problems. It also has been shown that resistant virus is carried over to newly infected individuals, resulting in severely limited therapy options for these drug-naive patients.

Therefore there is a continued need for new and effective compounds that can be used as anti-HIV drugs. In particular, there is need for further HIV integrase inhibitors that are more effective in terms of activity against wild type virus, but also against mutated strains, in particular toward mutated strains selected by known integrase inhibitors such as raltegravir and elvitegravir. Primary mutations most frequently developed during raltegravir therapy include N155H and Q148K/R/H, and infrequently Y143R/C. The acquisition of N155 or Q148 mutations was found to result in cross-resistance to structurally diverse integrase inhibitors. Raltegravir treatment failure is associated with integrase mutations in at least 3 distinct genetic pathways defined by 2 or more mutations including a signature (major) mutation being one of the primary mutations at Q148H/K/R, N155H, or Y143R/H/C, and, one or more additional minor mutations. Minor mutations described in the Q148H/K/R pathway include L74M plus E138A, E138K, or G140S. The most common mutational pattern in this pathway is Q148H plus G140S, which also confers the greatest loss of drug susceptibility. (V. A. Johnson et al. (2009) Topics in HIV Medicine 17(5), 138-145).

There is a need for integrase inhibitors that offer advantages in terms of their pharmacokinetic and/or pharmacodynamic profile. Other aspects that should be considered in the development of further integrase inhibitors include a favorable safety profile, dosing and/or the lack of the need for boosting.

Other HIV integrase inhibitors are known in the art. For instance, WO255079, WO0230931, WO0230930 and WO0230426 disclose aza- and polyaza-naphthalenyl carboxamides useful as inhibitors of HIV integrase. WO0236734 discloses additionally aza- and polyaza-naphthalenyl ketones useful as inhibitors of HIV integrase. In Roggo et al., Journal of antibiotics (1996), spirodihydrobenzofuranlactams are disclosed as antagonists of endothelin and as inhibitors of HIV-1 protease.

Polycyclic carbamoylpyridones have also been disclosed as inhibitors of HIV integrase in EP1874117. WO2005118593 discloses a series of bicyclic heterocycles as integrase inhibitors, and WO2004103278 discloses a series of acyl sulfonamides as inhibitors of HIV integrase. WO2005028478 discloses a series of aza-quiniolinol phosphonate compounds as integrase inhibitors and WO2004035577a series of pre-organised tricyclic integrase inhibitors. Furthermore, a series of pyridopyrazine and pyrimidopyrazine-dione compounds was disclosed WO2005087766. Additionally, tetrandyro-4H-pyrido (1,2-a) pyrimidines and related compounds were disclosed by Instituto di Ricerche di Biologia Moleculare p Angeletti Spa in WO2004058757. Japan Tobacco Inc have disclosed 4-oxyquinoline compounds as HIV integrase inhibitors in WO2004046115, and a 6-(heterocycle-substituted benzyl)-4-oxoquinoline compound as an HIV inhibitor in US20080207618. WO2005110414 and WO2005110415 disclose hydroxy-substituted pyrazinopyrrolopyridazine dione compounds as inhibitors of HIV integrase and inhibitors of HIV replication.

The present invention is aimed at providing a particular novel series of pyrazinopyrrolo-pyridazine dione derivatives having HIV replication- and HIV integrase-inhibiting properties.

DESCRIPTION OF THE INVENTION

Compounds of the invention differ from prior art compounds in structure, antiviral activity and/or pharmacological potency. It has been found that compounds of the invention not only are very active against wild type virus, but also against mutant strains, in particular against strains that display resistance to one or more known integrase inhibitors, which strains are referred to as drug- or multidrug-resistant HIV strains. It has also been found that compounds of the invention display favorable pharmacokinetic and/or pharmacodynamic properties.

Thus, in one aspect, the present invention concerns compounds of formula I, including the stereochemically isomeric forms thereof, which can be represented by formula I:

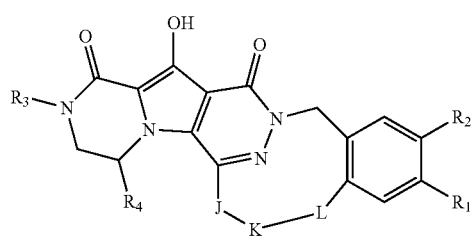

wherein,
$R_1$ is F or Cl;
$R_2$ is H, F or Cl;

$R_3$ is $C_{1-4}$alkyl, $C_{1-4}$alkoxy$C_{1-4}$alkyl, cyclopropyl or tetrahydrofuranyl;
$R_4$ is hydrogen or methyl;
J is —N($R_5$)—SO$_2$—, —C(=O)—N($R_5$)—, —N($R_5$)—,

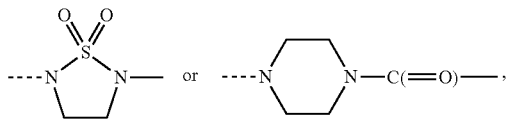

wherein the dashed line denotes the point of attachment to the pyridazinone ring;
K is —(CHR$_6$)$_p$—, *-(CH$_2$)$_q$—CH=CH—CH$_2$— or *-(CH$_2$)$_q$—C≡CH—CH$_2$— wherein * denotes to point of attachment to the J moiety;
L is —O—, —O—CH$_2$-* or —N($R_5$)—C(=O)-* wherein * denotes the point of attachment to the phenyl ring; and,
$R_5$ is hydrogen, $C_{1-4}$alkyl or $C_{3-5}$cycloalkyl;
each $R_6$ independently is hydrogen or $C_{1-3}$alkyl;
p is 3, 4, 5 or 6;
q is 0, 1, 2 or 3;
or a pharmaceutically acceptable salt or solvate thereof.

In a further aspect, the invention concerns the use of compounds of formula I, or subgroups thereof as specified herein, for inhibiting the replication cycle of HIV. Alternatively, there is provided the use of said compounds for the manufacture of a medicament for inhibiting the replication cycle of HIV, or, the compounds of formula I for use as medicament for inhibiting the replication of HIV.

As used herein, "$C_{1-3}$alkyl" as a group or part of a group defines saturated straight or branched chain hydrocarbon groups having from 1 to 3 carbon atoms such as for example methyl, ethyl, 1-propyl or 2-propyl.

As used herein, "$C_{1-4}$alkyl" as a group or part of a group defines saturated straight or branched chain hydrocarbon groups having from 1 to 4 carbon atoms such as for example methyl, ethyl, 1-propyl, 2-propyl, 1-butyl, 2-butyl, 2-methyl-1-propyl, 2-methyl-2-propyl.

The term "$C_{3-5}$cycloalkyl" is generic to cyclopropyl, cyclobutyl and cyclopentyl.

The term "$C_{1-4}$alkoxy" as a group or part of a group means a group of formula —O—$C_{1-4}$alkyl wherein $C_{1-4}$alkyl is as defined above. Examples of $C_{1-4}$alkoxy are methoxy, ethoxy, n-propoxy, isopropoxy, 1-butoxy, 2-butoxy and tert-butoxy.

Whenever a radical occurs in the definition of the compounds of formula I or in any of the subgroups specified herein, said radical independently is as specified above in the definition of the compounds of formulas I or in the more restricted definitions as specified hereinafter.

It should also be noted that the radical positions on any molecular moiety used in the definitions may be anywhere on such moiety as long as it is chemically stable. For instance butyl includes 1-butyl and 2-butyl.

Some of the compounds of formula I may also exist in their tautomeric form. Such forms although not explicitly indicated in the structural formulae disclosed herein are intended to be included within the scope of the present invention.

The present invention is also intended to include any isotopes of atoms present in the compounds of the invention. For example, isotopes of hydrogen include tritium and deuterium and isotopes of carbon include C-13 and C-14.

Whenever used hereinabove or hereinafter, the terms "compounds of formula I", "the present compounds", "the compounds of the present invention" or any equivalent terms, are meant to include the compounds of general formula I as well as their salts, solvates, and stereoisomers. Similarly, the terms "subgroups of compounds of formula I", "subgroups of the present compounds", "subgroups of the compounds of the present invention" or any equivalent terms, are meant to include the subgroups of the compounds of general formula I as well as their salts, solvates, and stereoisomers.

When any variable occurs more than once in any moiety, each definition is independent. Any limited definitions of the radicals specified herein are meant to be applicable to the group of compounds of formula I as well as to any subgroup defined or mentioned herein. For instance, when K is —(CHR$_6$)$_n$— and p is 5, then each of the 5 occurring $R_6$ variables are defined independently which means that, by way of example, the following moieties are within the definition of K: —CH$_2$—CH$_2$—CH(CH$_3$)—CH$_2$—CH$_2$— or —CH(CH$_3$)—CH$_2$—CH$_2$—CH$_2$—CH$_2$— or the like.

Interesting subgroups of the compounds of formula I are those compounds of formula I wherein one or more of the following restrictions apply:
$R_1$ is F;
$R_2$ is H or F;
$R_2$ is H;
$R_3$ is $C_{1-4}$alkyl or cyclopropyl;
$R_3$ is ethyl, isopropyl or cyclopropyl;
$R_3$ is ethyl or isopropyl;
$R_4$ is methyl;
$R_4$ is methyl and in a stereoconfiguration that the carbon to which the methyl group is attached is (S):
J is —N($R_5$)—SO$_2$—,

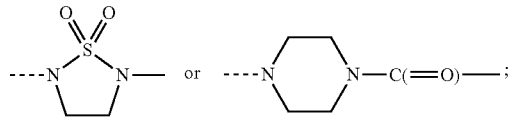

J is —N($R_5$)—SO$_2$— or

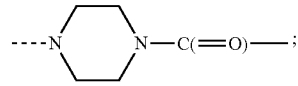

K is —(CHR$_6$)$_p$— wherein p is 3, 4, 5 or 6 and each $R_6$ is independently H or CH$_3$;
K is —(CHR$_6$)$_p$— wherein p is 3, 4, 5 or 6 and each $R_6$ is H;
K is —(CHR$_6$)$_p$— wherein p is 4 or 5 and each $R_6$ is H;
K is *-(CH$_2$)$_q$—CH=CH—CH$_2$— wherein q is 2 or 3;
L is —O— or —O—CH$_2$—;
$R_5$ is $C_{1-4}$alkyl or $C_{3-5}$cycloalkyl,
$R_5$ is methyl, ethyl or cyclopropyl,
$R_5$ is methyl,
the -JKL- linking chain, i.e. the atoms forming the connection between the phenyl ring and pyridazinone ring of formula I, is 8 to 11 atoms long.

The pharmaceutically acceptable salt forms, which the compounds of the present invention are able to form, can conveniently be prepared using the appropriate acids or bases.

The compounds of formula I containing a basic functionality can form pharmaceutically acceptable acid addition salts with appropriate acids such as inorganic acids, for example hydrohalic acids (e.g. hydrochloric or hydrobromic acid) sulfuric, hemisulphuric, nitric, phosphoric, and the like; or organic acids such as methanesulfonic, ethanesulfonic, benzenesulfonic, p-toluenesulfonic, and the like. Conversely said acid addition salt forms can be converted into the free base form by treatment with an appropriate base.

The compounds of formula I containing acidic protons may be converted into their pharmaceutically acceptable metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary, and tertiary aliphatic and aromatic amines such as methylamine, ethylamine, propylamine, isopropylamine, the four butylamine isomers, dimethyl-amine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term "solvate" covers any pharmaceutically acceptable solvate that the compounds of formula I as well as any pharmaceutically acceptable salt thereof, are able to form. Such solvates are for example hydrates, alcoholates, e.g. ethanolates, propanolates, and the like.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i e minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms or stereoisomers of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl¬tartaric acid, ditoluoyltartaric acid and camphor-sulfonic acid. Alternatively, enantiomers may be separated by chromatographic techniques using chiral stationary phases. Said pure stereochemically isomeric forms may also be derived from the corresponding pure stereoisomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula I can be obtained separately by conventional methods. Appropriate physical separation methods that may advantageously be employed are, for example, selective crystallization and chromatography, e.g. column chromatography or supercritical fluid chromatography.

The compounds of formula I or subgroups thereof may have several centres of chirality. Of particular interest is the stereogenic centre of the piperazinone ring at the $R_4$-substituted carbon atom. The configuration at this position may be (R) or (S), in particular the configuration at this position is (S) as illustrated by formula I(S).

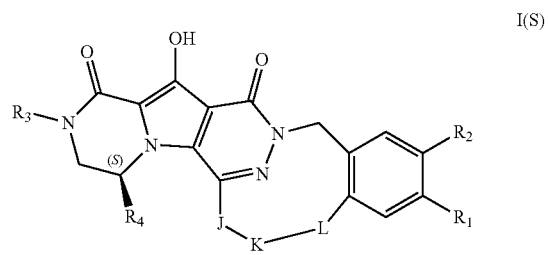

In case K in the -JKL- linker contains a double bond, then the Z-configuration of such double bond is of interest.

A compound according to the invention can generally be prepared by a succession of steps, each of which is known to the skilled person. In particular, the compounds in this patent application can be prepared according to one or more of the following preparation methods. In the following schemes, and unless otherwise indicated, all variables used are as defined for compounds of Formula I.

The macrocycles with the general formula I of the present invention can be prepared through a cyclization reaction involving an "open" precursor of the general formula IIa, IIa' or IIa" in which the hydroxyl function of the pyrrole ring in I is protected by methylation. Said macrocyclization can be effected through the formation of an amide bond, an ether bond, or an alkene bond, and is generally effected in the linker region J-K-L, as is exemplified in scheme 2a. The deprotection of the methyl group in compounds of the general formula III can be effected by a variety of methods (Scheme 1). In a first embodiment, the precursor III is treated with a metal chloride, such as lithium chloride, in a polar aprotic solvent, such as dimethylformamide (DMF). This transformation is most advantageously carried out in a temperature range between 90° C. and 150° C. In a second embodiment, the macrocycle of the general formula III can be treated with sodium iodide and tetrachloro silane in a solvent mixture consisting of a polar aprotic solvent, such as acetonitrile or the like, and an aromatic apolar solvent, such as toluene or the like. Said transformation is advantageously carried out in a temperature range between 0° C. and room temperature. In a third embodiment, the precursor III is treated with a boron reagent, such as boron tribromide ($BBr_3$), in an aprotic solvent such as dichloro methane, at low temperature, such as at −78° C.

Scheme 1

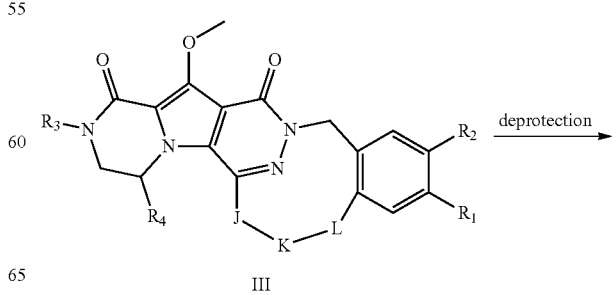

III

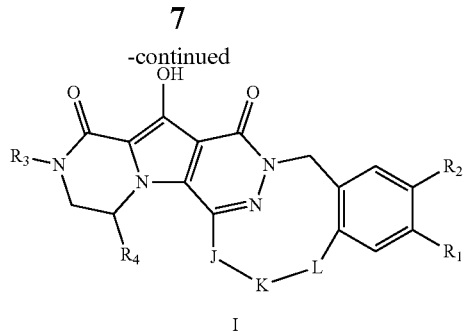

(I)

The macrocycles of the general formula IIIa, IIIa' and IIIa" can be synthesized by a macrolactamization reaction as is shown in Scheme 2a. This transformation requires the presence of a dehydrating reagent. Commonly used examples are HBTU (O-benzo-triazole-N,N,N',N'-tetramethyl uronium hexafluorophosphate), EDCI (1-ethyl-3-(3-di-methyl-aminopropyl)carbodiimide)(1-ethyl-3-(3-dimethylamino-propyl)¬carbodiimide), EDAC (1-ethyl-3-(3-dimethylami-nopropyl) carbodiimide hydro¬chloride), or FDPP (pentafluorophenyl diphenylphosphinate). In a particular embodiment said dehydrating reagent is HBTU or FDPP. The reaction is typically performed by slow addition of the open precursor of the general formula IIa, IIa' or IIa" to a mixture containing said dehydrating agent and an excess amount of a tertiary amine, such as diisopropyl ethyl amine A useful solvent is an aprotic solvent, or more preferably a polar aprotic solvent. Examples of aprotic solvents include $CH_2Cl_2$ (DCM), DMF, $CH_3CN$, $CHCl_3$, etc. Examples of polar aprotic solvents include DMF, dimethylacetamide (DMA), N-methylpyrrolidone (NMP) or dimethyl sulfoxide (DMSO). Under certain circumstances the use of hydroxybenzotriazole (HOBT) or similar compounds as an additive in the coupling reaction is an advantage. In a preferred embodiment the cyclization reaction is carried out at low concentration of the open precursor, such as in the range between 1 and 10 mM.

Scheme 2a

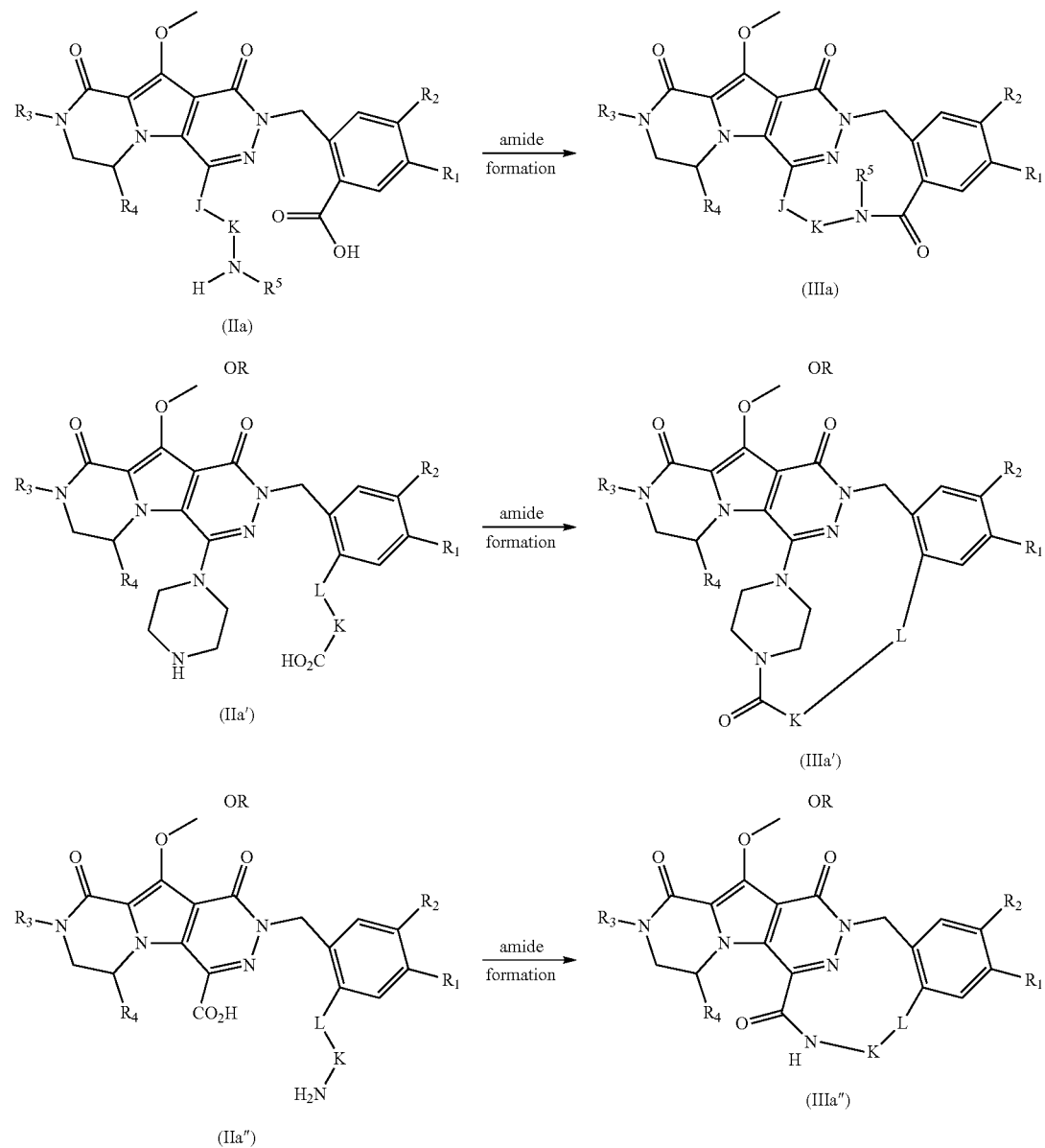

The macrocycles of the general formula IIIb can be synthesized by a Mitsunobu reaction as is shown in Scheme 2b. This transformation can be effected by treatment of a dihydroxy open precursor of the general formula IIb with a phosphine, such as triphenyl phosphine or tributyl phosphine, and a dialkylazo dicarboxylate reagent such as diisopropyl azo dicarboxylate (DIAD) or diethylazo dicarboxylate (DEAD). The reaction is advantageously carried out in a polar aprotic solvent, such as tetrahydrofuran (THF), or an apolar solvent, such as toluene, and requires a reaction temperature between −20° C. and 50° C.

Scheme 2b

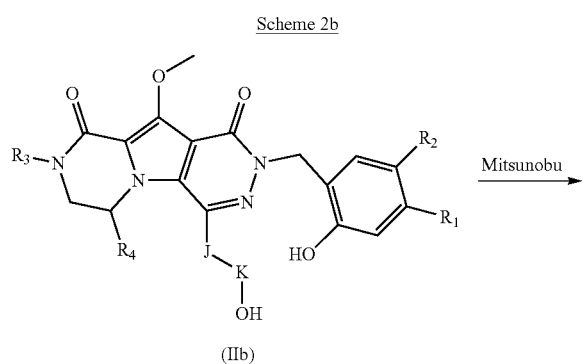

(IIb)

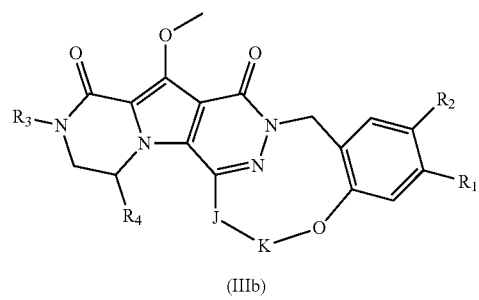

(IIIb)

The macrocycles of the general formula IIIc can be synthesized by a macro-etherification reaction as is shown in Scheme 2c. This transformation can be effected by treatment of the open precursor IIc, containing an hydroxyl alkyl substituent and a benzylic halide, such as a chloride, with a strong inorganic base, such as KOtBu, in a polar, aprotic solvent, such as DMA. The reaction temperature is between −10° C. and 20° C., in particular at about 0° C.

Scheme 2c

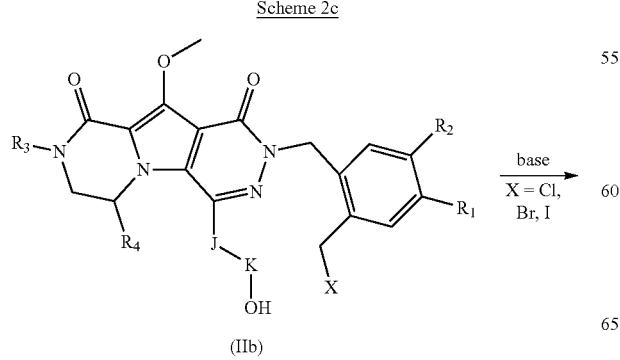

(IIb)

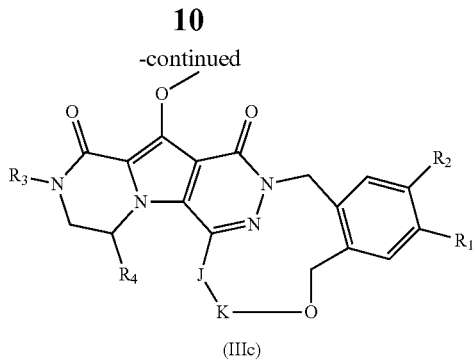

(IIIc)

The macrocycles of the general formula IIId, i.e. wherein K is a $C_{3-6}$alkenylene, can be synthesized by an olefin metathesis macrocylization reaction as is shown in Scheme 2d. Said transformation is performed using a ruthenium catalyst, such as a first generation Grubbs catalyst (e.g. 1,3-Bis-(2,4,6-trimethyl-phenyl)-2-imidazolidinylidene)(dichloro-phenylmethylene) (tricyclohexylphosphine)ruthenium) or a second generation Hoveyda-Grubbs catalyst (e.g. (1,3-Bis-(2,4,6-trimethylphenyl)-2-imidazolidin-ylidene)dichloro(o-isopropoxyphenylmethylene)ruthenium). A preferred solvent is an halogenated solvent, such as di-chloro methane, and the reaction temperature is in the range between 30° C. and 90° C. Said transformation can afford the macrocycle of the general formula IIId as an E-isomer or a Z-isomer, or a mixture thereof, that can be separated using chromatographic techniques known to the skilled person, such as by supercritical $CO_2$ chromatography. The starting compound IId is obtained following the reaction pathways described for scheme 5b for introducing the allyloxy substituted phenyl moiety, and the reaction pathway described for schemes 7a-b and 8a for reacting the fluoro pyridazinone with the appropriate A-$(CH_2)_n$—CH=$CH_2$ group.

Scheme 2d

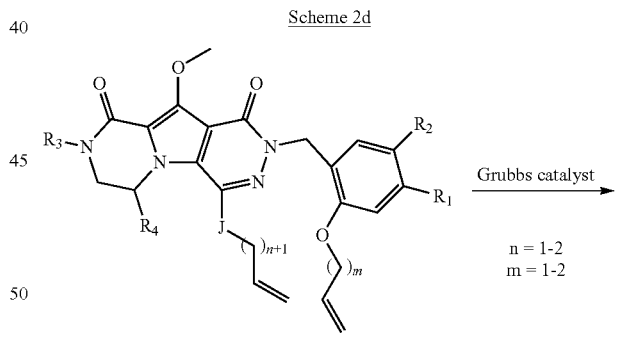

(IId)

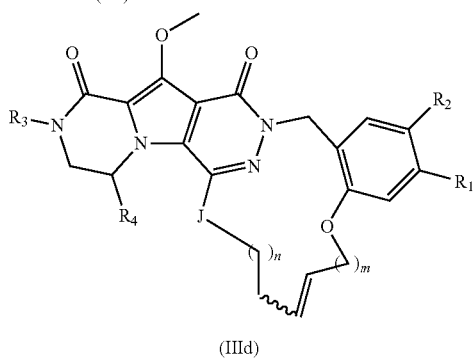

(IIId)

Macrocycles wherein K is a $C_{3-6}$alkynylene, can be obtained by a method similar to the procedure for macrocycles of general formula IIId but using an alkyne metathesis macrocyclisation reaction as known in the art.

Macrocycles can be further derivatized as illustrated by Schemes 3a and 3b. For example in Scheme 3a, the macrocycle of the general formula IIIa" is alkylated by treatment with an alkyl halide $R^5$—X, preferably an iodide and/or primary alkyl, such as iodo methane or iodo ethane, and requires the presence of a strong inorganic base, such as NaH. The transformation is advantageously effected in a polar aprotic solvent, such as THF, at a reaction temperature between 0° C. and 20° C.

Scheme 3a

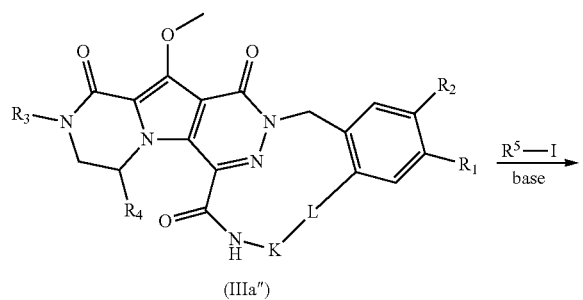

(IIIa″)

Alternatively, a macrocycle of the general formula IIIe can be alkylated to obtain macrocycle IIIf by treatment with a primary alkyl halide (Scheme 3b), preferably an iodide, such as iodo methane, and requires the presence of a strong lithium amide base, such as lithium diisopropyl amide (LDA) or lithium hexamethyldisilazide (LiHMDS). The reaction is carried out in a polar aprotic solvent such as THF, at a temperature between −78° C. and 20° C.

Scheme 3b

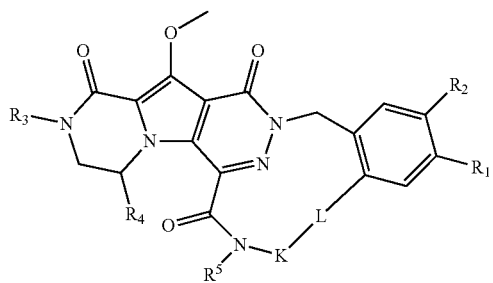

(IIIe)

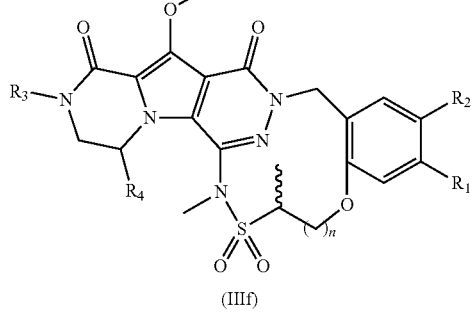

(IIIf)

n = 2-5

The macrocycle precursors of the general formula IIa can be prepared by the methods illustrated by Schemes 4a-4-e.

Benzylation of the tricyclic amine IVa to obtain the structure of the general formula IVc can be effected by treatment with a strong lithium amide base, such as LiHMDS, in an aprotic polar solvent, such as DMF, in a temperature range between 0° C. and 20° C., in particular at about 10° C. The benzyl moiety is represented by Formula IVb, wherein X is halo, such as bromo or chloro.

Scheme 4a

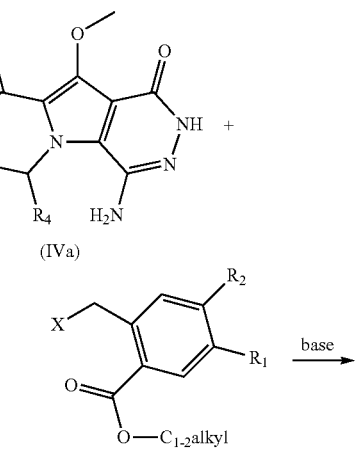

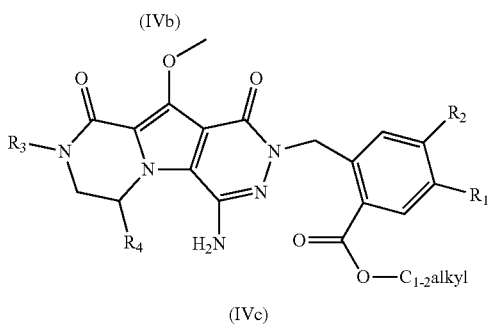

(IVc)

X = Cl, Br, I

A sulfonamido containing linker (J is —N($R^5$)—$SO_2$—) can be introduced starting from IVc as illustrated by Scheme 4b. First, the amino is transformed into a fluoro by a Sandmeyer reaction effected by treatment of IVc with a nucleophilic fluoride reagent, such as hydrogen fluoride in pyridine in the presence of a diazotation agent, such as sodium nitrite, in a temperature range between 0° C. and 20° C., to afford the fluoro compound IVd. Then, the fluoro precursor IVd is treated with a sulfonamido containing linker having formula L1 in the presence of an inorganic base, such as cesium carbonate, in a polar organic solvent, such as DMSO, in a temperature range between 50° C. and 100° C., to afford the protected macrocycle precursor of the general formula IVe. Subsequently, the linker precursor moieties are deprotected. The carboxylic ester moiety in IVe is hydrolysed. This can be done using a metal hydroxide (M-OH), such as potassium hydroxide, sodium hydroxide, or lithium hydroxide. The reaction is performed in an aqueous environment, and is most advantageously carried out in the presence of at least one water miscible organic co-solvent, such as methanol, ethanol or THF. Removal of the amine Boc protecting group can be achieved by treating the resulting Boc carboxylic acid with a solution containing trifluoro acetic acid, optionally in the presence of triisopropyl silane, in an aprotic solvent, such as dichloro methane, to afford the macrocycle precursor of the general formula IIa-1. In a preferred embodiment, Boc removal is carried out between 0° C. and room temperature. Alternatively, said deprotection can be effected by treatment of the Boc carboxylic acid with a solution of hydrochloric acid in a polar, aprotic solvent, such as dioxane, in particular with a 4N solution of HCl in dioxane.

An amino containing linker (J is —N(R$_5$)—) can be introduced by a reductive amination from IVc as illustrated by Scheme 4c. First, the intermediate imine is formed by treatment of the amine IVc with the aldehyde L2 in a protic organic solvent such as 2-propanol, in the presence of an acid, such as a carboxylic acid, such as acetic acid. This reaction requires elevated temperature, such as in the range of about 60° C. to about 90° C. The second stage of the reductive amination is carried out at lower temperature, such as at 0° C., and requires a reducing agent, such as sodium borohydride, and a protic organic solvent, such as methanol. The protecting group in the L2 moiety can be an acid labile benzyl function, such as 2,4-dimethoxy benzyl.

Scheme 4c

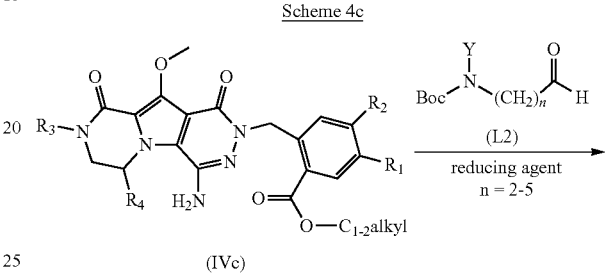

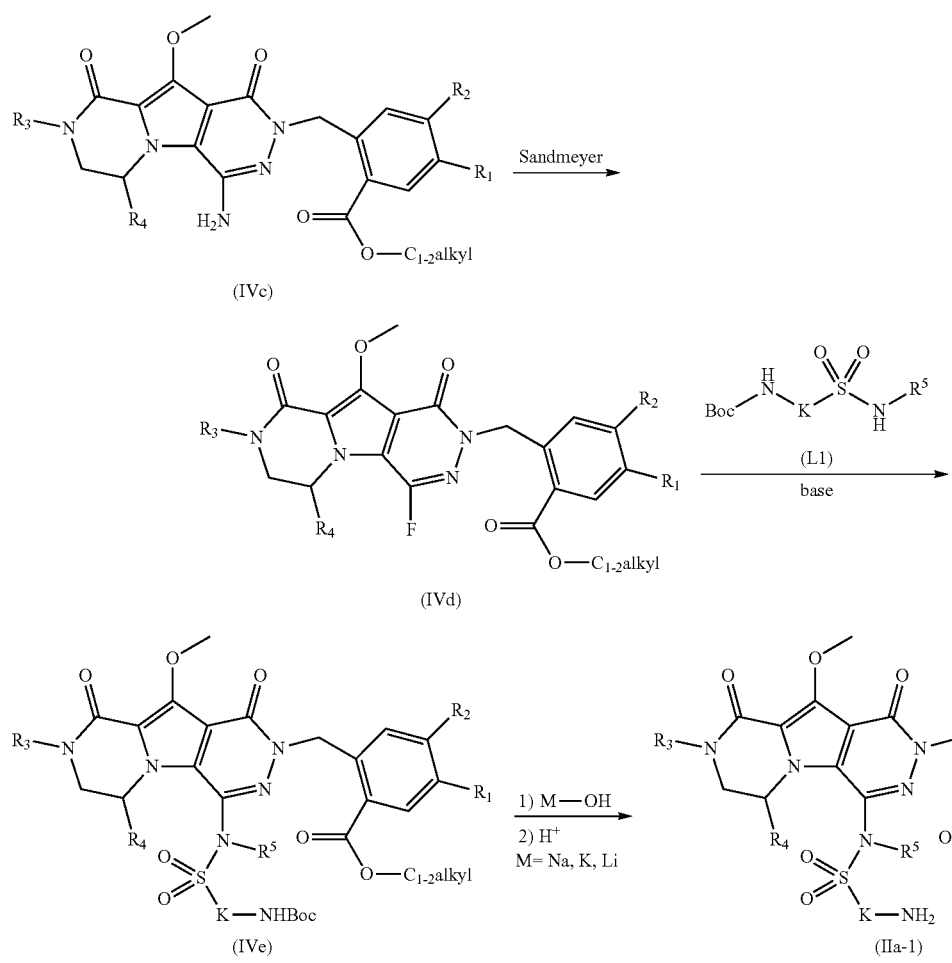

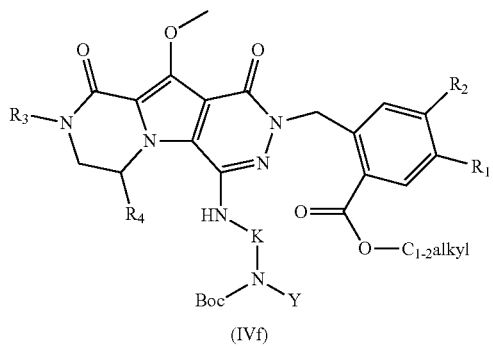

(IVf)

Y = R₅ or protecting group (PG)

The amine in IVf-1 can be alkylated to afford the tertiary amine of the general formula IVf-2 ($R_5$ is $C_{1-4}$alkyl or cyclopentyl) as is shown in Scheme 4d. The amine IVf-1 is treated with a strong base, such as NaH, in a polar aprotic solvent, such as THF, at a temperature between −10° C. and 5° C. An alkyl iodide of formula $R_5$—I is then used to react with the anion.

Scheme 4d

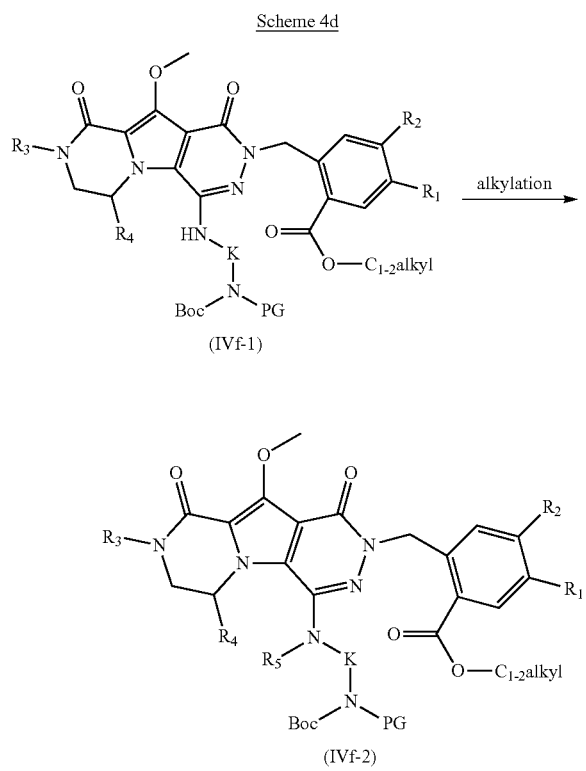

(IVf-1)

alkylation (IVf-2)

R = $C_{1-4}$alkyl
PG = substituted benzyl, e.g. 2,4-dimethoxy benzyl

A deprotection procedure similar to the one described for Scheme 4b above but starting from the compound of the general formula IVf-3 results in the amino acid macrocycle precursor of the general formula IIa-2 and is illustrated by Scheme 4e.

Scheme 4e

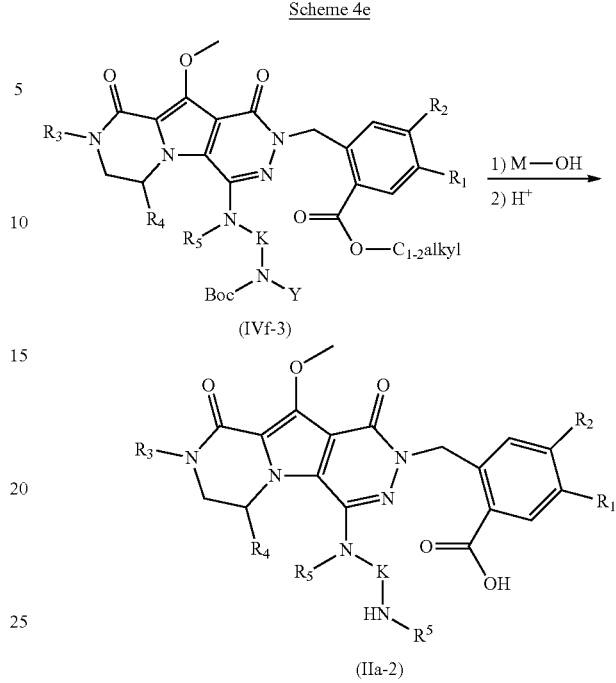

(IVf-3)

1) M—OH
2) H⁺

(IIa-2)

M = Na, K, Li
Y = PG or R⁵

Macrocycle precursors of the general formula IIa' can be prepared by the methods illustrated by Schemes 5a-5d, as is exemplified for the preparation of IIa-1' (compounds of formula IIa' wherein L is —O—). The tricyclic amine IVa is converted into the corresponding fluoro compound Va (Scheme 5a), according to similar procedures as described hereinbefore (Scheme 4a).

Scheme 5a

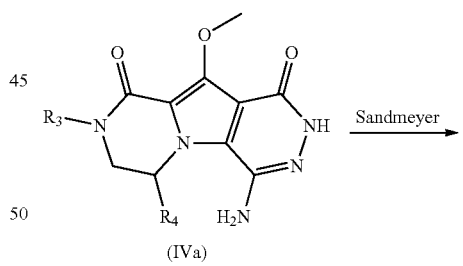

(IVa)

Sandmeyer

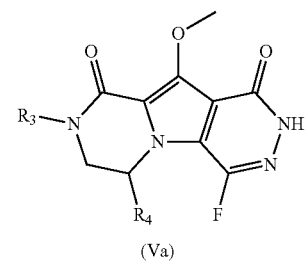

(Va)

The pyridazinone moiety in Va can be benzylated following 2 alternative protocols (Scheme 5b). In a first embodiment, this benzylation is effected by a Mitsunobu reaction similar to the one described hereinbefore (Scheme 2b), using the protected benzyl alcohol A1. In a second embodiment, the benzylation is done similarly as described hereinbefore for Scheme 4a, using the protected benzyl halide A2.

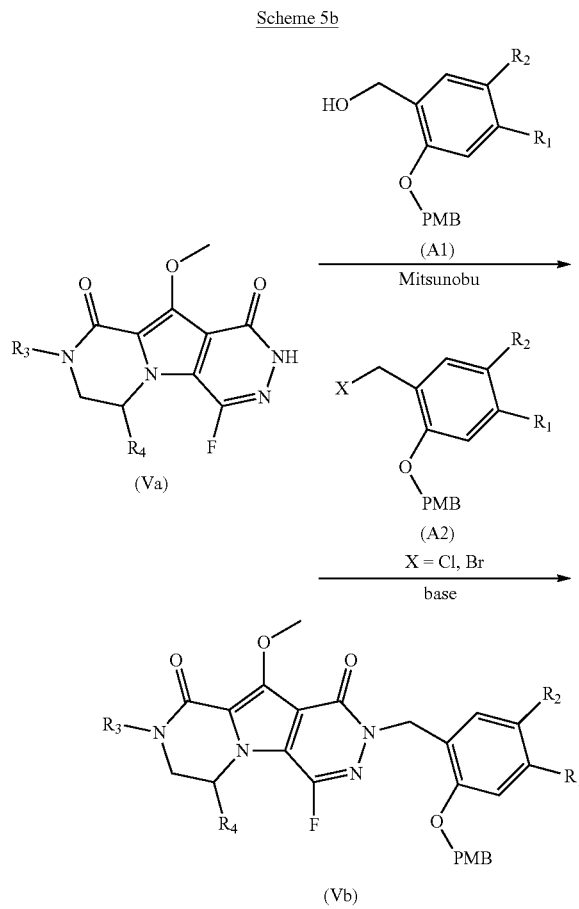

The piperazinyl moiety (for compounds of formula I wherein J is

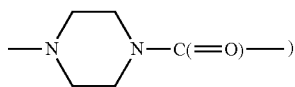

is introduced by treatment of the fluoro pyridazinone Vb with piperazine, in a polar aprotic solvent, such as NMP, in a temperature range between 110° C. and 130° C. Under these reaction conditions the methoxy group in the pyrole ring is de-methylated to provide the corresponding hydroxyl in the resulting compound of the general formula Vc. The piperazinyl is protected with a Boc group by treatment with $Boc_2O$ in a protic solvent, such as methanol, in a temperature range between 0° C. and 20° C. to afford the compound of formula Vd. The hydroxyl is re-protected by treatment with iodo methane in the presence of an inorganic base, such as potassium carbonate, in a polar aprotic solvent such as DMF in a temperature range between 0° C. and 20° C., to afford the compound of formula Ve.

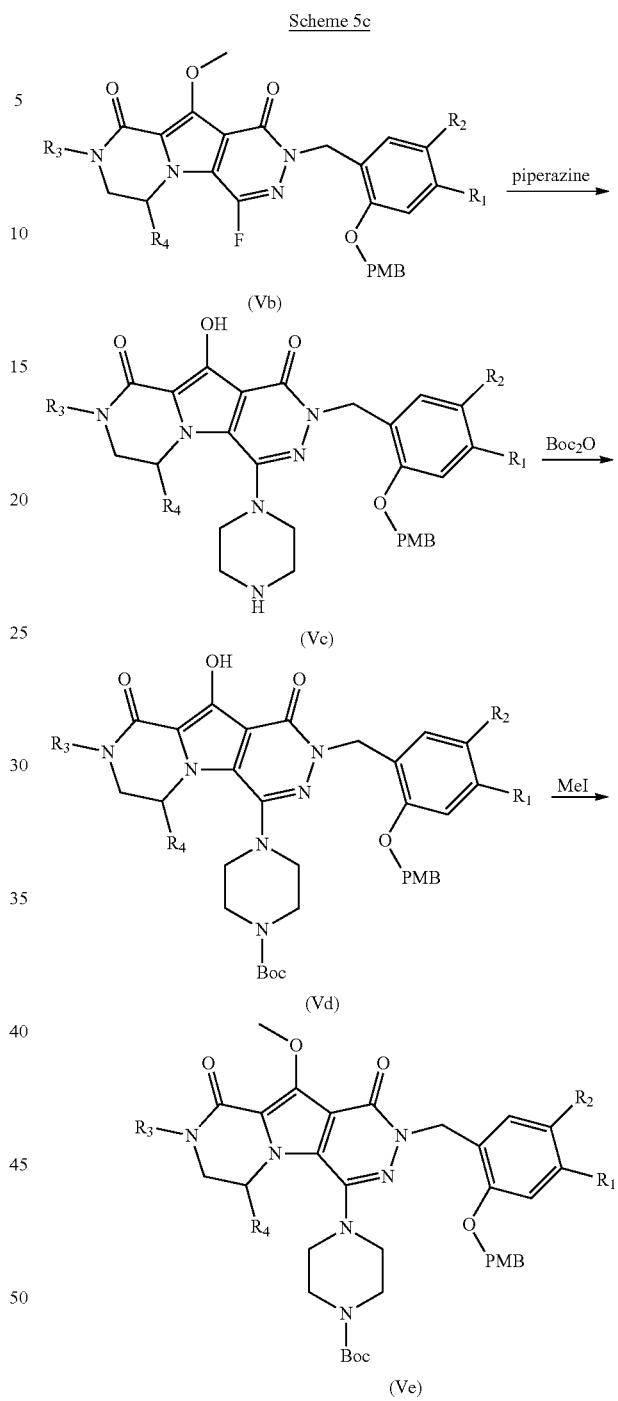

Deprotection of the para methoxy benzyl (PMB) group is effected by treatment with a strong acid, such as HCl in an aprotic solvent, such as 1,4-dioxane, or, trifluoro acetic acid (TFA), optionally in the presence of a halogenated co-solvent such as DCM, in a temperature range between 0° C. and 20° C. to afford the compound of formula Vf. As a consequence, concomitant Boc de-protection occurs and re-protection of the piperazine using $Boc_2O$ similarly as described hereinbefore, is needed to afford the compound of formula Vg. Introduction of the carbon linker (—K—) is achieved by treatment with a halogenated alkanoate L4 in the presence of an inorganic base such as potassium carbonate, in a polar aprotic solvent such as DMF, in a temperature range between 0° C. and 20° C., to afford the compound of formula Vh. A deprotection procedure analogous to the one described for Scheme 4b and starting from the compound of the general formula Vh results in the amino acid macrocycle precursor of the general formula IIa-1', as is shown in Scheme 5d.

The macrocycle precursors of the general formula IIa" can be prepared by the methods as illustrated by Scheme 6, as is exemplified for the preparation of IIa-1" (compound of IIa" wherein L is —O—). The first step involves a Mitsunobu reaction as is shown in Scheme 6, which is achieved similarly to the reaction described for Scheme 2b using compound of the general formula VIa and the benzyl alcohol A3 with a phosphine, such as triphenyl phosphine or tributyl phosphine, and a dialkylazo dicarboxylate reagent such as diisopropyl azo dicarboxylate (DIAD) or diethylazo dicarboxylate (DEAD). The reaction is advantageously carried out in a polar aprotic solvent, such as THF, or an apolar solvent, such as toluene, and requires a reaction temperature between −5° C. and 20° C. to give the compound of formula VIb. A similar deprotection sequence as described for Scheme 4b, starting from the compound of the general formula VIb results in the amino acid macrocycle precursor of the general formula IIa-1".

Scheme 5d

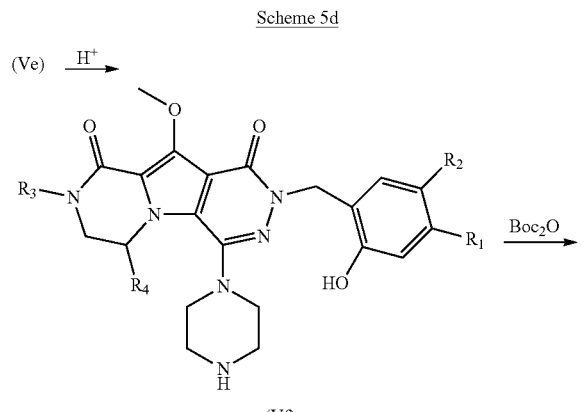

(Vf)

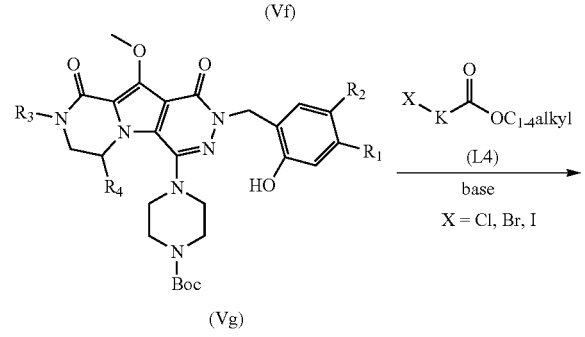

(Vg)

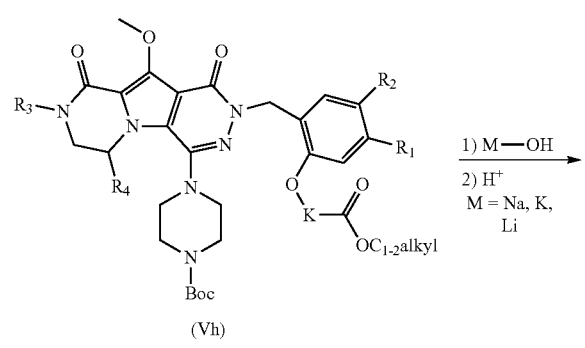

(Vh)

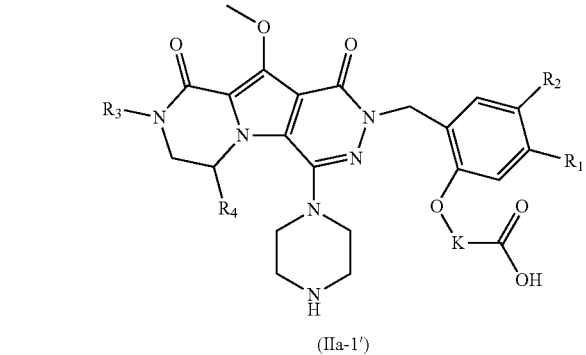

(IIa-1')

Scheme 6

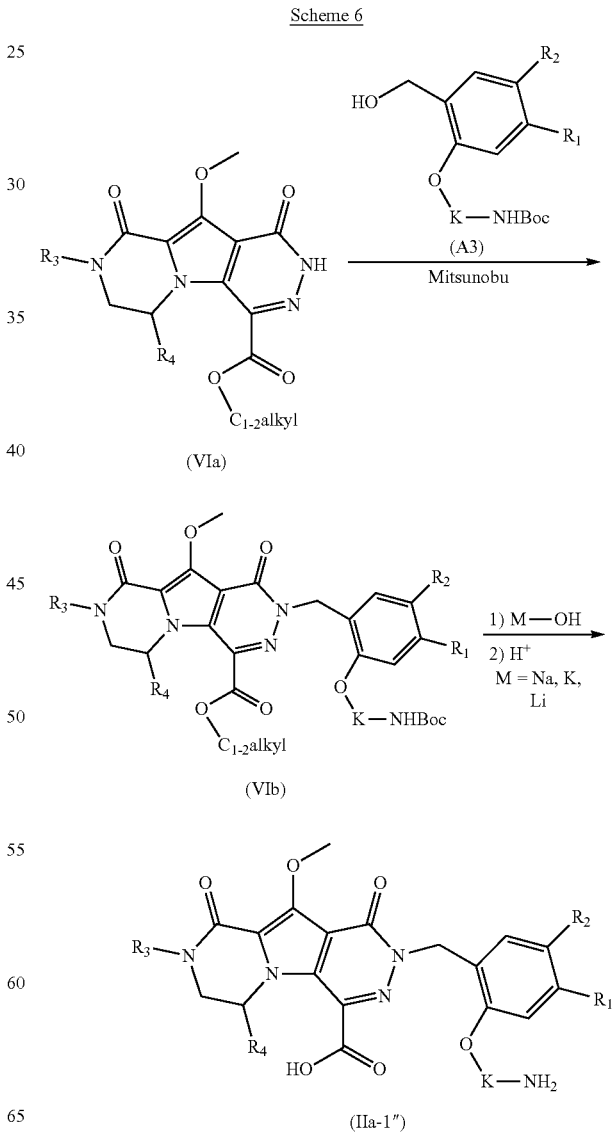

(IIa-1")

The macrocycle precursors of the general formula IIb can be prepared by the methods illustrated by Schemes 7a-7b, exemplifying synthesis of compounds IIb-1 (compound IIb wherein J is —N(R⁵)—SO₂—) and IIb-2 (compound IIb wherein J is

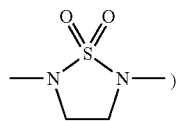

) respectively. As illustrated in Scheme 7a, the sulfonamido containing linker L3 is introduced by a nucleophilic displacement reaction of the fluoro tricycle Vb with L3, in which the alcohol is protected as an alkanoate —C(=O)—R. Said reaction is carried out in a polar solvent, such as DMSO, and requires the presence of an inorganic base, such as cesium carbonate. The reaction is most advantageously carried out at a temperature between 50° C. and 80° C., to provide a compound of formula VIIa. Removal of the alkanoate protecting group can be effected by treatment with a base, such as NaOH, LiOH, in a protic solvent, such as methanol or ethanol, at room temperature. Removal of the PMB protecting group can be effected by treatment with an acid, such as TFA in an halogenated solvent, such as DCM, or, with HCl in a polar solvent, such as 1,4-dioxane, to afford the macrocycle precursor IIb-1.

Scheme 7a

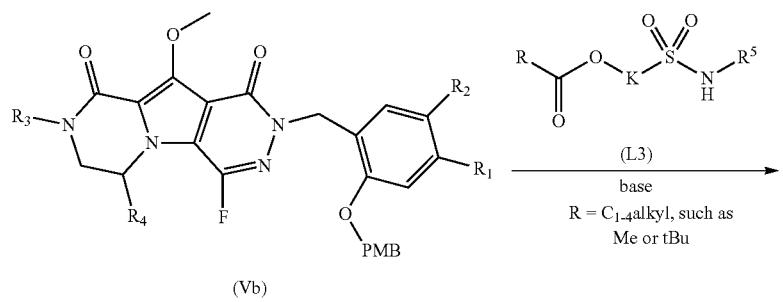

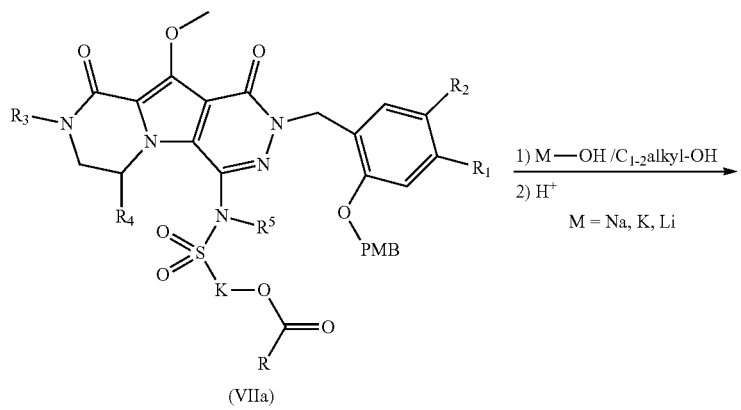

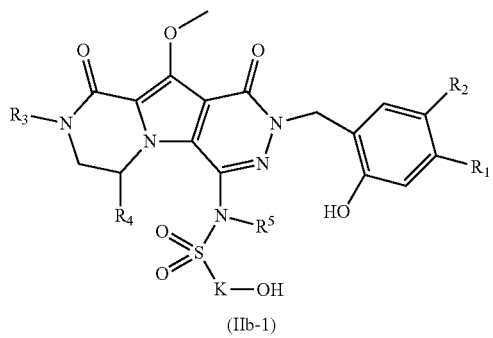

The synthesis of the macrocycle precursors of the general formula (IIb-2, scheme 7b) starts with nucleophilic displacement of the fluorine atom in the compound of formula Vb, using 1,2,5-thiadiazolidine 1,1-dioxide, to afford the compound of formula VIIIa, similarly as described hereinbefore for scheme 7a. Further construction of the linker involves alkylation with an acyl protected halo alkanol L4. Said alkylation is effected by treatment with L4 in the presence of a strong inorganic base, such NaH, in a polar solvent, such as DMF, in a temperature range between 80° C. and 120° C., in particular at about 100° C., to afford the compound of formula VIIIb. Deprotection to afford the compound of formula IIb-2 is effected similarly as described hereinbefore for scheme 7a.

Scheme 7b

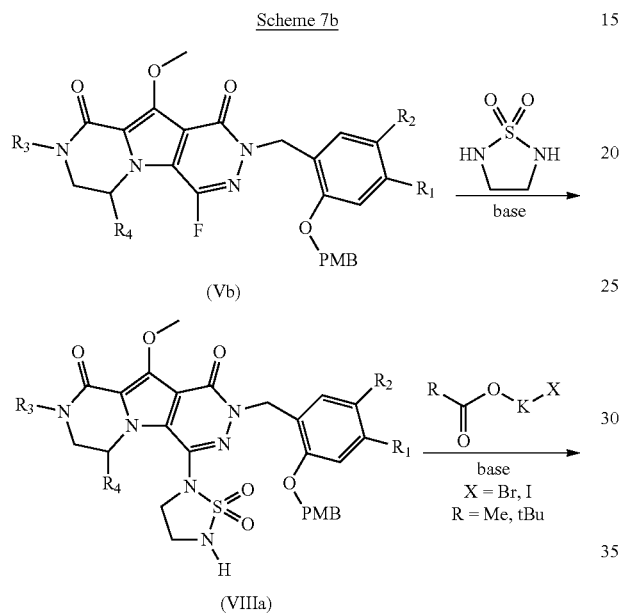

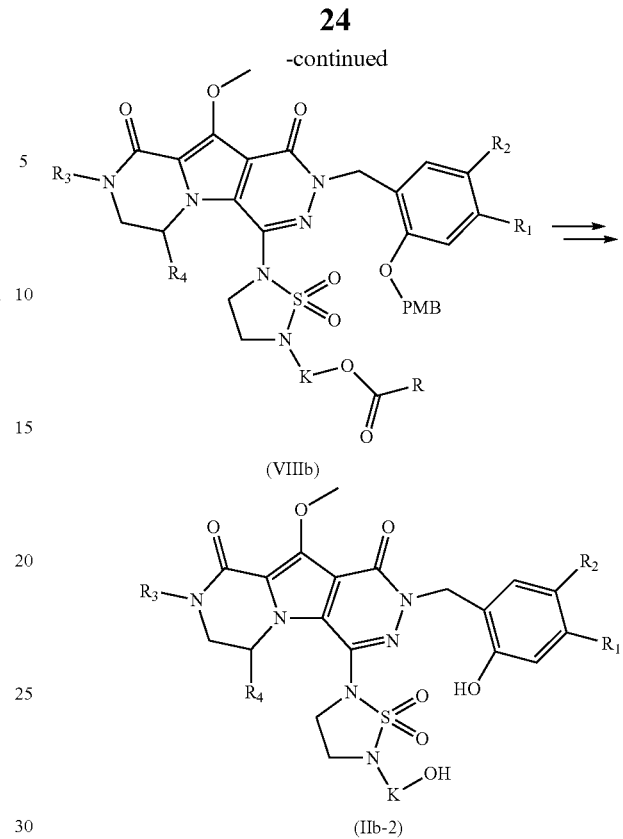

The macrocycle precursors of the general formula IIc can be prepared by the method illustrated by Scheme 8a and exemplified for compounds of the formula IIc-1 (wherein J is —N(R$^5$)—SO$_2$—). The sulfonamido containing linker L3 is introduced by a nucleophilic displacement reaction of the fluoro tricycle IVd with L3, in which the alcohol is protected as an alkanoate, similarly as described hereinbefore (scheme 7a), to afford the compound of formula IXa.

Scheme 8a

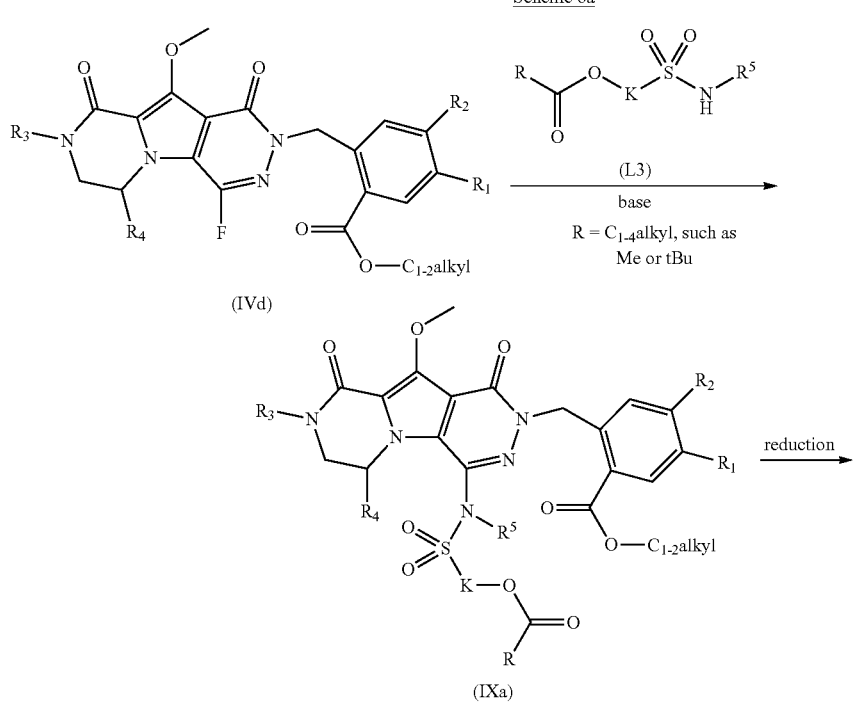

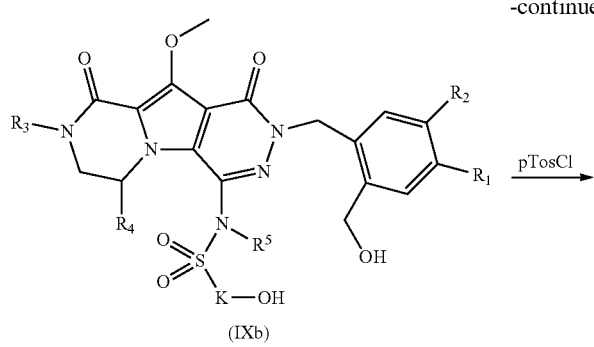

(IXb)

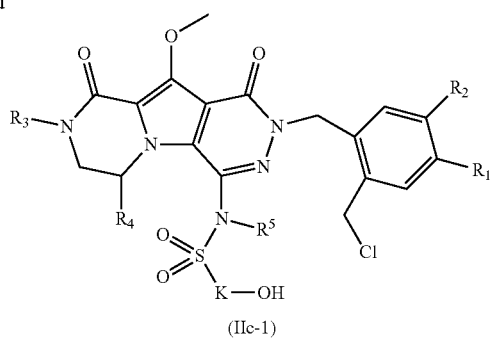

(IIc-1)

Reduction of the two ester functions is achieved by a metal hydride reagent, such as NaBH$_4$, in a solvent system comprising a polar, aprotic solvent, such as THF, and a protic solvent, such as an alcoholic solvent, such as methanol. The reaction is effected in a temperature range between 50° C. and 80° C., such as 65° C., to afford the bis-alcohol of formula IXb. The macrocycle precursor of formula IIc-1 can be prepared by reaction with pTosCl in the presence of a tertiary amine base, such as triethyl amine, in an halogenated solvent, such as DCM, at a temperature range between 0° C. and 20° C. (scheme 8a).

The amino tricycle of the formula IVa may be obtained from the common precursor Xa as illustrated by schemes 9a-9b. The first step involves treatment of Xa with the primary amine R$^3$—NH$_2$ as the solvent, in a temperature range between 20° C. and 90° C. Acylation with bromo acetylbromide takes place in a basic biphasic solvent system consisting of ethyl acetate and saturated aqueous NaHCO$_3$ at 0° C. to give the bromide of the formula Xc. Cyclization is effected by treatment with a strong inorganic base, such as NaH, in a polar solvent, such as THF, at a temperature between 0° C. and room temperature, to afford the carbobenzyloxy (Cbz) protected piperazinone Xd. Reductive removal of the Cbz protecting group is effected under a hydrogen atmosphere in the presence of a palladium catalyst, such as palladium on carbon, in a protic solvent, such as methanol, to afford the piperazinone Xe. The construction of the bicyclic system of the formula Xg comprises two steps. First, an addition-elimination reaction with diethyl ethoxymethylenemalonate is effected in an aromatic solvent, such as toluene, at a temperature between 20° C. and 120° C., to afford the intermediate of the general formula Xf. Subsequent Dieckman condensation is effected in the presence of a strong base, such as LiHMDS, in a polar solvent, such as THF, in a temperature range between –70° C. and room temperature, to afford the bicycle of the general formula Xg.

Scheme 9a

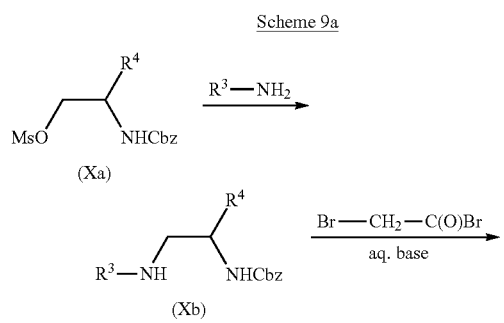

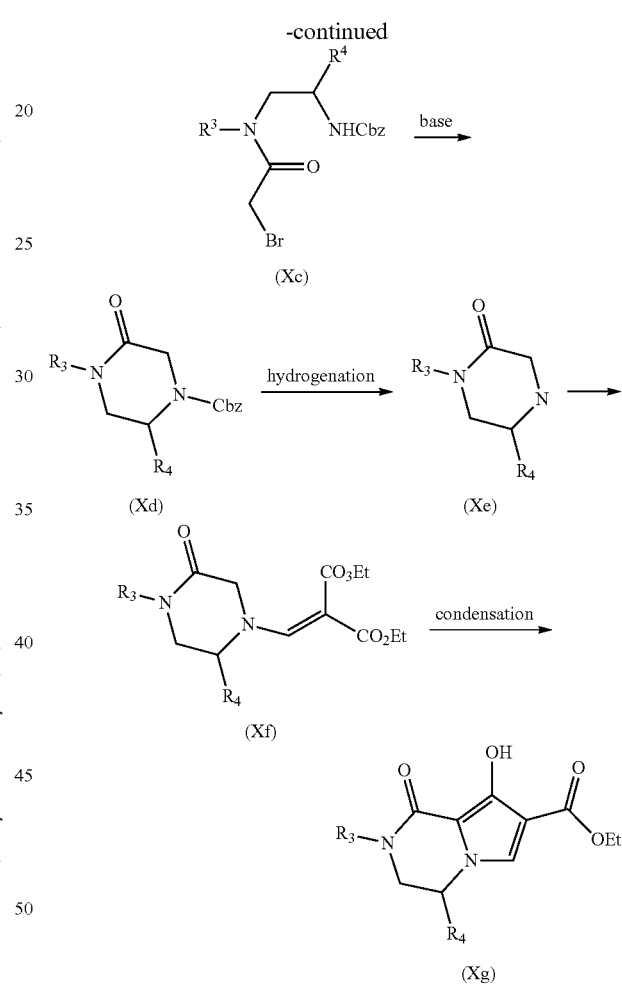

Scheme 9b illustrates the synthesis of the amino funtionalised tricycle of the formula IVa. The hydroxyl function in Xg is protected by methylation using iodo methane in a polar solvent, such as DMF, in the presence of an inorganic base, such as potassium carbonate to afford the bicyclic methoxy pyrole of general formula Xh. Bromination at the free position in the pyrole of general formula Xh is effected by treatment with N-bromosuccinimide in an halogenated solvent, such as dichloro ethane, at a temperature between 0° C. and 25° C. Nucleophilic displacement of the bromide in Xj is effected by CuCN in a polar, aprotic solvent, such as DMF, at a temperature between 90° C. and 130° C., to afford the cyano pyrole of the general formula Xk. Finally, introduction of the third ring is accomplished by reaction of Xk with an excess of hydrazine hydrate in a protic solvent, such as ethanol or tBuOH, at a temperature between 70° C. and 90° C., to afford the amino tricycle of the general formula IVa.

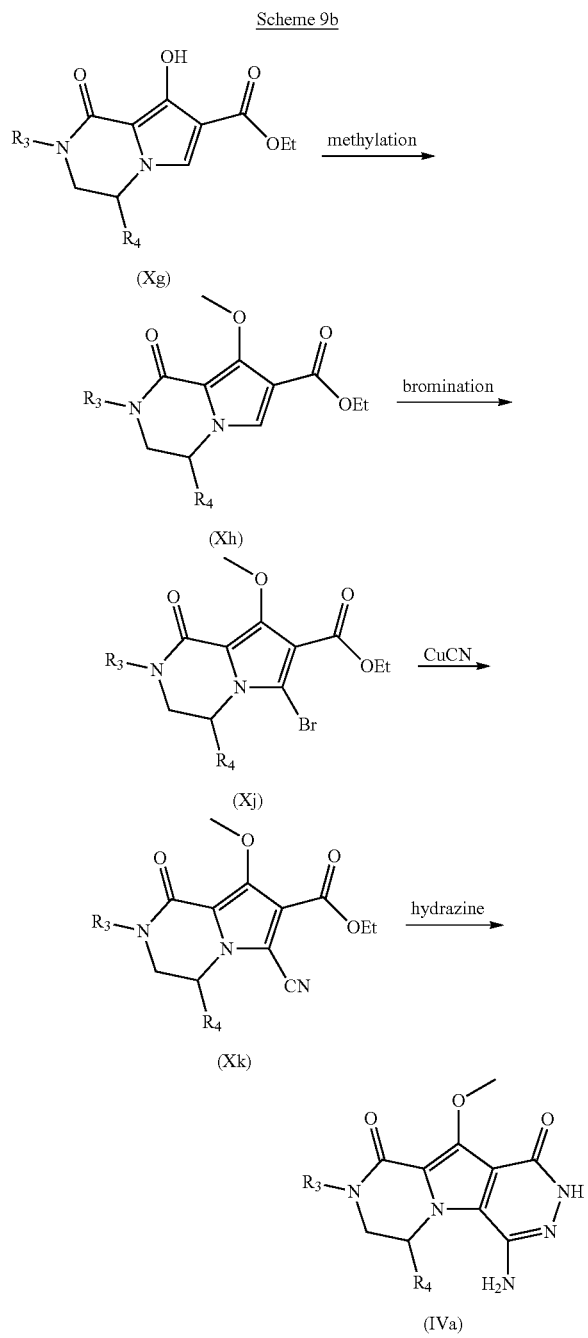

polar, aprotic solvent, such as THF, affords the tricyclic compound of the general formula XIb, which is formed as a hydrazide. The hydrazide XIb can be converted to the corresponding alkoxy carbonyl derivative by an oxidation reaction in the presence of N-bromo succinimide (NBS) in an alkanol solvent, between 10 and 25° C., to afford the corresponding ester VIa.

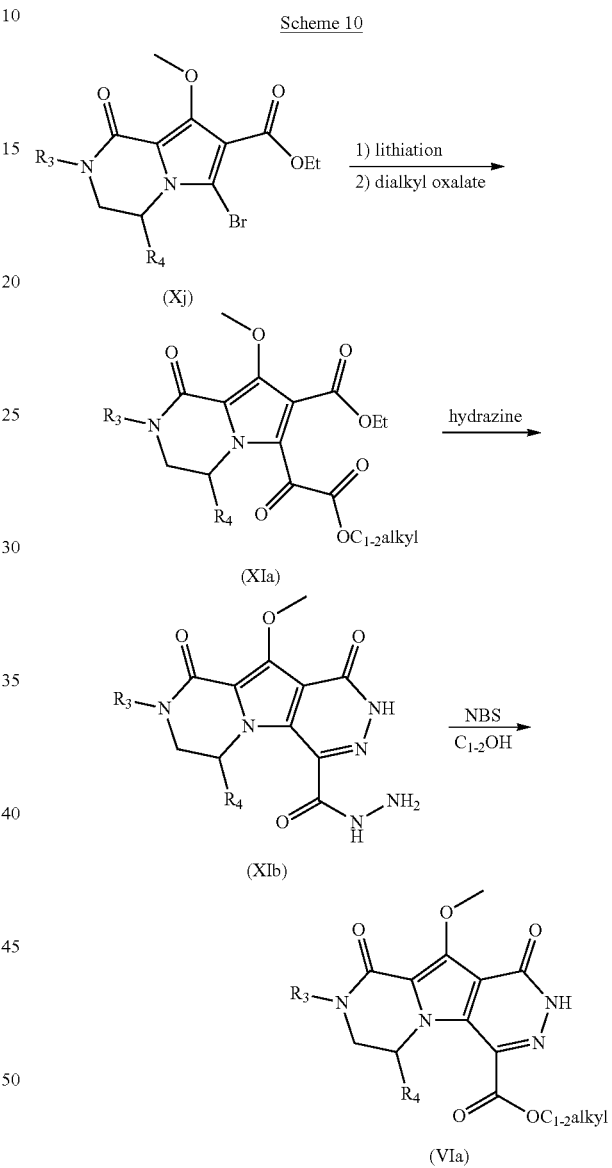

The alkoxy carbonyl functionalized tricycle of the formula VIa can be prepared from the bromo bicycle Xj as is outlined in scheme 10. Lithiation of Xj is effected by treatment with an alkyl lithium reagent, such as n-butyl lithium, in a polar solvent, such as THF, at a temperature between −70° C. and −80° C. Quenching of the lithium anion with a dialkyl oxalate, such as diethyl oxalate, at a temperature between −60° C. and −70° C., affords the compound of the general formula XIa. Reaction with hydrazine in a solvent combination comprising of a protic solvent, such as methanol, and a The bicyclic compound of the general formula Xh can also be prepared from the pyrole XIIa, as shown in Scheme 11, except when $R_3$ is cyclopropyl. First, the pyrole is alkylated by treatment with a strong inorganic base, such as sodium hydride, and an optionally substituted 2,2-Dioxo-[1,2,3]oxathiazolidine XIIb, in a polar solvent, such as DMF, at a temperature between 0° C. and 25° C., to afford the Boc protected amine of the general formula XIIc. This reaction proceeds with inversion of stereochemistry, which is applicable when $R_4$ is not an hydrogen atom. Next, the Boc protecting group is removed under art known conditions, such as with HCl in 1,4-dioxane, as described hereinbefore. The resulting amine of the general formula XIId is cyclised by treatment with an inorganic base, such as potassium carbonate, in a protic solvent, such as ethanol, at a reaction temperature between 60° C. and 90° C., to afford the bicyclic compound of the general formula XIIe. Introduction of the $R_3$ group can be effected by treatment of XIIe with a strong inorganic base, such as sodium hydride, in a polar solvent, such as DMF, at a temperature between −10° C. and 5° C., followed by quenching with an appropriate $R_3$—X, wherein X is preferably bromine or iodine, to afford the bicyclic compound of the general formula Xh. This transformation can only be effected when $R_3$ is not cyclopropyl.

The synthesis of the benzyl precursors of the formulae IVb-1 and A1-A2 are illustrated by schemes IIa and IIb. The benzyl bromide of the formula IVb-1 is prepared by reacting the ester of general the formula IVb-2 with N-bromosuccinimide in an halogenated solvent such as carbon tetrachloride in the presence of a radical initiator, such as benzoic peroxyanhydride, at elevated temperature, in particular reflux temperature (scheme IIa).

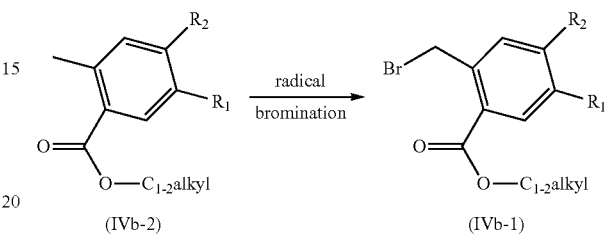

Scheme 11a

The synthesis of the PMB protected benzyl alcohols of the general formula A1 and benzyl bromides A2-1 is illustrated by scheme 11b. The 2-hydroxy benzoate of the formula XIIIa is treated with an inorganic base, such as potassium carbonate, and p-methoxy benzylchloride in a polar solvent, such as acetonitrile, at elevated temperature, such as at reflux temperature, to afford the PMB protected phenol of the formula XIIIb The ester function is reduced by a metal hydride reagent, such as sodium borohydride, in a solvent system consisting of a polar solvent, such as THF, and a protic solvent, such as methanol, at a temperature between 50° C. and 75° C., such as at 65° C., to afford a compound of formula A1. Functional group transformation to obtain the benzyl bromide of formula A2-1 is effected by treatment with carbon tetrabromide and triphenyl phosphine in an halogenated solvent, such as DCM, preferably at room temperature.

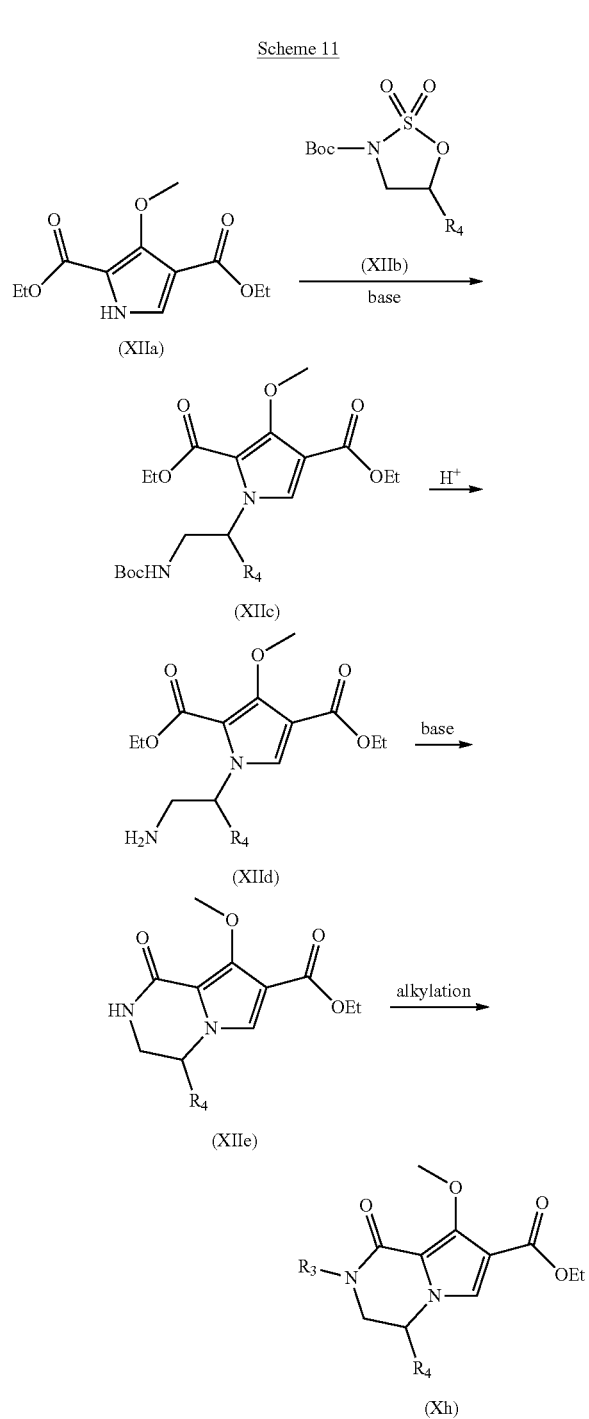

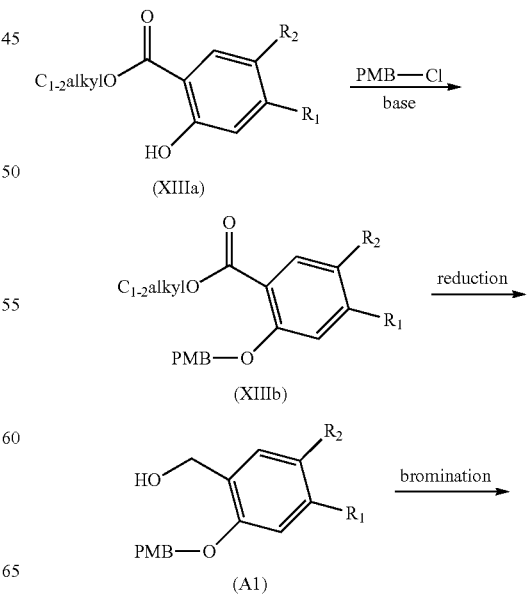

Scheme 11b

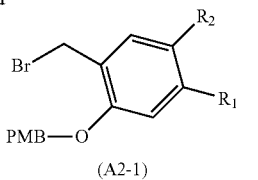

(A2-1)

The benzyl alcohols of formula A3 can be prepared by the methods as is outlined in schemes 12a-b. Mitsunobu reaction of the alkyl 2-hydroxy benzoate of the general formula XIIIa and a N-Boc protected amino alcohol of formula L5 is effected as described hereinbefore (scheme 2b), to afford the precursor of formula XIVa. Reduction of the carboxylic ester can be effected in two ways. The carboxylic ester can be hydrolysed in the presence of aqueous base, similarly as described hereinbefore for scheme 4b, to afford the carboxylic acid of formula XIVb, followed by reduction in the presence of borane, optionally as the dimethyl sulfide complex, in a polar solvent, such as THF, at a temperature between 0° C. and 20° C., to afford the benzyl alcohol of formula A3. Alternatively, the carboxylic ester can be reduced by a metal hydride reagent, such as NaBH$_4$, similarly as described hereinbefore for scheme 8a, to afford the benzyl alcohol of formula A3.

Scheme 12b

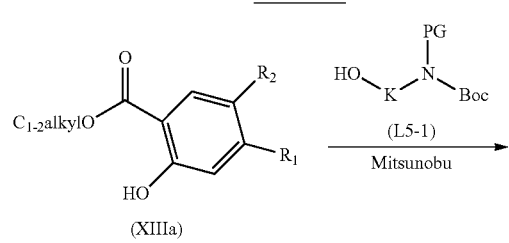

Scheme 12a

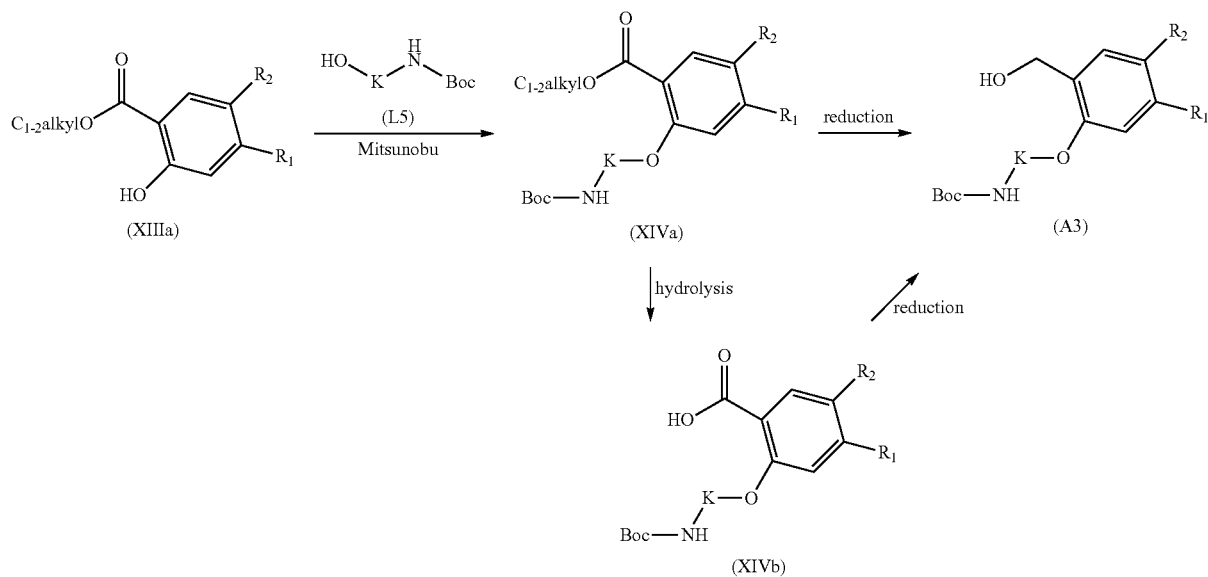

In some instances, such as when $R_1=R_2=F$, it is advantageous to introduce the linker moiety via an alkylation reaction (scheme 12b). In particular, the alkyl 2-hydroxy benzoate of the general formula XIIIa is treated with an inorganic base, such as cesium carbonate, and the double protected bromo substituted linker L5-1 in a polar solvent, such as DMF, at room temperature, to afford the intermediate of formula XIVa-1. Reduction of the carboxylic ester can be effected by treatment with a metal hydride reagent, such as lithium aluminium hydride, in a polar solvent, such as THF, at room temperature, to afford the benzyl alcohol of formula A3-1.

-continued

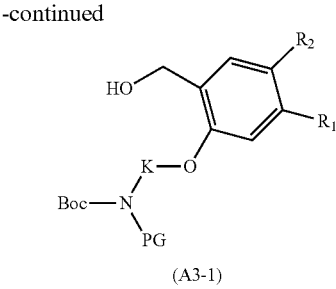

(A3-1)

PG = 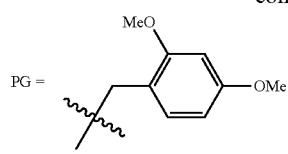

The linker of formula L5-1 can be prepared in three steps from an amino alcohol L5-2 (scheme 13). Reductive amination of L5-2 in the presence of 2,4-dimethoxy benzaldehyde can be effected with a metal hydride, such as sodium borohydride, and a carboxylic acid, such as acetic acid, in a protic organic solvent, such as methanol. This transformation takes place between −10° C. and 20° C., to afford the mono protected amino alcohol of formula L5-3. Boc protection is carried out under art-known conditions, as described hereinbefore for scheme 5d, to afford the double amine protected amino alcohol of formula L5-4. Transformation of the alcohol into a bromine is effected by tetracarbon bromide in the presence of triphenyl phosphine, as described hereinbefore for scheme 11b, to afford the double protected amino bromo alkane of formula L5-1.

Scheme 13

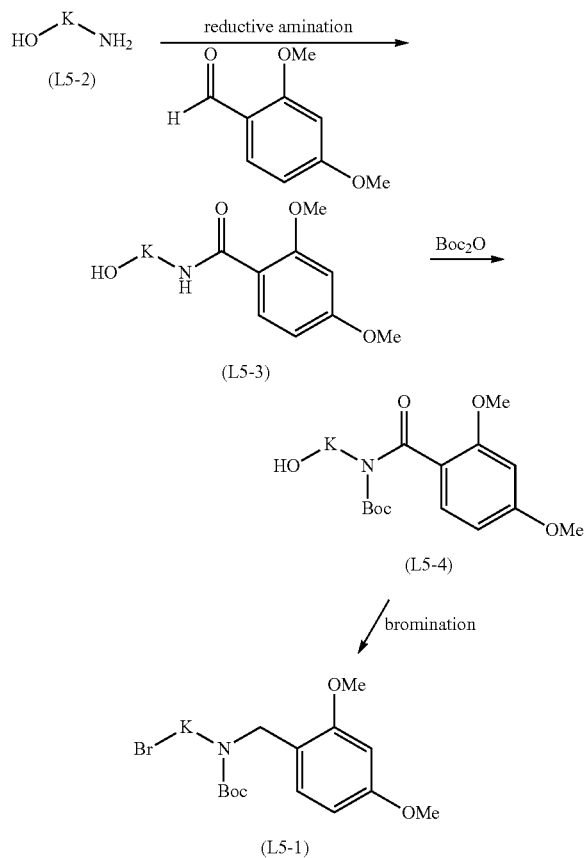

The Boc-amino functionalized linker of the general formula L1 can be prepared from the amino sulfonamide of the general formula L1-1 (scheme 14). Typically, a solution of the amine L1-1 in a chlorinated hydrocarbon solvent, such as DCM, is treated with Boc$_2$O, at room temperature.

Scheme 14

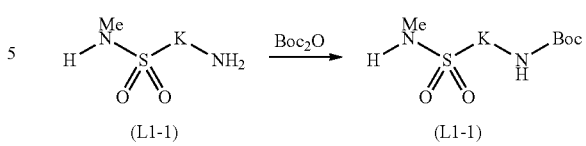

The amino functionalized linker of the general formula L1-1 can be prepared in different ways, depending on the nature of K. For example, when K is $C_{3-4}$alkyl, leading to the linker of the formula L1-1a, the sequence as depicted in Scheme 15a can be followed. The chloro sulfonamide L1-2 is first treated with sodium iodide, in a polar, aprotic solvent, such as DMF, at room temperature. Next, sodium azide is added and the mixture is allowed to react in a temperature range between 20 and 70° C., in particular at 60° C., to afford the azide L1-3. In a next step, the azide is reduced to afford the amine L1-1a. This transformation can be effected by putting the azide L1-3 under a hydrogen atmosphere, typically at 1 atm., in a protic organic solvent, such as methanol. The use of a catalyst, such as palladium on carbon, is essential to effect said hydrogenation reaction.

Scheme 15a

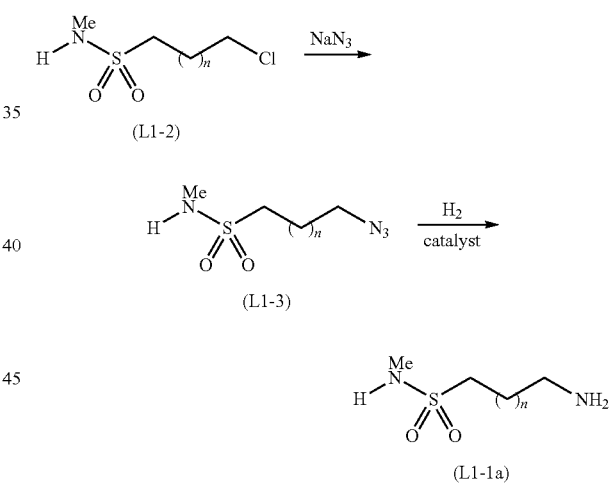

n = 1,2

In another example, when K is pentylene, leading to the linker of the formula L1-1b, the method illustrated by Scheme 15b can be followed. The chloro sulfonamide L1-2a, is first treated with sodium iodide, in a polar, aprotic solvent, such as DMF, at room temperature. Next, sodium cyanide is added and the mixture is allowed to react in a temperature range between about 20 and about 70° C., in particular at about 60° C., to afford the nitrile L1-4. In a next step, the nitrile is reduced to afford the amine L1-1b. This transformation can for example be effected by treatment of L1-4 with borane dimethylsulfide complex at room temperature, in a polar aprotic solvent, such as THF, to afford the primary amine L1-1b.

Scheme 15b

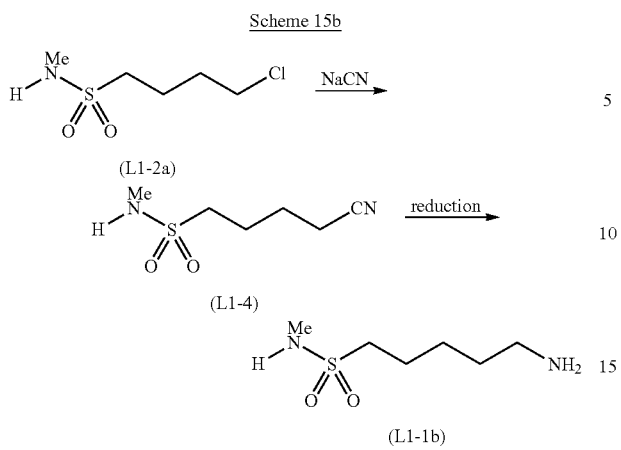

The linker precursors of the general formula L2 can be prepared by different methods. An oxidation reaction of the primary hydroxyl function in L5-4 can be employed (scheme 16a). In particular, said oxidation is effected under Swern conditions, which involves reaction between oxalyl chloride and DMSO in an halogenated solvent, such as DCM, at a temperature range between about −60° C. and about −70° C., followed by addition of the alcohol of general formula L5-4, and a tertiary amine, such as triethyl amine, in the same temperature range, to afford the aldehyde of formula L2-1.

Scheme 16a

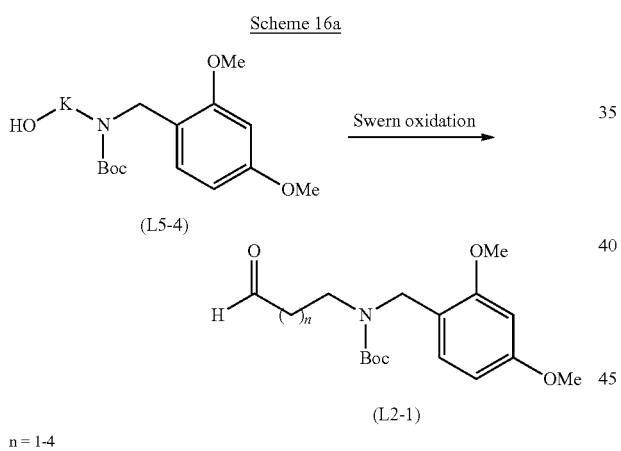

n = 1-4

Alternatively, the procedure illustrated by scheme 16b can be followed. In a first step the Boc protected ω-amino alcohol of formula L2-2a is protected with a silyl group, such as tert butyl dimethylsilyl, by reacting the alcohol L2-2a with tert butyldimethyl chlorosilane, in the presence of an amine base, such as imidazole, in an halogenated solvent, such as DCM, at a temperature between 0° C. and 25° C. Next the Boc protected amine is alkylated to introduce the R5 substituent, by treatment with a strong inorganic base, such as sodium hydride, and R5-X (whereby X=bromo, or iodo), in a polar, aprotic solvent, such as THF, at a temperature between 0° C. and 20° C., to afford the silyl protected alcohol of formula L2-2c. Deprotection of the silyl group, by treatment with a fluoride reagent, such as TBAF, in a polar solvent, such as THF, between 0° C. and 20° C., affords the alcohol of formula L2-2d. Swern oxidation, similarly as described hereinbefore for scheme 16a yields the aldehyde of the general formula L2-2.

Scheme 16b

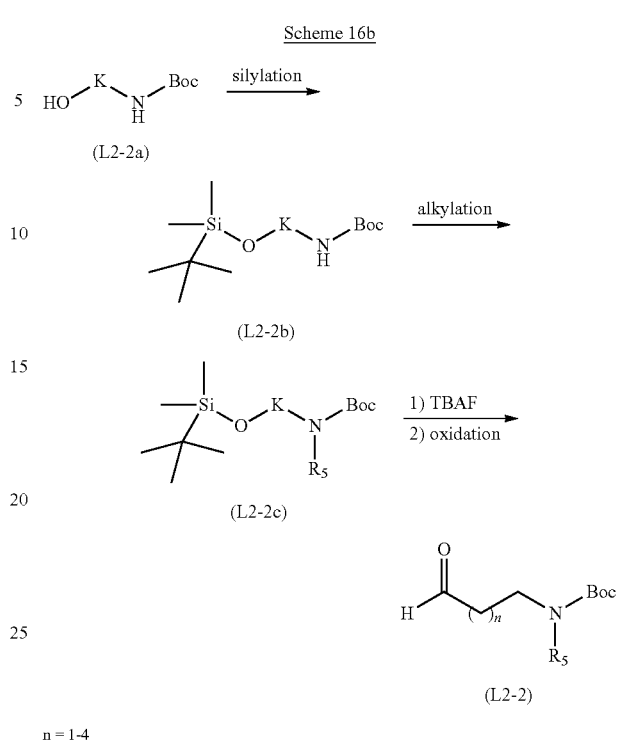

n = 1-4

The alkanoyl protected hydroxy functionalized linker of the general formula L3 can be prepared from an alkanoyl protected halo alkanol of the general formula L3-1, as is depicted in scheme 17. In a first step the halo carboxylic ester of the general formula L3-1 is converted into the corresponding (amino iminomethyl)thio ether of the formula L3-2. This transformation is effected by heating a mixture of thiourea and the halo carboxylic ester L3-2 in an organic protic solvent, such as ethanol or the like, at a temperature between about 70 and 100° C. In a second step the sulfonyl chloride of the general formula L3-3 is prepared by treating the (amino iminomethyl)thio ether of the formula L3-2 with chlorine in water as the solvent at a temperature of about 0° C. In a third step the sulfonyl chloride of the general formula L3-3 is converted into the corresponding alkyl or cycloalkyl sulfonamide of the general formula L3, by treating a mixture of the sulfonyl chloride L3-3, with a primary amine $R_5$—$NH_2$ in a biphasic solvent system consisting of water and a halogenated hydrocarbon, such as DCM. Said transformation is optionally carried out in the presence of an inorganic base, such as potassium carbonate, at a temperature between about 0 and about 20° C.

Scheme 17

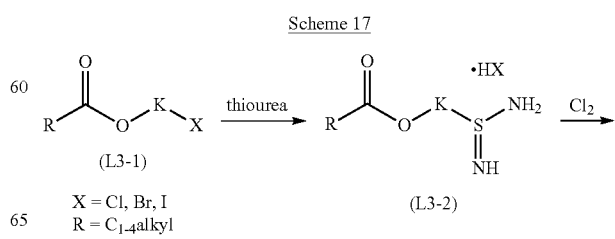

X = Cl, Br, I
R = $C_{1-4}$alkyl

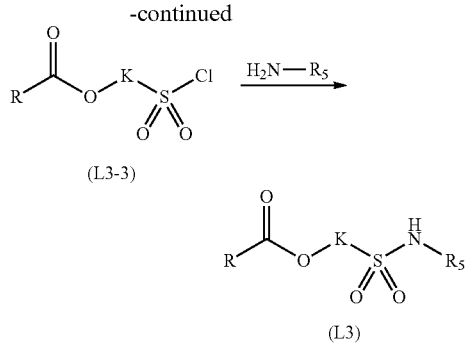

(L3-3)

(L3)

The compounds of formula I show antiretroviral properties (integrase inhibiting properties), in particular against HIV, the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever-decreasing number of T-4 cells, which moreover behave abnormally. Hence, the immunological defense system is unable to combat infections and neoplasms and the HIV infected subject usually dies by opportunistic infections such as pneumonia, or by cancers.

The compounds of the invention also show activity against drug- and multidrug-resistant HIV strains, in particular against HIV strains that have acquired resistance to one or more of the HIV integrase inhibitors used in the clinic, in particular to raltegravir and/or elvitegravir. Major primary resistance mutations associated with raltegravir treatment include N155H and Q148K/R/H. Raltegravir treatment failure is further associated with integrase mutations in at least 3 distinct genetic pathways defined by 2 or more mutations including a signature (or major) mutation being one of the primary mutations at Q148H/K/R, N155H, or Y143R/H/C, and, one or more additional minor mutations. Minor mutations described in the Q148H/K/R pathway include L74M plus E138A, E138K, or G140S. The most common mutational pattern in this pathway is Q148H plus G140S, which also confers the greatest loss of drug susceptibility (V. A. Johnson et al. (2009) Topics in HIV Medicine 17(5), 138-145). As illustrated by the examples below, compounds of formula I or subgroups thereof have advantageous therapeutic or prophylactic properties due to their antiviral properties with respect to wild type HIV, as well as single and double mutant HIV strains associated with resistance against raltegravir and/or elvitegravir.

Due to their antiretroviral properties, particularly their anti-HIV properties, the compounds of formula I or any subgroup thereof, the pharmaceutically acceptable addition salts thereof, and the stereoisomeric forms thereof, are useful in the treatment of individuals infected by HIV and for the prophylaxis of these infections. The compounds of the present invention may also find use in the treatment of warm-blooded animals infected with viruses whose existence is mediated by, or depends upon, the enzyme protease. Conditions that may be prevented or treated with the compounds of the present invention, especially conditions associated with HIV, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the compounds of formula I may be used in the manufacture of a medicament for the treatment or the prevention of HIV infections.

In a further aspect this invention provides a method of treating humans, suffering from, or a method of preventing humans to suffer from viral infections, especially HIV infections. Said method comprises the administration of an effective amount of a compound of formula I, a pharmaceutically acceptable addition salt, a pharmaceutically acceptable solvate thereof, or a possible stereoisomeric form thereof, to humans.

The present invention also provides compositions for treating viral infections comprising a therapeutically effective amount of a compound of formula I and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared wherein the carrier comprises a saline solution, a glucose solution, or a mixture of saline and glucose solution. Injectable suspensions may also be prepared in which case appropriate liquid carriers, suspending agents and the like may be employed. Also included are solid form preparations that can be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula I used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

As illustrated by the examples, compounds of formula I or subgroups thereof have advantageous therapeutic or prophylactic properties due to their pharmacokinetic properties such as high metabolic stability correlated with low plasma clearance as demonstrated in rat. In particular, compounds of formula I or subgroups thereof may have favourable therapeutic or prophylactic properties due to the combination of their antiviral and pharmacokinetic properties compared to compounds known in the art.

Also, the combination of one or more additional antiretroviral compounds and a compound of formula I can be used as a medicine. Thus, in a further aspect, the present invention also relates to a product containing (a) a compound of formula I, and (b) one or more additional antiretroviral compounds, as a combined preparation for simultaneous, separate or sequential use in anti-HIV treatment. The different drugs may be combined in separate preparations or in a single preparation, together with pharmaceutically acceptable carriers. Said other antiretroviral compounds may be any known antiretroviral compounds such as nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), amdoxovir (DAPD), elvucitabine (ACH-126,443), apricitabine (AVX 754, (−)-dOTC), fozalvudine tidoxil (FZT, HDP-990003), phosphazide, KP-1461, racivir (PSI-5004), MIV-210, and GS-9131; non-nucleoside reverse transcriptase inhibitors (NNRTIs) such as delavirdine (DLV), efavirenz (EFV), nevirapine (NVP), dapivirine (TMC120), etravirine (ETR, TMC125), rilpivirine (TMC278), IDX899, RDEA-806, UK-453601, RDEA-427, and UC-781; nucleotide reverse transcriptase inhibitors (NtRTIs), e.g. tenofovir and its pro-drug tenofovir disoproxil fumarate (TDF); protease inhibitors, e.g. ritonavir (RTV), saquinavir (SQV), lopinavir (ABT-378, LPV), indinavir (IDV), amprenavir (VX-478), nelfinavir (AG-1343), atazanavir (BMS 232,632), darunavir (TMC114), fosamprenavir (GW433908 or VX-175), brecanavir (GW-640385, VX-385), tipranavir (PNU-140690), DG-17, SPI256, PPL-100 (MK 8122), and TMC310911; entry inhibitors, which comprise fusion inhibitors (e.g. enfuvirtide (T-20) sifuvirtide, HRG-214, albuvirtide, SUC-HAS, and maC46/M87o), attachment inhibitors, modulators of intracellular cholesterol and corticosteroid biosynthesis (e.g. SP-01A), and co-receptor inhibitors, the latter comprise the CCR5 antagonists (e.g. CCR5 mAb004, maraviroc (UK-427,857), PRO-140, TAK-220, TAK-652, PF232798, vicriviroc (SCH-D, SCH-417, 690), GSK-706769, nifeviroc, and SCH-532706) and CXR4 antagonists (e.g. AMD-070), further examples of entry inhibitors are TNX-355, NCB 9471, BMS-488043, nonakine, and VGV-1; maturation inhibitors, e.g. bevirimat (PA-457) and vivecon; and inhibitors of the viral integrase, e.g. raltegravir (MK-0518), elvitegravir (JTK-303, GS-9137), BMS-538158, S-349572, JTK-656 S-247303, GS-265744, and S/GSK-1349572.

The following examples are intended to illustrate the present invention and not to limit its scope thereto.

EXAMPLES

A. Chemical Synthesis of Compounds of Formula I

Example 1

Intermediate I-2

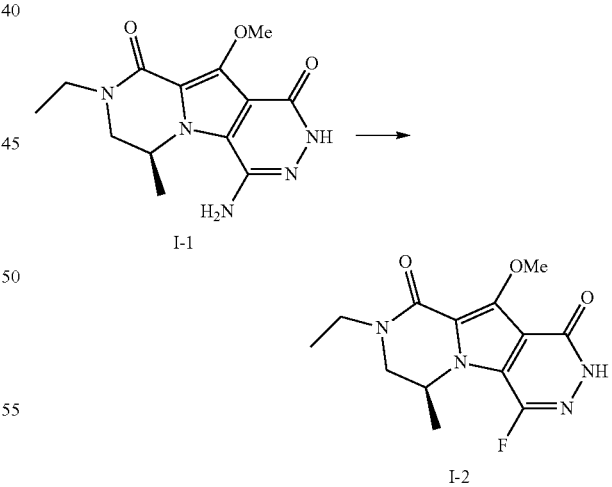

Three parallel reactions were set up and the crude reaction mixtures were combined for work-up. Each reaction was carried out by using one third of the quantities described below.

Tricyclic amine I-1 (0.62 mol) was dissolved in HF/pyridine (450 ml) at 25° C. NaNO$_2$ (0.93 mol) was added portionwise at 0° C. The mixture was stirred overnight at 25° C. The mixture was added dropwise to saturated NaHCO$_3$ solution and then it was extracted with CH$_2$Cl$_2$ (3×1000 ml). The combined organic layers were washed with brine and dried over Na$_2$SO$_4$. The solvent was removed under vacuum. The ensuing solid was washed with CH$_2$Cl$_2$. Yield: 90 g of Intermediate I-2 (50% yield).

Example 2

(S)-ethyl 6-cyano-2-isopropyl-8-methoxy-4-methyl-1-oxo-1,2,3,4-tetrahydropyrrolo[1,2-a]pyrazine-7-carboxylate (I-3)

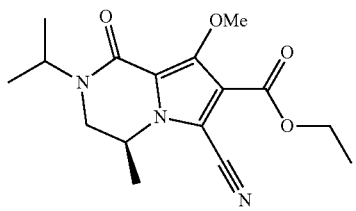

I-3

Three parallel reactions were set up and the crude reaction mixture was combined for work-up. Each reaction was carried out by using one third of the quantities described below.

(S)-ethyl 6-bromo-2-isopropyl-8-methoxy-4-methyl-1-oxo-1,2,3,4-tetrahydro-pyrrolo[1,2-a]pyrazine-7-carboxylate (1.2 mol) and Cu(I)CN (2.4 mol) were dissolved in dimethylformamide (DMF; 2.2 l) at 20° C. under N$_2$. The mixture was stirred for 2 h at 110° C. Concentrated NH$_3$.H$_2$O (650 ml) was added at 60° C. The mixture was stirred for 30 min at 60° C. and then cooled to 20° C. The mixture was filtered off. Ethyl acetate (3000 ml) and H$_2$O (2000 ml) were added and the organic layer was separated. The aqueous layer was extracted with ethyl acetate (3×1000 ml). The combined organic layers were washed with brine, dried and concentrated in vacuo. The crude product and a small batch of an earlier preparation were combined and washed with methyl tert-butyl ether to give a solid. Yield: 350 g of Intermediate I-3 (95% purity, 80% yield total).

Example 3

Intermediate I-4

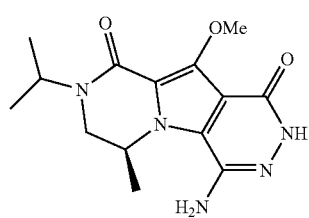

I-4

Intermediate I-3 (1.1 mol) and hydrazine hydrate (11 mol) in tert-butyl alcohol (2.7 l) was refluxed for 18 h. The mixture was concentrated in vacuo. The resulting residue was purified by column chromatography (gradient eluent: CH$_2$Cl$_2$ then CH$_2$Cl$_2$/methanol 50:1 to 30:1 to 20:1) to afford the desired compound. Yield: 220 g (66% yield)

Example 4

Intermediate I-5

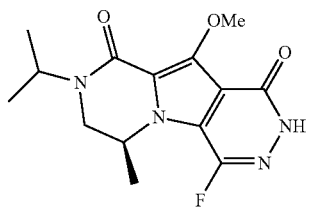

I-5

Intermediate I-5 was prepared from Intermediate I-4 in an analogous way as described in Example 1.

Example 5

(S)-Benzyl 1-(cyclopropylamino)propan-2-ylcarbamate (I-6)

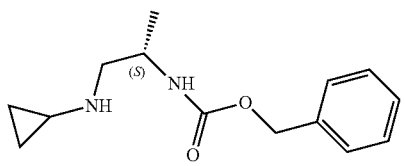

I-6

(S)-2-(Benzyloxycarbonylamino)propyl methanesulfonate (48 mmol) and cyclopropyl amine (480 mmol) were mixed together and stirred at room temperature for 48 h. The remaining cyclopropyl amine was removed by rotary evaporator and the residual mixture was added to 500 ml of ethyl acetate and washed with 5% Na$_2$CO$_3$ aqueous solution and brine. After drying (K$_2$CO$_3$) and removal of the solvent, the residual semi-solid was recrystallized from CH$_2$Cl$_2$ and petroleum ether to afford the target compound in 60% yield.

Example 6

(S)-Benzyl 1-(2-bromo-N-cyclopropylacetamido)propan-2-ylcarbamate (I-7)

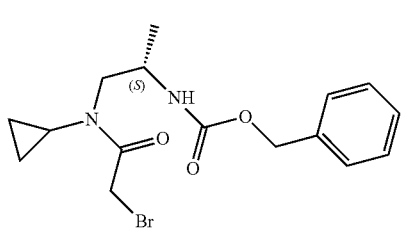

I-7

Intermediate I-6 (0.26 mol) was added to mixture of ethyl acetate (530 ml) and saturated aqueous NaHCO$_3$ (322 ml) which was then cooled to 0° C. Then bromoacetyl bromide (0.29 mol) was added dropwise under an atmosphere of N₂. After stirring at room temperature for 1 h, the layers were separated and the aqueous phase was extracted with ethyl acetate. The combined organic phases were washed with brine and dried over anhydrous sodium sulfate. After filtration and concentration, the target compound was obtained in 90% yield.

Example 7

(S)-Benzyl 4-cyclopropyl-2-methyl-5-oxopiperazine-1-carboxylate (I-8)

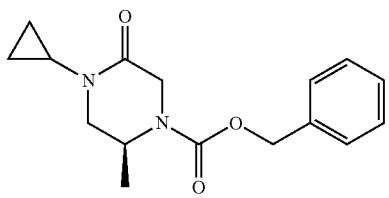

I-8

Intermediate I-7 (40 mmol) was dissolved in 90 ml of anhydrous tetrahydrofuran (THF; 690 ml), to which was added portion wise 60% NaH (44 mmol). The resulting mixture was stirred at room temperature for 2 h, and quenched with citric acid. The mixture was concentrated to dryness and the residue was partitioned between CH₂Cl₂ and a saturated NaHCO₃ solution. After drying (Na₂SO₄) and concentration, the residue was purified by column chromatography over silica gel eluting with 1% to 6% methanol in chloroform to give the target compound as a white solid in 70% yield.

Example 8

(S)-1-Cyclopropyl-5-methylpiperazin-2-one, hydrochloride (I-9)

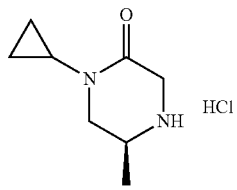

I-9

Intermediate I-8 (17.4 mmol) was dissolved methanol (50 ml), and 0.5 g (10%, 0.5 mmol) of Pd/C was added. The reaction was stirred under H₂ atmosphere provided by a H₂ balloon. After 18 h, the mixture was filtered over a bed of celite and washed with methanol. After concentration the crude product was dissolved in diethyl ether, and 1.5 ml of 4 N HCl in diethyl ether was added. Then a white suspension was obtained. After stirring overnight, the suspension was filtered and the solid was washed with diethyl ether to obtain the target compound as a white solid (Yield 70%).

Example 9

(S)-Diethyl 2-((4-cyclopropyl-2-methyl-5-oxopiperazin-1-yl)methylene)malonate (I-10)

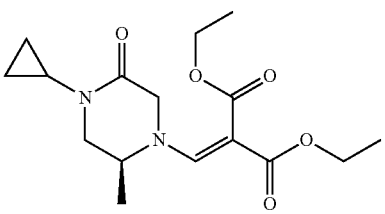

I-10

Intermediate I-9 (169 mmol) was suspended in ethyl acetate (300 ml). A saturated K₂CO₃ solution (30 ml) was added. The organic layer was washed with brine and dried (Na₂SO₄). The solvent was removed under vacuum. The resulting residue and diethyl ethoxymethylenemalonate (169 mmol) were dissolved in toluene (260 ml). The mixture was stirred at 25° C. for 0.5 h, and then at 120° C. for 0.5 h. The mixture was evaporated under vacuum. The residue was purified with column chromatography over silica gel (eluent: CH₂Cl₂ then ethyl acetate). The ethyl acetate fractions were collected and evaporated. Yield: 60 g (purity 62%; 80% yield).

Example 10

(S)-Ethyl 2-cyclopropyl-8-hydroxy-4-methyl-1-oxo-1,2,3,4-tetrahydro-pyrrolo[1,2-a]pyrazine-7-carboxylate (I-11)

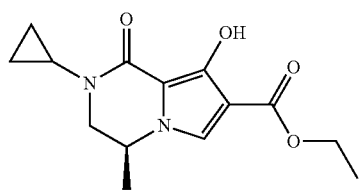

I-11

Intermediate I-10 (135 mmol, 80% pure) was dissolved in dry THF (500 ml) at 20° C. A solution of lithium hexamethyl disilazide (1 M in THF, 148 mmol) was added dropwise keeping the temperature below −70° C. The mixture was allowed to warm to 20° C. and was then quenched by aqueous NH₄Cl. The mixture was evaporated under vacuum. CH₂Cl₂ and 1 N HCl were added. The organic layer was washed by brine and dried (MgSO₄). The solvent was removed under vacuum. The residue was purified by SiO₂ column chromatography (eluent: petroleum ether/ethyl acetate 1:1). Yield: 17.7 g (purity 90%, 47% yield).

Example 11

(S)-ethyl 2-cyclopropyl-8-methoxy-4-methyl-1-oxo-1,2,3,4-tetrahydro-pyrrolo[1,2-a]pyrazine-7-carboxylate (I-12)

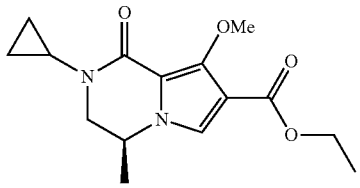

I-12

Intermediate I-11 (64 mmol) was dissolved in DMF (180 ml) at 20° C. K$_2$CO$_3$ (254 mmol) was added. Methyl iodide (76 mmol) was added dropwise at 0° C. The mixture was stirred overnight at 20° C. Then, the mixture was filtered off and the filtrate was diluted with brine and CH$_2$Cl$_2$. The organic layer was collected and washed by brine. The solvent was dried (MgSO$_4$) and then evaporated. Yield: 16 g (purity 90%; 86% yield).

Example 12

(S)-ethyl 6-bromo-2-cyclopropyl-8-methoxy-4-methyl-1-oxo-1,2,3,4-tetrahydropyrrolo[1,2-a]pyrazine-7-carboxylate (I-13)

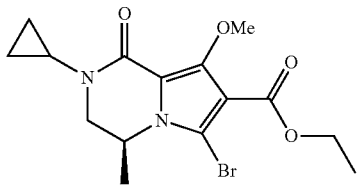

I-13

Intermediate I-12 (55 mmol) was dissolved in dichloroethane (200 ml). N-Bromosuccinimide (NBS; 60 mmol) was added to the mixture at 0° C. and the mixture was stirred at 25° C. for 3 h. A saturated Na$_2$S$_2$O$_3$ solution (100 ml) was added and the mixture was stirred for 5 min. CH$_2$Cl$_2$ (200 ml) and a 0.5 N NaOH solution (100 ml) were added. The organic layer was washed with brine and dried (Na$_2$SO$_4$). The solvent was removed under vacuum. The residue was purified by SiO$_2$ column chromatography (eluent: petroleum ether/ethyl acetate 1:3). Yield: 11 g (purity 90%, 54% yield).

Example 13

(S)-ethyl 6-(2-ethoxy-2-oxoacetyl)-2-ethyl-8-methoxy-4-methyl-1-oxo-1,2,3,4-tetrahydropyrrolo[1,2-a]pyrazine-7-carboxylate (I-14)

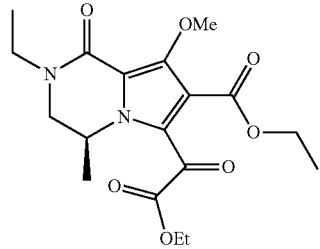

I-14

(S)-Ethyl 6-bromo-2-ethyl-8-methoxy-4-methyl-1-oxo-1,2,3,4-tetrahydropyrrolo[1,2-a]pyrazine-7-carboxylate (0.70 mol) was dissolved in THF (4500 ml) at 20° C. Molecular sieves (4 Å; 250 g) were added. The mixture was stirred for 30 min at 20° C., and was then cooled to −78° C. A solution of n-Butyllithium (2.5 M; 0.77 mol) was added dropwise below −65° C. The mixture was stirred for 1 h at −78° C. Diethyl oxalate (1.6 mol) in THF (600 ml) was added dropwise below −65° C. and then it was stirred for 3 h. The mixture was poured into a solution of aqueous H$_2$SO$_4$ (4200 ml, 2 M) and THF (3500 ml). The organic layer was separated and the aqueous layer was re-extracted with ethyl acetate (3×2000 ml). The combined organic layers were collected and evaporated. The residue was purified by column chromatography over silica gel (eluent: petroleum ether/ethyl acetate from 100:0 to 1:1). The pure fractions were collected and the organic solvent was evaporated. Yield: 170 g (67% yield).

Example 14

Intermediate I-15

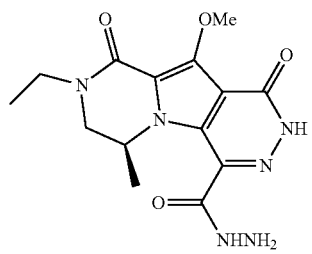

I-15

Intermediate I-14 (0.46 mol) was dissolved in methanol (2 l) at 20° C. A solution of hydrazine in THF (1 M; 2.8 mol) was added at 10° C. The mixture was stirred for 2 h at 20° C. The solvent was removed under vacuum and the resulting residue was used for the next step without purification. Yield: 180 g crude Intermediate I-15 (86% purity).

Example 15

Intermediate I-16

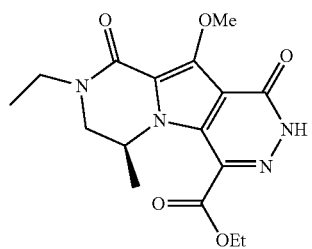

I-16

Crude Intermediate I-15 (0.46 mol) was dissolved in dry ethanol (3.5 l) at 20° C. NBS (1.2 mol) was added portionwise keeping the temperature below 30° C. The mixture was stirred overnight at 25° C. The solvent was removed under vacuum and CH$_2$Cl$_2$ was added. The mixture was quenched with 10% aqueous Na$_2$SO$_3$ and then washed with 10% K$_2$CO$_3$ to remove the succinimide. The organic layer was concentrated to dryness. The residue was purified with silica gel chromatography (CH$_2$Cl$_2$/methanol 100:0 to 10:1). The pure fractions were collected and the volatiles were removed under vacuum. The crude compound was washed with tert-butyl methyl ether. Yield: 100 g (62% yield for two steps).

Example 16

Intermediate I-17

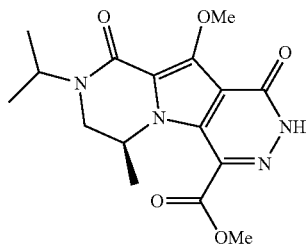

Intermediate I-17 was prepared from (S)-ethyl 6-bromo-2-isopropyl-8-methoxy-4-methyl-1-oxo-1,2,3,4-tetrahydropyrrolo[1,2-a]pyrazine-7-carboxylate analogously to Examples 13-15.

Example 17

Intermediate I-18

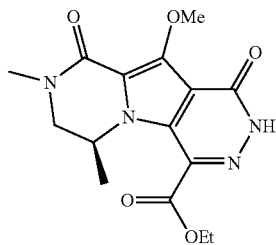

Intermediate I-18 was prepared from (S)-ethyl 6-bromo-8-methoxy-2,4-dimethyl-1-oxo-1,2,3,4-tetrahydropyrrolo[1,2-a]pyrazine-7-carboxylate analogously to Examples 13-15.

Example 18

Diethyl 1-(2-(tert-butoxycarbonylamino)ethyl)-3-methoxy-1H-pyrrole-2,4-dicarboxylate (I-19)

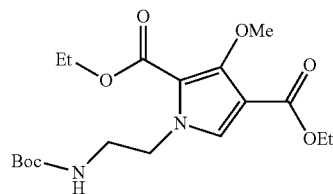

To a solution of diethyl 3-methoxy-1H-pyrrole-2,4-dicarboxylate (93 mmol) in DMF (340 ml) was added 60% NaH (140 mmol) in portions at 0° C. and the reaction mixture was stirred at 25° C. for 0.5 h. 2,2-Dioxo-[1,2,3]oxathiazolidine-3-carboxylic acid tert-butyl ester (93 mmol) was added at 0° C. and the mixture was allowed to warm to 25° C. and stirred for 21 h. The reaction was quenched with ethanol at 0° C. The solvent was evaporated under vacuum. Yield: 35 g (98% yield)

Example 19

Diethyl 1-(2-aminoethyl)-3-methoxy-1H-pyrrole-2,4-dicarboxylate, hydrochloride (I-20)

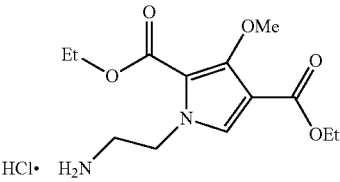

A solution of Intermediate I-19 (91 mmol) in 4N HCl in dioxane (350 ml) was stirred at 60° C.-70° C. for 1 h. The solvent was evaporated under vacuum, and used as such in the next step. Yield: 28.8 g (99% yield)

Example 20

Ethyl 8-methoxy-1-oxo-1,2,3,4-tetrahydropyrrolo[1,2-a]pyrazine-7-carboxylate (I-21)

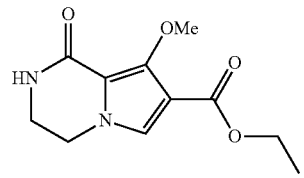

A mixture of Intermediate I-20 (90 mmol), $K_2CO_3$ (463 mmol) in ethanol (450 ml) was refluxed for 19 h. The solvent was evaporated under vacuum and ethyl acetate was added to the resulting residue. The mixture was filtered off. The filtrate was evaporated under vacuum and $CH_2Cl_2$ was added to the residue. The resulting organic layer was washed with brine and evaporated under vacuum. The residue was purified with flash column (eluent: $CH_2Cl_2$, then ethyl acetate). The pure portion was collected and evaporated under vacuum. The residue was washed with tert-butyl methyl ether to afford the desired product. Yield: 12.7 g (59% yield).

Example 21

Ethyl 2-ethyl-8-methoxy-1-oxo-1,2,3,4-tetrahydropyrrolo[1,2-a]pyrazine-7-carboxylate (I-22)

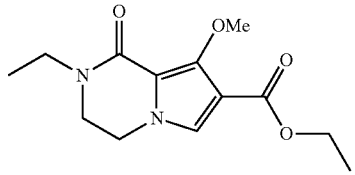

To a solution of Intermediate I-21 (53 mmol) in DMF (400 ml) was added 60% NaH (80 mmol) in portions at 0° C. and the reaction mixture was stirred at 25° C. for 40 min. Iodo ethane (80 mmol) was added at 0° C. and the reaction mixture was stirred at 25° C. for 20 h. The reaction mixture was quenched with ethanol and then by water at 0° C. $CH_2Cl_2$ was added. The organic layer was separated and washed with brine, and dried over $Na_2SO_4$. Yield: 14 g (98% yield)

Example 22

Intermediate I-23

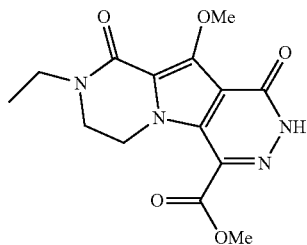

I-23

Intermediate I-23 was prepared from Intermediate I-22 analogously to Examples 12-15.

Example 23

Intermediate I-24

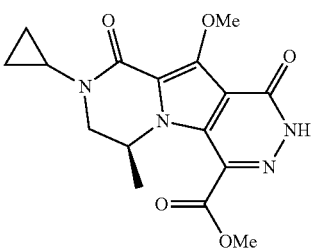

I-24

Intermediate I-24 was prepared from Intermediate I-13 analogously to Examples 13-15.

Example 24

Methyl 2-(5-(tert-butoxycarbonylamino)pentyloxy)-4-fluorobenzoate (I-25)

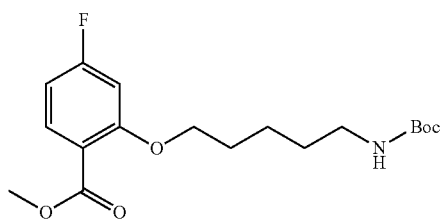

I-25

The reaction was carried out under $N_2$ atmosphere. Triphenyl phosphine (0.52 mol) was added to a solution of methyl 4-fluoro-2-hydroxybenzoate (0.47 mol), tert-butyl 5-hydroxypentylcarbamate (0.47 mol) and diisopropyl azodicarboxylate (DIAD; 0.94 mol) in THF (1 l) dropwise at −20° C. The reaction mixture was allowed to warm to room temperature and stirred at room temperature for 2 h. The resulting mixture was used directly in the next step without further purification.

Example 25

2-(5-(tert-Butoxycarbonylamino)pentyloxy)-4-fluorobenzoic acid (I-26)

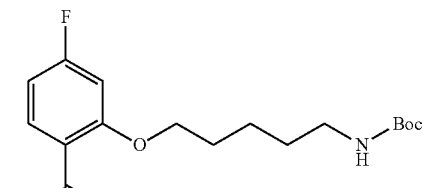

I-26

Methanol (500 ml) and water (500 ml) were added to the crude reaction mixture obtained in Example 24. LiOH hydrate (1.4 mol) was added and the reaction mixture was stirred at room temperature for 16 h. Then, water (500 ml) was added and the organic solvent was evaporated under vacuum. The mixture was extracted with methyl tert-butyl ether to remove impurities. The water layer was adjusted to pH 8-9 and extracted again with ethyl acetate (3×500 ml). The water layer was adjusted to pH 4-5 and ethyl acetate was added. The organic layer was separated, washed with brine, dried and concentrated in vacuo. Yield: 120 g (purity 80%, 75% yield over 2 steps).

Example 26 tert-Butyl 5-(5-fluoro-2-(hydroxymethyl)phenoxy)pentylcarbamate (I-27)

I-27

Intermediate I-26 (0.43 mol) was dissolved in THF (1 l). Borane-$Me_2S$ complex (0.55 mol) was added dropwise to the solution at 0° C. The reaction mixture was stirred at room temperature for 6 h. Methanol (500 ml) was added dropwise to the mixture at 0° C. The organic solvent was evaporated and the residue was purified by $SiO_2$ flash column chromatography (petroleum ether/ethyl acetate 100:0 to 2:1). Yield: 80 g (purity 80%, yield 57%).

Example 27

Methyl 2-(4-(tert-butoxycarbonylamino)butoxy)-4-fluorobenzoate (I-28)

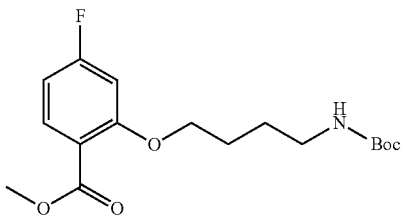

Methyl 4-fluoro-2-hydroxybenzoate (21 mmol), tert-butyl 4-hydroxybutylcarbamate (21 mmol) and triphenyl phosphine (24 mmol) in THF (70 ml) was cooled to −10° C. Then, DIAD (43 mmol) was added. The mixture was stirred for 30 min at −10° C. under $N_2$. The ice-bath was removed and the mixture was stirred overnight at 20° C. The solvent was removed under vacuum. The residue was washed with petroleum and diethyl ether. The white solid was filtered and it was confirmed to be triphenylphosphine oxide ($PPh_3$=O). The filtrate was evaporated to dryness. The residue was purified with flash column (petroleum/ethyl acetate 100:0 to 5:1). Yield: 8.18 g (purity 90%, yield 98%).

Example 28 tert-Butyl 4-(5-fluoro-2-(hydroxymethyl)phenoxy)butylcarbamate (I-29)

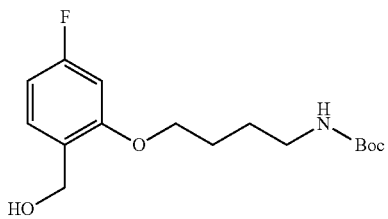

Intermediate I-28 (17 mmol) and $NaBH_4$ (188 mmol) were suspended in THF. The resulting mixture was stirred for 15 min at 65° C. Methanol (20 ml) was added dropwise during 0.5 h. Stirring at 65° C. was maintained overnight. Then, the reaction was cooled to 15° C., and quenched with saturated aqueous $NH_4Cl$ (120 ml). Stirring was continued for 1 h. Ethyl acetate (200 ml) was added and the organic layer was separated. The aqueous layer was extracted with ethyl acetate (2×200 ml). The organic layers were combined and dried over $Na_2SO_4$. The solvent was removed under vacuum to give a colorless oil. The residue was purified by $SiO_2$ flash column with eluent (petroleum/ethyl acetate 100:0 to 80:20). Yield: 3.1 g (purity 98%, 58% yield).

Example 29 tert-Butyl 5-(4-chloro-5-fluoro-2-(hydroxymethyl)phenoxy)pentylcarbamate (I-30)

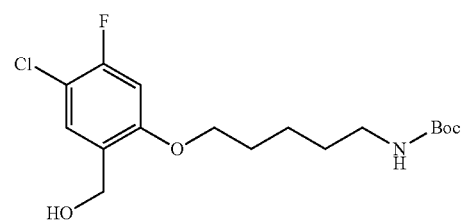

Intermediate I-30 was prepared from methyl 5-chloro-4-fluoro-2-hydroxybenzoate and tert-butyl 5-hydroxypentylcarbamate analogously to Examples 27-28.

Example 30 tert-Butyl 5-(4-chloro-2-(hydroxymethyl)phenoxy)pentylcarbamate (I-31)

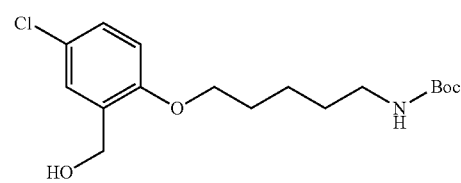

Intermediate I-31 was prepared from methyl 5-chloro-2-hydroxybenzoate and tert-butyl 5-hydroxypentylcarbamate analogously to Examples 24-26.

Example 31

5-(2,4-Dimethoxybenzylamino)pentan-1-ol (I-32)

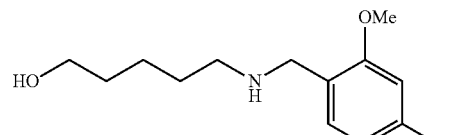

A solution of 5-aminopentan-1-ol (194 mmol), 2,4-dimethoxybenzaldehyde (213 mmol) and acetic acid (213 mmol) in methanol (500 ml) was stirred at 10° C. for 0.5 h. $NaBH_4$ (22 g) was added portionwise at −10° C. and the mixture was stirred for 10 minutes. Then the reaction mixture was allowed to warm to 10° C. and stirred for 1.5 h. Saturated $NaHCO_3$ was added and the mixture was stirred for 0.5 h. The mixture was extracted by $CH_2Cl_2$ (3×100 ml). The combined organic phase was washed by saturated brine, dried over $Na_2SO_4$, filtered and concentrated under reduced pressure to give a yellow oil. Yield: 46 g (69% purity, 65% yield).

Example 32 tert-Butyl 2,4-dimethoxybenzyl(5-hydroxypentyl)carbamate (I-33)

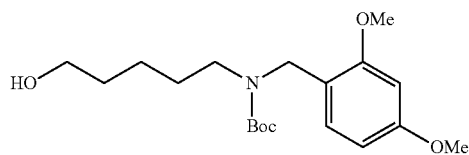

I-33

A solution of Intermediate I-32 (182 mmol) and Boc$_2$O (182 mmol) in methanol (1 l) was stirred at 10° C. overnight. The reaction mixture was evaporated in vacuo, the residue was purified by SiO$_2$ flash column (eluent: petroleum ether/ethyl acetate from 8:1 to 2:1) to give the pure Intermediate I-33. Yield: 43 g (95% purity, 67% yield).

Example 33 tert-Butyl 5-bromopentyl(2,4-dimethoxybenzyl)carbamate (I-34)

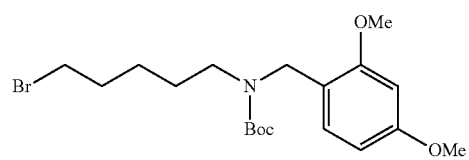

I-34

Triphenyl phosphine (37 mmol) was added to a mixture of Intermediate I-33 (28 mmol) in CH$_2$Cl$_2$ (200 ml) at 0° C. under N$_2$. Then CBr$_4$ (37 mmol) was added dropwise to the mixture at 0° C. The mixture was allowed to warm to 20° C. and stirred for 2 h. The mixture was evaporated to dryness and purified with SiO$_2$ flash column (eluent: petroleum ether/ethyl acetate from 20:1 to 10:1) to give the pure Intermediate I-34. Yield: 9.0 g (95% purity, 76% yield).

Example 34

Methyl 4,5-difluoro-2-hydroxybenzoate (I-35)

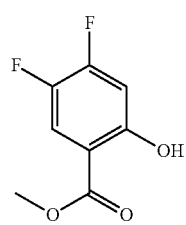

I-35

A mixture of 4,5-difluoro-2-hydroxybenzoic acid (20 mmol), methanol (100 ml) and concentrated H$_2$SO$_4$ (5 ml) was refluxed for 48 h. Then, the reaction mixture was concentrated. The residue was dissolved in ethyl acetate, washed with brine and a saturated NaHCO$_3$ solution and neutralized with citric acid. The organic layer was dried over MgSO$_4$ and concentrated in vacuo to give the product. Yield: 2.8 g (97% purity, 74% yield).

Example 35

Methyl 2-(5-(tert-butoxycarbonyl(2,4-dimethoxybenzyl)amino)pentyloxy)-4,5-difluorobenzoate (I-36)

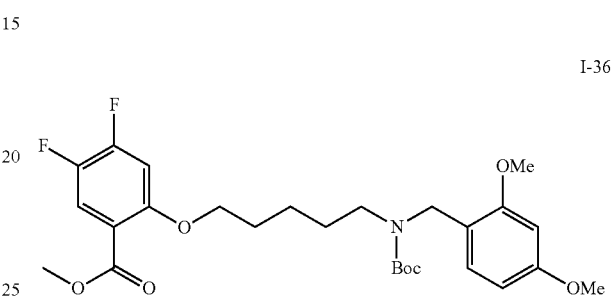

I-36

A mixture of Intermediate I-34 (11 mmol), Intermediate I-35 (11 mmol), and Cs$_2$CO$_3$ (34 mmol) in DMF (50 ml) was stirred at room temperature overnight. Then the mixture was diluted with CH$_2$Cl$_2$ and filtered. The filtrate was washed with brine, dried over Na$_2$SO$_4$, concentrated under vacuo. The residue was purified with silica gel column chromatography (eluent: petroleum ether/ethyl acetate from 16:1 to 8:1) to give the pure Intermediate I-36. Yield: 5.0 g (95% purity, 86% yield).

Example 36 tert-Butyl 5-((4,5-difluoro-2-hydroxymethyl)phenoxy)-pentyl-(2,4-dimethoxybenzyl)-carbamate (I-37)

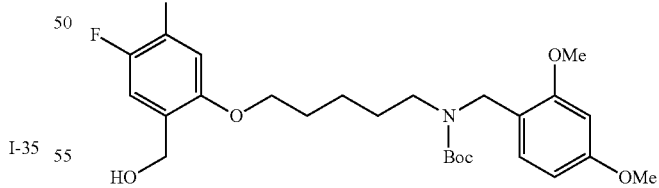

I-37

A mixture of Intermediate I-36 (9.5 mmol) and LiAlH$_4$ (38 mmol) in dry THF (100 ml) was stirred at room temperature for 4 h. The mixture was quenched with 0.8 ml 10% NaOH in water. The mixture was extracted with ethyl acetate. The organic layer was washed with brine, dried over Na$_2$SO$_4$. The solution was concentrated to give the crude Intermediate I-37. The residue was purified by flash column chromatography (eluent petroleum ether/ethyl acetate 2:1) to give the pure Intermediate I-37. Yield: 3.6 g (85% purity, 75% yield).

Example 37

Methyl 4-fluoro-2-(4-methoxybenzyloxy)benzoate (I-38)

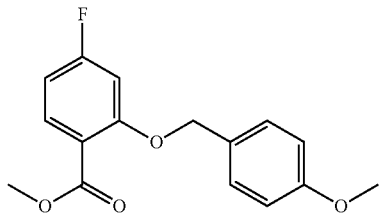

I-38

Methyl 4-fluoro-2-hydroxybenzoate (0.88 mol) was dissolved in $CH_3CN$ (1.5 l). Para methoxy benzylchloride (1.3 mol) and $K_2CO_3$ (2.2 mol) were added. The mixture was refluxed for 12 h. The mixture was filtered to remove the solid. The solvent was removed under vacuum. The resulting residue was purified by flash column chromatography (eluent: $CH_2Cl_2$). Yield 270 g (90% purity, 95% yield).

Example 38

(4-Fluoro-2-(4-methoxybenzyloxy)phenyl)methanol (I-39)

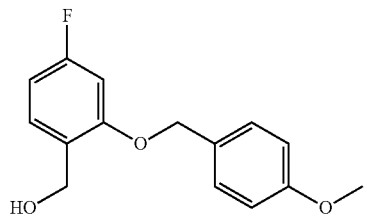

I-39

Intermediate I-38 (0.93 mol) and $NaBH_4$ (9.3 mol) were suspended in THF (4.1 l). The resulting mixture was stirred for 15 min at 65° C. Methanol (1.3 l) was added dropwise during 1.5 h and the mixture was stirred for 3 h at 65° C. The reaction was cooled to 15° C. and quenched with saturated aqueous $NH_4Cl$ (3500 ml). Then the mixture was stirred for 20 min. The organic layer was separated and the aqueous layer was extracted with ethyl acetate (3×1500 ml). The combined organic layers were washed with brine and dried over $Na_2SO_4$. The solvent was removed under vacuum. Yield 150 g (61% yield).

Example 39

Methyl 2-(allyloxy)-4-fluorobenzoate (I-40)

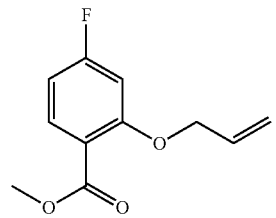

I-40

Methyl 4-fluoro-2-hydroxybenzoate (0.27 mol), $K_2CO_3$ (0.41 mol), and KI (27 mmol) were charged in a 1-l reactor under $N_2$. Acetone (500 ml) was added, followed by 3-bromopropene (0.33 mol). The mixture was refluxed for 6 h under $N_2$. The mixture was cooled to room temperature and filtered to remove the solid. The solvent was removed under vacuum, and the residue dissolved in water (200 ml) and $CH_2Cl_2$ (300 ml). The organic and aqueous layers were separated and the aqueous phase extracted with $CH_2Cl_2$. The organic layers were combined and dried with $Na_2SO_4$. The solvent was removed under vacuum to give Intermediate I-40 as a white solid.

Example 40

1-(Bromomethyl)-4-fluoro-2-(4-methoxybenzyloxy)benzene (I-41)

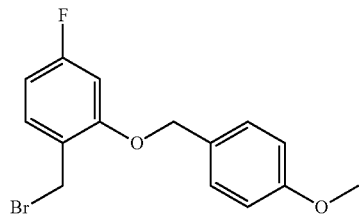

I-41

Triphenyl phosphine (30 mmol) and $CBr_4$ (30 mmol) were added to Intermediate I-39 (23 mmol) in $CH_2Cl_2$ (120 ml) at 0° C. and the reaction mixture was stirred at room temperature for 2 h. The reaction was purified by flash column chromatography (eluent: $CH_2Cl_2$) to give the pure product. Yield: 8.2 g (99% yield)

Example 41

(2-(Allyloxy)-4-fluorophenyl)methanol (I-42)

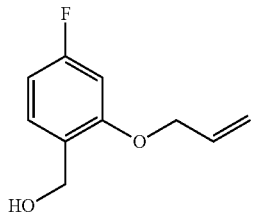

I-42

Intermediate I-40 (0.24 mol) and $NaBH_4$ (1.2 mol) were suspended in dimethoxyethane (DME, 350 ml) under $N_2$. The resulting mixture was stirred for 15 min at 65° C.-75° C. Methanol (175 ml) was added dropwise and the mixture was stirred for 14 h at 65° C. The reaction was cooled to 15° C. and quenched with saturated aqueous $NH_4Cl$ (150 ml). The mixture was extracted with ethyl acetate (400 ml). The organic layer was separated and the aqueous layer was extracted with ethyl acetate (2×200 ml). The combined organic layers were dried over $Na_2SO_4$. The solvent was removed under vacuum to give Intermediate I-42 as a white solid.

Example 42

4-(Carbamimidoylthio)butyl pivalate, hydrobromide (I-43)

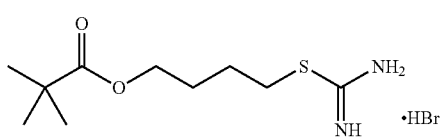

I-43

4-Bromobutyl pivalate (0.71 mol) and thiourea (0.78 mol) were dissolved in ethanol (330 ml) and the resulting mixture was refluxed for 1 h. The solvent was removed under vacuum. The resulting residue was used in the next step without further purification. Yield: 210 g (95% yield).

Example 43

4-(Chlorosulfonyl)butyl pivalate (I-44)

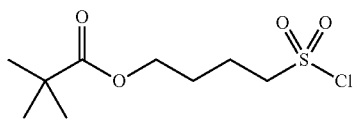

I-44

The crude Intermediate I-43 (0.38 mol) was dissolved in water (1.2 l). Ethyl acetate (200 ml) was added, and Cl₂ gas was bubbled into the ensuing mixture at 0° C. for 1 h, then N₂ was bubbled for 2 h. The mixture was extracted with ethyl acetate (2×800 ml). The organic layer was washed with 5% NaHSO₃ and brine and dried over Na₂SO₄. The solvent was removed under vacuum. Yield: 95 g (purity 90%, 97% yield).

Example 44

4-(N-methylsulfamoyl)butyl pivalate (I-45)

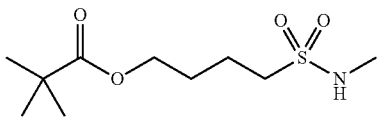

I-45

Intermediate I-44 (0.37 mol) and methyl amine HCl (1.5 mol) were suspended in CH₂Cl₂ (1.5 l) and cooled to 0° C. K₂CO₃ (1.5 mol) in water (750 ml) was added dropwise. The mixture was stirred at 20° C. for 2 h. The organic layer was washed with brine and dried (Na₂SO₄). The solvent was removed under vacuum. The residue was purified by SiO₂ column (eluent: petroleum ether/ethyl acetate 3:1). Yield: 65 g (90% purity, 70% yield).

Example 45

4-(N-Ethylsulfamoyl)butyl acetate (I-46)

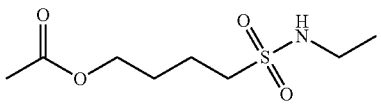

I-46

Intermediate I-46 was prepared from 4-bromobutyl acetate analogously to Examples 42-44.

Example 46

4-(N-Cyclopropylsulfamoyl)butyl pivalate (I-47)

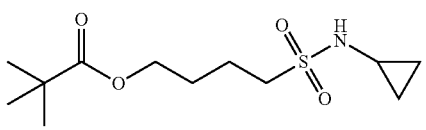

I-47

Intermediate I-47 was prepared from Intermediate I-44 analogously to Example 44.

Example 47

4-(N-Methylsulfamoyl)butyl acetate (I-48)

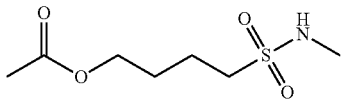

I-48

Intermediate I-48 was prepared from 4-bromobutyl acetate analogously to Examples 42-44.

Example 48

5-(N-methylsulfamoyl)pentyl pivalate (I-49)

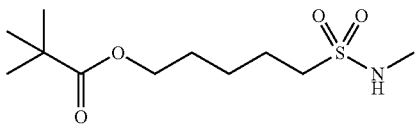

I-49

Intermediate I-49 was prepared from 4-bromopentyl pivalate analogously to Examples 42-44.

Example 49

5-(N-Cyclopropylsulfamoyl)pentyl pivalate (I-50)

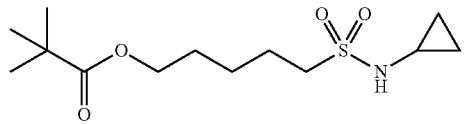

I-50

Intermediate I-50 was prepared from 4-bromopentyl pivalate analogously to Examples 42-44.

Example 50

5-(N-Ethylsulfamoyl)pentyl acetate (I-51)

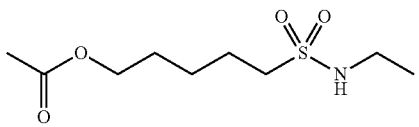

I-51

Intermediate I-51 was prepared from 5-bromopentyl acetate, analogously to Examples 42-44.

Example 51

5-(N-methylsulfamoyl)pentyl acetate (I-52)

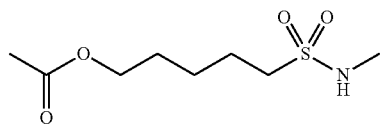

I-52

Intermediate I-52 was prepared from 5-bromopentyl acetate, analogously to Examples 42-44.

Example 52

N-methylbut-3-ene-1-sulfonamide (I-53)

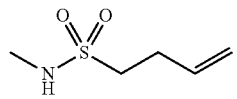
I-53

Intermediate I-53 was prepared from but-3-ene-1-sulfonyl chloride analogously to Example 44.

Example 53

N-methylpent-4-ene-1-sulfonamide (I-54)

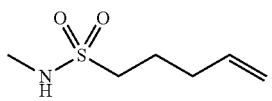
I-54

Intermediate I-54 was prepared from pent-4-ene-1-sulfonyl chloride analogously to Example 44.

Example 54

3-(N-methylsulfamoyl)propyl acetate (I-55)

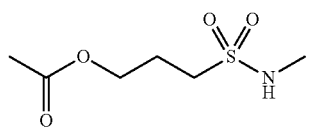
I-55

Intermediate I-55 was prepared from 3-(chlorosulfonyl)propyl acetate analogously to Example 44.

Example 55

3-Azido-N-methylpropane-1-sulfonamide (I-56)

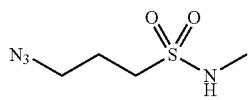
I-56

A mixture of 3-chloro-N-methylpropane-1-sulfonamide (29 mmol), NaN₃ (29 mmol) in DMF (50 ml) was stirred at 100° C. for 2 h. The mixture was poured into 40 ml of brine. The mixture was extracted with ether (3×30 ml). The organic layers were combined and washed with 20 ml of brine. The organic layer was dried with $Na_2SO_4$, filtered and the filtrate was evaporated. Yield: 4.2 g (90% purity, 81% yield).

Example 56 tert-Butyl 3-(N-methylsulfamoyl)propylcarbamate (I-57)

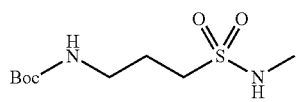
I-57

A mixture of Intermediate I-56 (14 mmol), 10% Pd/C (1 g), di-tert-butyl dicarbonate (Boc₂O; 14 mmol) in methanol (25 ml) was hydrogenated at 25° C. for 2 h. After uptake of hydrogen (3 eq.), the catalyst was filtered off. The filtrate was evaporated. The residue was purified by $SiO_2$ column (eluent: petroleum ether/ethyl acetate 3:1). Yield: 2 g (90% purity, 56% yield)

Example 57 tert-Butyl 4-(N-methylsulfamoyl)butylcarbamate (I-58)

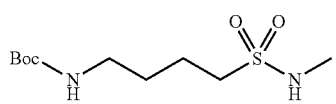
I-58

Intermediate I-58 was prepared from 4-chloro-N-methylbutane-1-sulfonamide analogously to Examples 55-56.

Example 58

4-Cyano-N-methylbutane-1-sulfonamide (I-59)

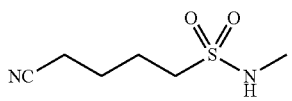
I-59

4-Chloro-N-methylbutane-1-sulfonamide (54 mmol), KCN (108 mmol) and 18-crown ether-6 (11 mmol) were dissolved in $CH_3CN$ (100 ml). The mixture was stirred at reflux temperature overnight. The mixture was cooled and filtered. The residue was purified by flash column chromatography over silica gel (eluent: $CH_2Cl_2$, then ethyl acetate). Yield: 3.2 g (70% purity).

Example 59

5-Amino-N-methylpentane-1-sulfonamide (I-60)

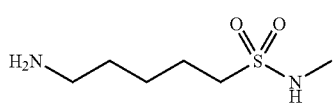
I-60

Intermediate I-59 (8.5 mmol) was dissolved in dry THF (30 ml) and the mixture was stirred at 0° C. Borane-Me₂S complex (34 mmol) was added dropwise. The reaction was stirred at room temperature. The mixture was cooled to 0° C., and methanol was added dropwise until gas evolution ceased. The solvent was evaporated. The crude product was used for the next step without further purification. Yield: 1.5 g (97% yield).

Example 60 tert-Butyl 5-(N-methylsulfamoyl)pentylcarbamate (I-61)

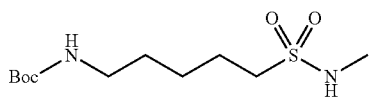

I-61

Intermediate I-60 (8.3 mmol) was dissolved in methanol (50 ml). The mixture was stirred at 0° C. Boc$_2$O (8.3 mmol) was added portion wise. The reaction was stirred at room temperature until completion of the reaction was ensured by thin-layer chromatography (TLC; petroleum ether/ethyl acetate 5:1). The solvent was evaporated. The crude was washed with petroleum ether. CH$_2$Cl$_2$ was added and the organic layer was washed with saturated NaHCO$_3$, brine. The organic layer was dried and evaporated. Yield: 1.7 g (73% yield).

Example 61 tert-Butyl 2,4-dimethoxybenzyl(5-oxopentyl)carbamate (I-62)

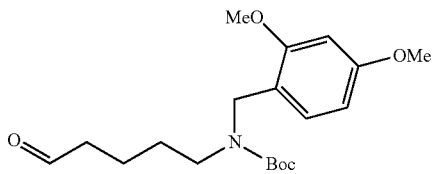

I-62

To a stirred solution of oxalyl chloride (7.8 mmol) in CH$_2$Cl$_2$ (13.5 ml) at −65° C. to −70° C. under N$_2$ was added dimethylsulfoxide (DMSO; 15.6 mmol) in CH$_2$Cl$_2$ (4 ml). After 2 min, a solution of Intermediate I-33 (7.1 mmol) in CH$_2$Cl$_2$ (7 ml) was added. After 20 min, triethyl amine (35 mmol) was added. After 10 min, the mixture was allowed to warm to 10° C. and water (32.5 ml) was added. After separation, the aqueous layer was extracted with CH$_2$Cl$_2$ (2×) and the combined organic layers were washed with saturated brine and dried over Na$_2$SO$_4$. The solvent was evaporated under reduced pressure. The residue was dried and used in the next step without further purification. The product was obtained as a brown oil. Yield: 2.4 g (97% yield).

Example 62 tert-Butyl 2,4-dimethoxybenzyl(6-oxohexyl)carbamate (I-63)

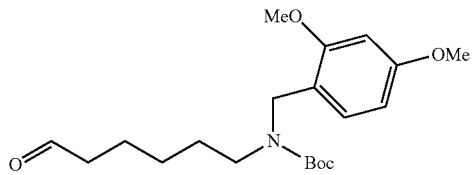

I-63

Intermediate I-63 was prepared from 6-aminohexan-1-ol analogously to Examples 31-32 and 61.

Example 63 tert-Butyl 6-(tert-butyldimethylsilyloxy)hexylcarbamate (I-64)

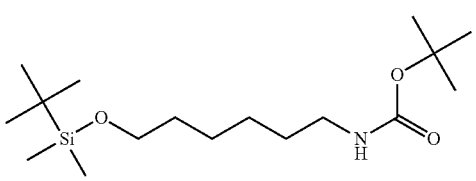

I-64

To a solution of tert-butyl 6-hydroxyhexylcarbamate (21 mmol) in CH$_2$Cl$_2$ (30 ml) was added imidazole (27 mmol) at 0° C. The reaction mixture was kept at 25° C. and stirred for 20 min, then cooled to 0° C. To the resulting reaction mixture was added tert-butyldimethylchlorosilane (23 mmol) dropwise over 30 min at 0° C. The reaction mixture was allowed to warm to 25° C. and stirred for 16 h and then filtered. The filtrate was washed with 1 N HCl (2×25 ml) and brine (30 ml), dried over Na$_2$SO$_4$, filtered and evaporated under reduced pressure. The residue was purified by SiO$_2$ flash column (eluent: petroleum ether and then CH$_2$Cl$_2$). Yield 6.53 g (87% yield).

Example 64 tert-Butyl 6-(tert-butyldimethylsilyloxy)hexyl(methyl)carbamate (I-65)

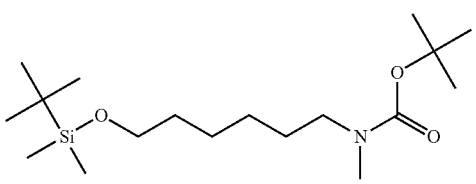

I-65

To a solution of Intermediate I-64 (18 mmol) in dry THF (100 ml) was added 60% NaH (91 mmol) portion wise at 0° C. The reaction mixture was stirred at 0° C. for 0.5 h. To the resulting reaction mixture was added iodomethane (54 mmol) dropwise at 0° C. The reaction mixture was allowed to warm to 25° C. and stirred for 16 h. Saturated NH$_4$Cl (100 ml) was added dropwise at 0° C. and the mixture was stirred for 0.5 h and filtered. The filtrate was extracted with tert-butyl methyl ether (3×50 ml). The combined organic portions were washed with brine, dried over Na$_2$SO$_4$, filtered and evaporated under reduced pressure. The residue was purified by SiO$_2$ flash column (eluent: petroleum ether and then petroleum ether/ethyl acetate 10:1). Yield: 5.67 g (85% yield).

Example 65 tert-Butyl 6-hydroxyhexyl(methyl)carbamate (I-66)

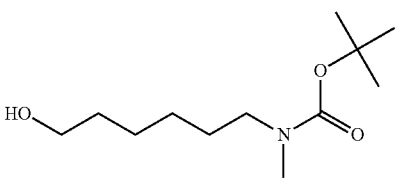

I-66

To a solution of Intermediate I-65 (15 mmol) in THF (85 ml) was added tetra-n-butylammonium fluoride (TBAF) as a 1 M solution in THF (30 mmol) dropwise at 0° C. and the reaction mixture was stirred for 2 h. Another amount of TBAF (15 mmol) was added and the reaction mixture was stirred for 16 h at 25° C. The organic solvent was evaporated under vacuum and ice-water (70 ml) was added. The resulting mixture was stirred for 1 h. The mixture was separated and the organic layer was washed by petroleum ether at −20° C. The residue was purified by flash column (eluent: petroleum ether and then petroleum ether/ethyl acetate 10:1). Yield: 2.1 g (60% yield).

Example 66 tert-Butyl methyl(6-oxohexyl)carbamate (I-67)

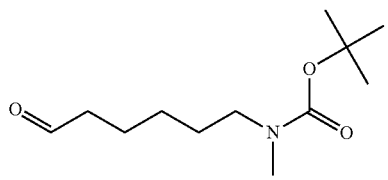

Intermediate I-67 was obtained following an analogous procedure as described in Example 61, starting from Intermediate I-66.

Example 67

Methyl 5-chloro-4-fluoro-2-(4-methoxybenzyloxy)benzoate (I-68)

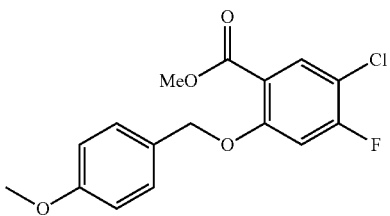

Intermediate I-68 was prepared from methyl 5-chloro-4-fluoro-2-hydroxybenzoate analogously to Example 37.

Example 68

(5-Chloro-4-fluoro-2-(4-methoxybenzyloxy)phenyl)methanol (I-69)

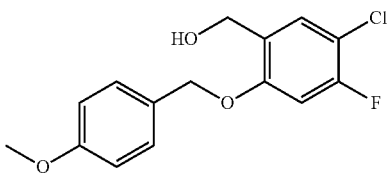

Intermediate I-68 (20.3 mmol) and LiBH$_4$ (203 mmol) were suspended in THF. The resulting mixture was stirred for 15 min at 65° C. Methanol (100 ml) was added dropwise during 0.5 h. Stirring at 65° C. was maintained overnight. The reaction was cooled to 15° C., and quenched with saturated aqueous NH$_4$Cl (100 ml). Stirring was continued for another 1 h. The organic layer was separated and the aqueous layer was extracted by ethyl acetate. The combined organic layers were washed with brine and dried over Na$_2$SO$_4$. The solvent was removed under vacuum. The residue was purified by SiO$_2$ flash column (elute: petroleum ether/ethyl acetate from 100:0 to 0:100) to give the target product. Yield: 5.7 g (95% yield).

Example 69

Methyl 4,5-difluoro-2-(4-methoxybenzyloxy)benzoate (I-70)

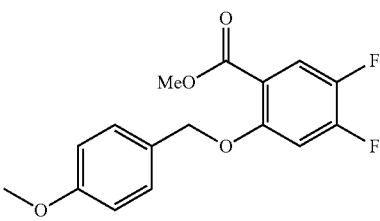

Intermediate I-70 was prepared from Intermediate I-35 analogously to Example 37.

Example 70

(4,5-Difluoro-2-(4-methoxybenzyloxy)phenyl)methanol (I-71)

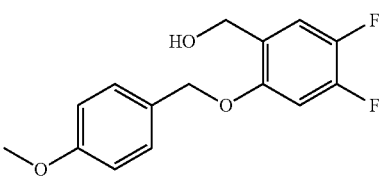

LiAlH$_4$ (20 mmol) was added to a solution of Intermediate I-70 (4.9 mmol) in dry THF (30 ml). The mixture was stirred at ambient temperature for 4 h. The reaction was quenched with 10% NaOH aqueous solution (0.5 ml) and water (2 ml). The mixture was filtered off and the filtrate was extracted with ethyl acetate. The organic layer was dried over Na$_2$SO$_4$ and the solvent was evaporated. The residue was purified by SiO$_2$ flash column (petroleum ether/ethyl acetate 100:0 to 50:50). The desired fraction was collected and the pure product was dried under vacuum. Yield: 1.1 g (80% yield).

Example 71

Intermediate I-72

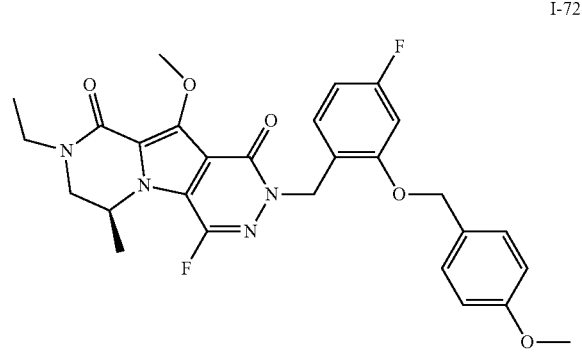 [SMILES: CCN1C[C@H](C)n2c(c(OC)c3c(=O)n(Cc4ccc(F)cc4OCc4ccc(OC)cc4)nc(F)c32)C1=O]

Intermediate I-2 (0.27 mol), Intermediate I-39 (0.33 mol) and triphenyl phosphine (0.41 mol) were dissolved in dry THF (1.6 l) at 20° C. DIAD (0.54 mol) was added while keeping the reaction temperature below −5° C. The mixture was stirred for 5 h at 0-10° C. The mixture was evaporated under vacuum. The residue was purified by column chromatography over silica gel (eluent: petroleum ether/ethyl acetate from 100:1 to 0:100). The pure fractions were collected and the organic solvent was evaporated. Yield: crude Intermediate I-72 200 g (50% purity), containing PPh$_3$=O.

Alternatively, the following procedure can be followed:

To a solution of Intermediate I-2 (32 mmol) in DMF (30 ml), was added lithium bis(trimethylsilyl)amide (LiHMDS; 1 M solution in THF; 39 mmol) at 0° C. The mixture was stirred for 0.5 h and then was treated with a freshly prepared batch of Intermediate I-41 (39 mmol) in one portion. The mixture was allowed to warm to 20° C. and stirred overnight. The solvent was removed under vacuum. The residue was dissolved in CH$_2$Cl$_2$ (60 ml) and the solution was washed with 1 N HCl (60 ml) and brine and dried over Na$_2$SO$_4$. The solvent was removed under vacuum. The residue was purified with flash column (gradient eluent: CH$_2$Cl$_2$/methanol 100:0 to 9:1). Yield: 10 g (90% purity, 58% yield).

Example 72

Intermediate I-73

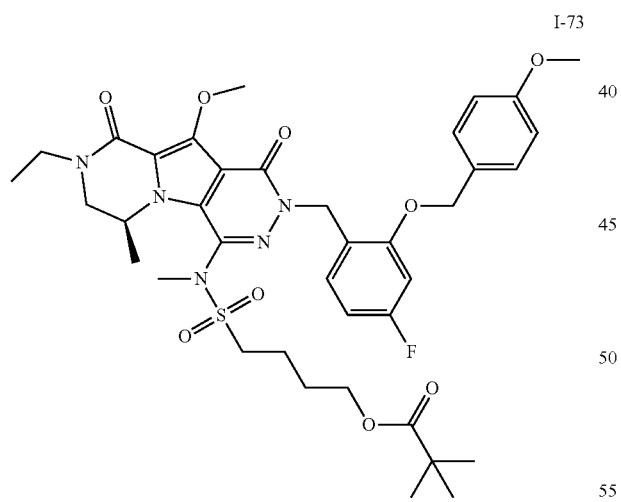

Intermediate I-72 (0.15 mol; 50% pure), Intermediate I-45 (0.18 mol) and CsCO$_3$ (0.25 mol) in DMSO (800 ml) were stirred overnight at 60° C. Saturated brine (800 ml) was added. The mixture was extracted with ethyl acetate (3×400 ml). The combined organic layers were washed with brine (2×200 ml) and dried over Na$_2$SO$_4$. The solvent was removed under vacuum. The resulting residue was washed with tert-butyl methyl ether. Yield: 70 g (80% purity).

Example 73

Intermediate I-74

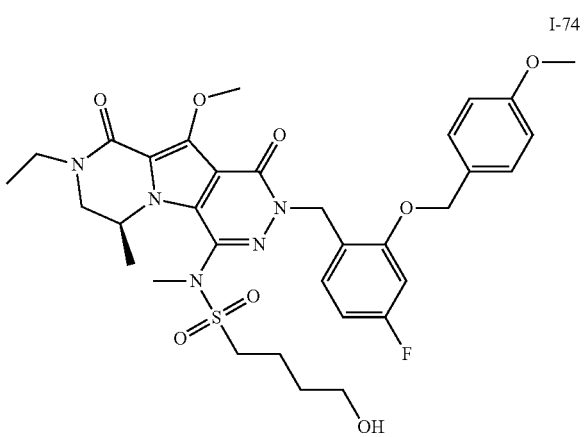 [SMILES: CCN1C[C@H](C)n2c(c(OC)c3c(=O)n(Cc4ccc(F)cc4OCc4ccc(OC)cc4)nc(N(C)S(=O)(=O)CCCCO)c32)C1=O]

A mixture of Intermediate I-73 (91 mmol) and NaOH (455 mmol) in methanol (700 ml) was stirred overnight at 20° C. The mixture was evaporated. Citric acid 10% was added until pH 3 was reached. The mixture was extracted with CH$_2$Cl$_2$ (2×800 ml). The combined organic layers were washed with brine and dried over Na$_2$SO$_4$. The solvent was removed under vacuum. The residue was purified with flash column chromatography over silica gel (eluent: petroleum ether/ethyl acetate 100:1 then 1:100 v/v). The resulting solid was further washed with tert-butyl methyl ether. Yield: 42 g (36% yield in total three steps).

Example 74

Intermediate I-75

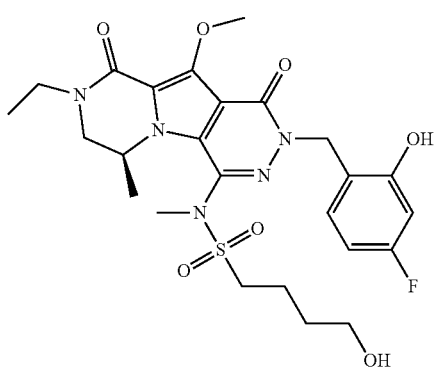

A mixture of Intermediate I-74 (61 mmol) was dissolved in CH$_2$Cl$_2$ (420 ml). The mixture was cooled to 0° C. A solution of HCl in dioxane (4 N; 336 mmol) was added dropwise. The mixture was stirred at 25° C. for 1 h. The solvent was removed under vacuum. The resulting solid was washed with methanol. Yield: 30 g (87% yield).

Example 75

Macrocylization (I-76)

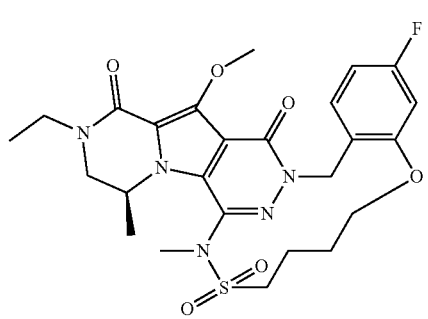

A solution of triphenyl phosphine (265 mmol) in dry THF (1500 ml) was cooled to 0° C. DIAD (265 mmol) was added dropwise at 0° C. The mixture was stirred for 5 min at 0° C. A solution of Intermediate I-75 (53 mmol) in dry THF (1500 ml) was added dropwise at 0° C. The mixture was stirred for 3 h at 20° C. The solvent was removed under vacuum. The residue was purified by SiO$_2$ flash column (gradient eluent: petroleum ether/ethyl acetate 3:2 to 1:1). The pure fractions were collected and the organic solvent was evaporated. The resulting product was further washed by tert-butyl methyl ether. Yield: 25 g (86% yield).

Example 76

Intermediate I-77

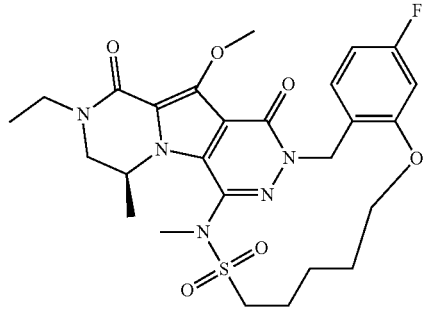

Intermediate I-77 was obtained following analogous procedures as described in Examples 72-75, using Intermediate I-72 and Intermediate I-49.

Example 77

Intermediate I-78

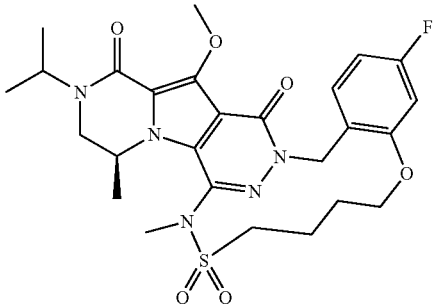

Intermediate I-78 was obtained following analogous procedures as described in Examples 71-75, using Intermediates I-5, I-39 and I-45.

Example 78

Intermediate I-79

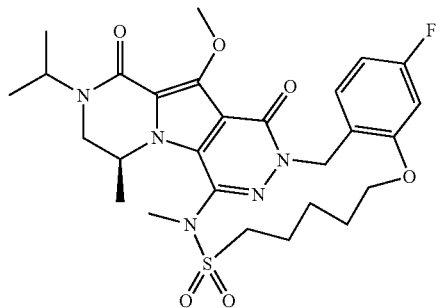

Intermediate I-79 was obtained following an analogous procedure as described in Examples 71-75, using Intermediates I-5, I-39 and I-49.

Example 79

Intermediate I-80

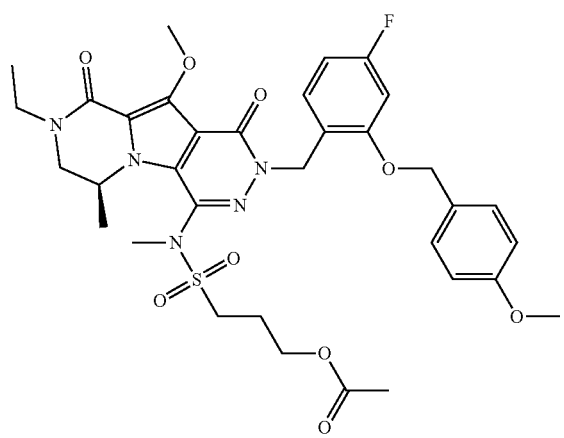

Intermediate I-80 was obtained following an analogous procedure as described in Example 72, using Intermediates I-72 and I-55.

Example 80

Intermediate I-81

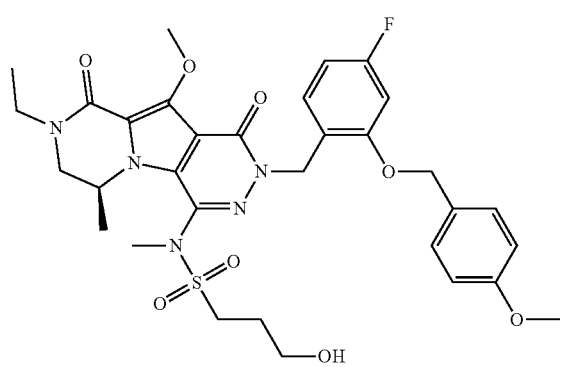

A solution of NaOH (25 mmol) in water (10 ml) was added to Intermediate I-80 (2.8 mmol) and stirred at 25° C. for 1 h. The mixture was neutralized with 10% citric acid and extracted with ethyl acetate. The organic layer was washed with brine twice, dried over Na$_2$SO$_4$ and concentrated under vacuum. The residue was purified by SiO$_2$ flash column. (gradient eluent: CH$_2$Cl$_2$ to methanol/CH$_2$Cl$_2$ 8:100). Yield: 1.3 g (80% purity).

Example 81

Intermediate I-82

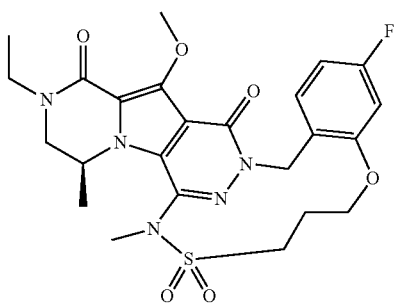

Intermediate I-82 was obtained following an analogous procedure as described in Examples 74 and 75, using Intermediate I-81.

Example 82

Intermediate I-83, 2 diastereomers

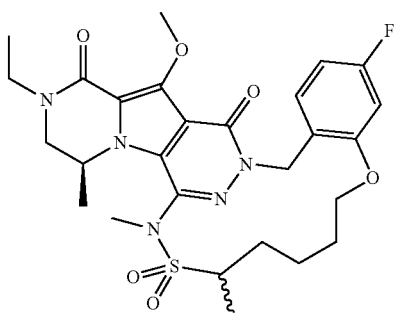

The macrocycle I-77 (0.45 mmol) in dry THF (5 ml) was cooled to −78° C. Lithium hexamethyl disilazide (1 M solution in THF; 0.49 mmol) was added dropwise under N$_2$. The mixture was stirred for 0.5 h at −78° C. Iodomethane (0.58 mmol) was added drop wise. The mixture was allowed to warm to room temperature and stirred for 3 h at 25° C. Water (5 ml) was added to quench the reaction. The mixture was extracted with ethyl acetate (3×10 ml). The combined organic layers were washed with brine and dried over Na$_2$SO$_4$. The solvent was removed under vacuum. The residue was purified by high-performance liquid chromatography (HPLC; C18, eluent: methanol/H$_2$O from 15:85 to 45:55 with 0.1% trifluoroacetic acid (TFA) as buffer). The pure fractions were collected and the volatiles were removed under vacuum and the aqueous solution was basified with saturated aqueous NaHCO$_3$ to pH 8 and extracted with CH$_2$Cl$_2$ (2×30 ml). The combined organic layers were washed with brine and dried over Na$_2$SO$_4$. The solvent was removed under vacuum. The residue was further purified by Supercritical Fluid Chromatography separation (ChiralPak AS_H, 5 µm; mobile phase: supercritical CO$_2$: propan-2-ol (0.05% diethyl amine), v/v=70:30, 40 ml/min, column temperature: 38° C., nozzle pressure: 100 bar, nozzle temperature: 60° C., evaporator temperature: 20° C., trimmer temperature: 25° C., wavelength: 220 nm). The pure fractions were collected and the solvent was concentrated under vacuum. Yield: 20 mg (95% purity, 8% yield) for the first-eluting isomer; and 96 mg (95% purity, 38% yield) for the second-eluting isomer.

Example 83

Intermediate I-84

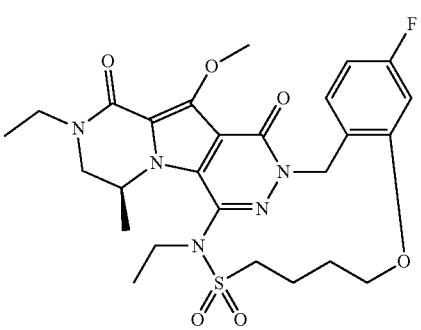

Intermediate I-84 was obtained following analogous procedures as described in Examples 72; 80; 74-75, using Intermediates I-72 and I-46.

Example 84

Intermediate I-85

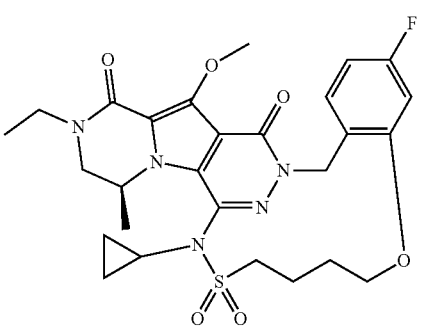

Intermediate I-85 was obtained following analogous procedures as described in Examples 72-75, using Intermediates I-72 and I-47.

Example 85

Intermediate I-86

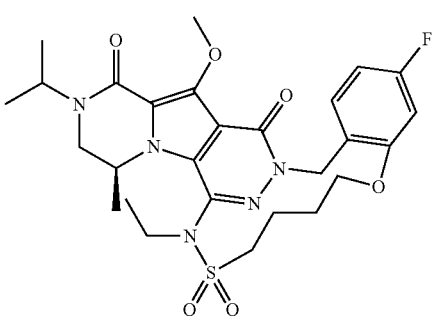

Intermediate I-86 was obtained following analogous procedures as described in Examples 71-72; 80; 74-75, using Intermediates I-5, I-41 and I-46.

Example 86

Intermediate I-87

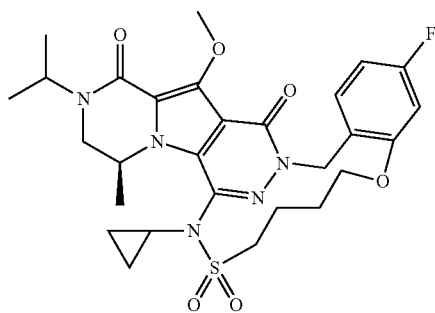

Intermediate I-87 was obtained following analogous procedures as described in Examples 71-75, using Intermediates I-5, I-41 and I-47.

Example 87

Intermediate I-88

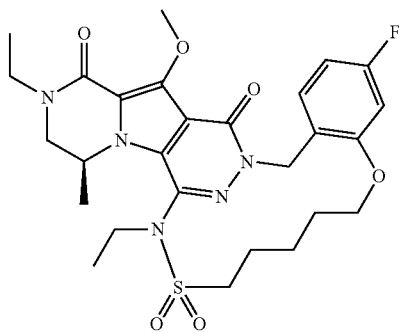 [SMILES: CCN1C[C@H](C)n2c(c(OC)c3c(=O)n4nc(c32)N(CC)S(=O)(=O)CCCCCOc2cc(F)ccc2C4)C1=O]

Intermediate I-88 was obtained following analogous procedures as described in Examples 71-72; 80; 74-75, using Intermediates I-2, I-41 and I-51.

Example 88

Intermediate I-89

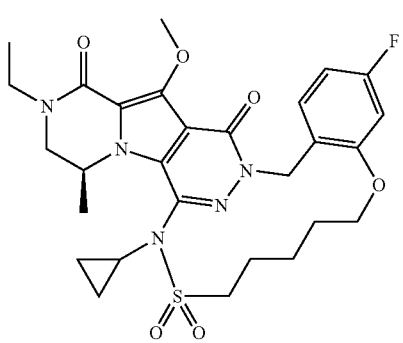

Intermediate I-89 was obtained following analogous procedures as described in Examples 71-72; using Intermediates I-2, I-41 and I-50.

Example 89

Intermediate I-90

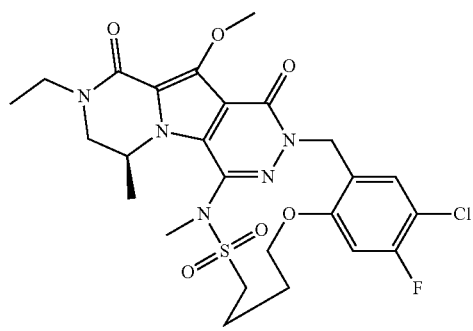

Intermediate I-90 was obtained following analogous procedures as described in Examples 71-75, using Intermediates I-2, I-69 and I-45.

Example 90

Intermediate I-91

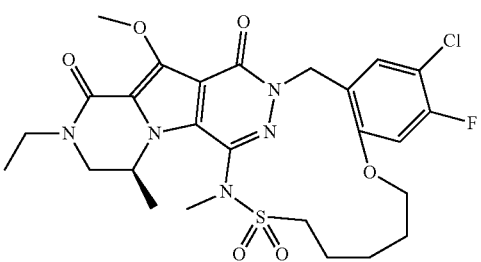

Intermediate I-91 was obtained following analogous procedures as described in Examples 71-75, using Intermediates I-2, I-69 and I-49.

Example 91

Intermediate I-92

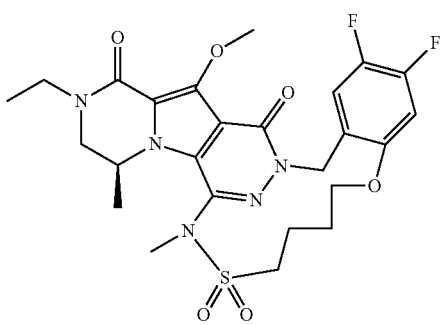

Intermediate I-92 was obtained following analogous procedures as described in Examples 71-72; 80; 74-75, using Intermediates I-2, I-71 and I-48.

Example 92

Intermediate I-93

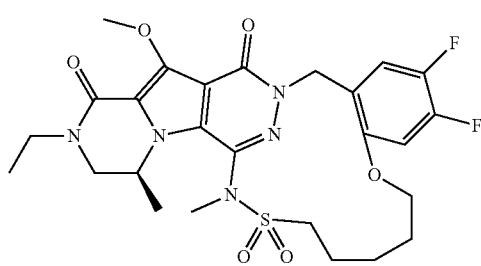

Intermediate I-93 was obtained following analogous procedures as described in Examples 71-75, using Intermediates I-2, I-71 and I-52.

Example 93

Intermediate I-95

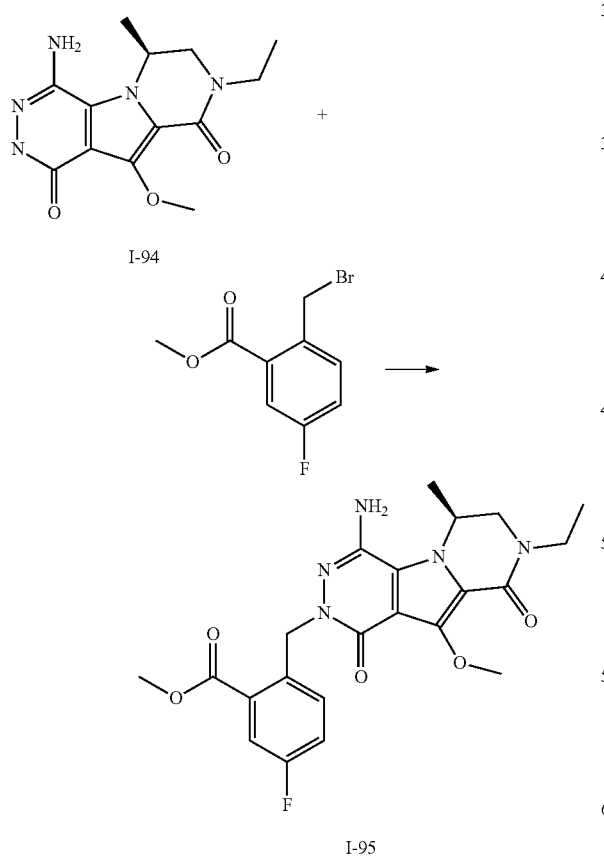

To a solution of the tricyclic amine I-94 (33 mmol) in DMF (100 ml) was added LiHMDS (1 M in THF, 40 mmol) at 10° C. The mixture was stirred for 30 min and then it was treated with methyl 2-(bromomethyl)-5-fluorobenzoate (35 mmol) in one portion. The reaction mixture was stirred at 10° C. for 3 h and concentrated under vacuum. The residue was partitioned between $CH_2Cl_2$ and 1N HCl. The organic extract was washed with brine, dried over $Na_2SO_4$, filtered and concentrated under vacuum. The residue was washed by ether/$CH_2Cl_2$, filtered to afford crude product, which was triturated with $CH_3CN$/diethyl ether 1:1 to afford 3.5 g yellow powder. The mother liquid was concentrated and purified by $SiO_2$ column chromatography (methanol/$CH_2Cl_2$ 1:20) to afford 4 g yellow powder. Yield: 7.5 g (97% purity; 50% yield).

Example 94

Intermediate I-96

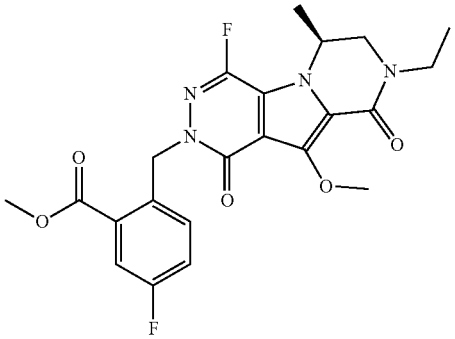

Intermediate I-95 (44 mmol) was dissolved in HF-pyridine (30 ml) in a three-necked polytetrafluoroethylene (PTFE) flask. The mixture was stirred at 0° C. $NaNO_2$ (48 mmol) was added portion wise during 10 min. The mixture was stirred at room temperature for 1 h. The mixture was added dropwise to saturated aqueous $NaHCO_3$. The mixture was extracted with ethyl acetate. The organic layer was separated, dried and evaporated. Yield: 2 g (98% yield).

Example 95

Intermediate I-97

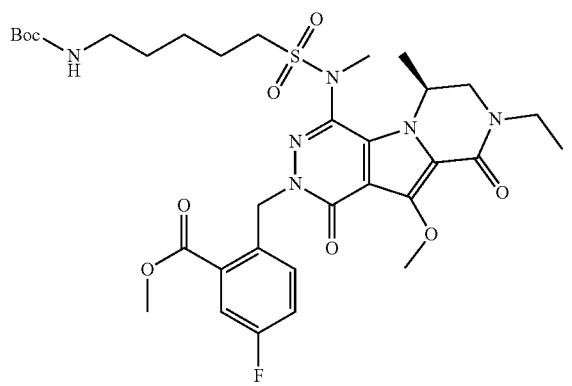

Intermediates I-96 (2.2 mmol) and I-61 (4.3 mmol), and $CsCO_3$ (7.4 mmol) were dissolved in DMSO (80 ml). The reaction mixture was stirred at 60° C.-70° C. for 17 h. The reaction mixture was used in the next step without further purification.

Example 96

Intermediate I-98

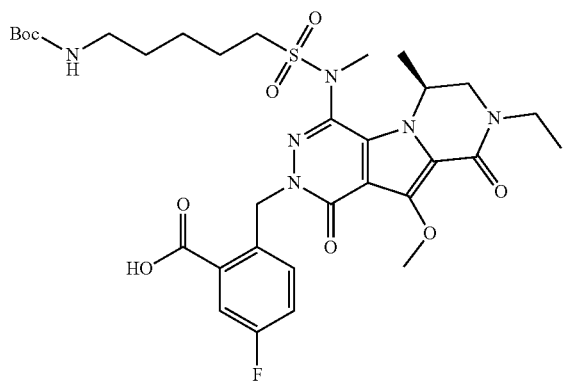

To the crude solution of Intermediate I-97 was added water (20 ml), followed by NaOH (9.8 mmol) at 17° C. and the reaction mixture was stirred for 40 min. Saturated brine (120 ml) and water (50 ml) were added to the reaction mixture. The aqueous portion was acidified to pH 3 using 1.0 M HCl and extracted with $CH_2Cl_2$ (3×100 ml). The combined organic extracts were washed with brine (100 ml), dried over $Na_2SO_4$, filtered and concentrated in vacuo. The residue was purified by preparative HPLC (column: Luna 300×50 mm, 0.01 mm, eluent $CH_3CN/H_2O$ from 35:65 to 65:35, 0.1% TFA). The pure fractions were collected and the organic solvent was evaporated. The aqueous portion was extracted with $CH_2Cl_2$. The combined organic layer was washed with saturated brine, dried over $Na_2SO_4$. The organic layer was filtered and concentrated under vacuum. Yield: 1.06 g (98% purity; 69% yield).

Example 97

Intermediate I-99

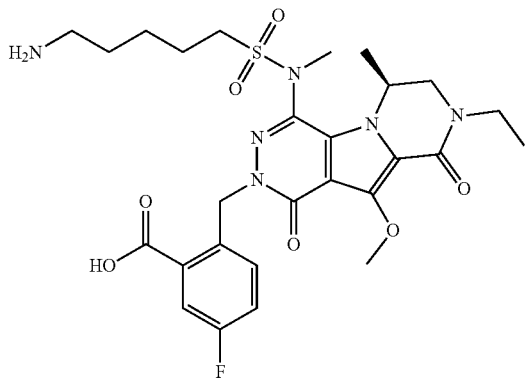

Intermediate I-98 (1.4 mmol) was dissolved in $CH_2Cl_2$ (10 ml) and the mixture was cooled to 0° C. TFA (10 ml) was added dropwise to the mixture at 0° C. The reaction mixture was allowed to warm up to 20° C. and stirred for 0.5 h. The solvent was evaporated under reduced pressure. The residue was co-evaporated by toluene (2×20 ml) and used in the next step without further purification. Yield: 1 g (TFA salt, 99% purity, 98% yield).

Example 98

Intermediate I-100

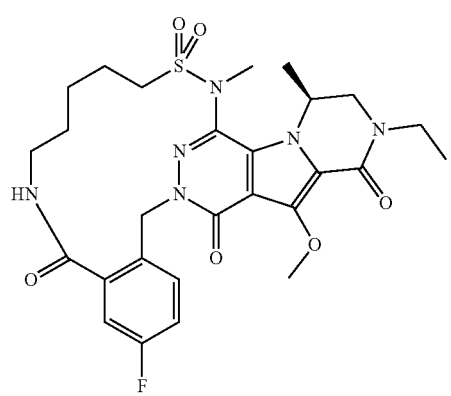

Pentafluorophenyl diphenylphosphinate (FDPP; 1.4 mmol) and DIPEA (1.6 ml) was dissolved in DMF (150 ml) at 18° C. A mixture of Intermediate I-99 (1.4 mmol) and DIPEA (0.8 ml) in DMF (150 ml) was added dropwise at 18° C. The reaction mixture was stirred overnight at 18° C. The mixture was then evaporated under vacuum. The residue was dissolved in $CH_2Cl_2$ (30 ml), washed with 1 N HCl aqueous solution (2×16 ml), saturated $NaHCO_3$ (21 ml) and brine (20 ml), dried over $Na_2SO_4$. The solvent was removed under vacuum. The residue was washed by diethyl ether (10 ml), and filtered to afford a pale white powder. Yield: 0.65 g (93% purity; 80% yield).

Example 99

Intermediate I-101

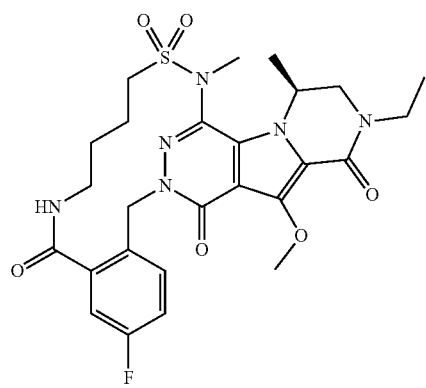

Intermediate I-101 was obtained following analogous procedures as described in Examples 95-98, using Intermediates I-96 and I-58.

Example 100

Intermediate I-102

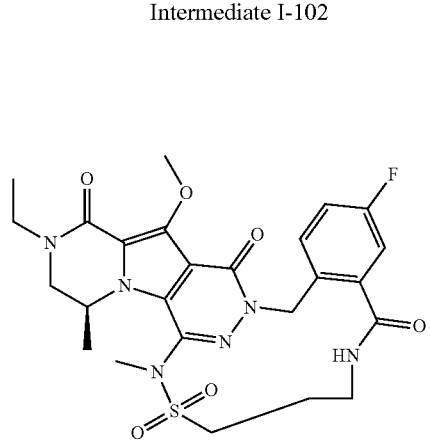

Intermediate I-102 was obtained following analogous procedures as described in Examples 95-98, using Intermediates I-96 and I-57.

Example 101

Intermediate I-103

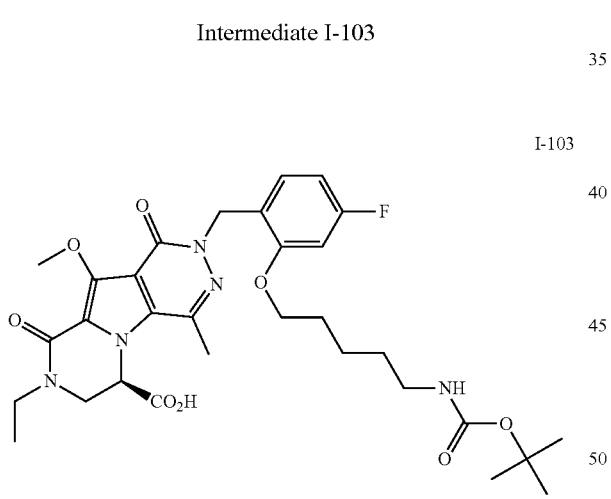

Intermediates I-16 (123 mmol) and I-27 (185 mmol), and triphenyl phosphine (245 mmol) were dissolved in dry THF at 20° C. DIAD (245 mmol) was added below −5° C. The mixture was stirred for 5 h at 0-10° C. LC-MS indicated that the starting material had disappeared and that the desired product was formed. NaOH in water/methanol (1:1; 0.17 N, 1.61) was added. The mixture was stirred for 0.5 h at 30° C. The solvents were evaporated under vacuum. The mixture was extracted with tert-butyl methyl ether (3×100 ml) to remove the impurities. 2 N HCl was added to the aqueous layer until pH was 2-3. The aqueous mixture was then extracted with ethyl acetate (2×200 ml). The combined organic layer was washed with brine, dried and evaporated. The crude product was used in the next step without further purification. Yield: 65 g (84% yield).

Example 102

Intermediate I-104 (TFA salt)

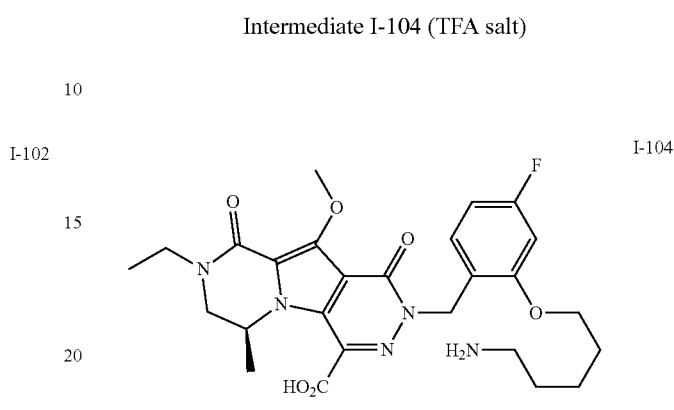

Intermediate I-103 (103 mmol) was dissolved in CH$_2$Cl$_2$ (650 ml) at 20° C. TFA (260 ml) was added dropwise at 0° C. The mixture was stirred for 0.5 h at 20° C. The solvent was removed under vacuum. The residue was co-evaporated with toluene (2×50 ml) and used in the next step without further purification. Yield: 65 g (85% purity).

Example 103

Intermediate I-105

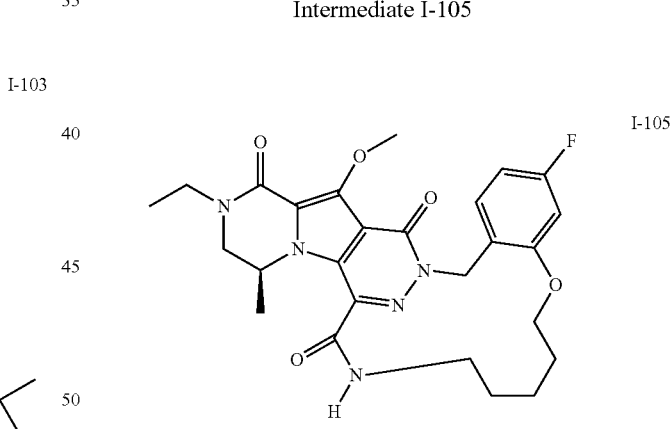

FDPP (113 mmol) and DIPEA (1.24 mol) were dissolved in THF (7 l) at 30° C. Intermediate I-104 (103 mmol) in THF (7 l) was added dropwise at 30° C. The mixture was stirred overnight at 30° C. The solvent was removed under vacuum. The residue was dissolved in CH$_2$Cl$_2$ (2 l) and washed with 1 N HCl (2×500 ml), saturated aqueous NaHCO$_3$, and brine. The organic layer was dried over Na$_2$SO$_4$. The solvent was removed under vacuum. The residue was purified by flash column chromatography over silica gel (eluent: CH$_2$Cl$_2$/methanol 100:3 then 100:7 v/v). The pure fractions were collected and concentrated to dryness. The resulting residue was washed with tert-butyl methyl ether. Yield: 46 g (79% overall yield for two steps).

Example 104

Intermediate I-106

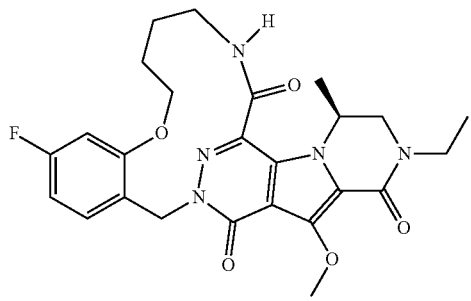

Intermediate I-106 was obtained following analogous procedures as described in Examples 101-103, using Intermediates I-16 and I-29.

Example 105

Intermediate I-107

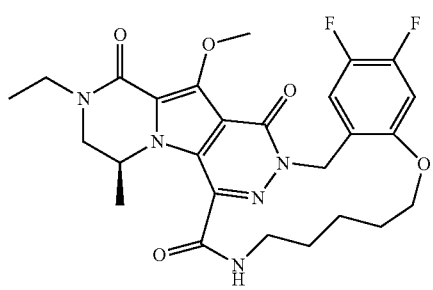

Intermediate I-107 was obtained following analogous procedures as described in Examples 101-103, using Intermediates I-16 and I-37.

Example 106

Intermediate I-108

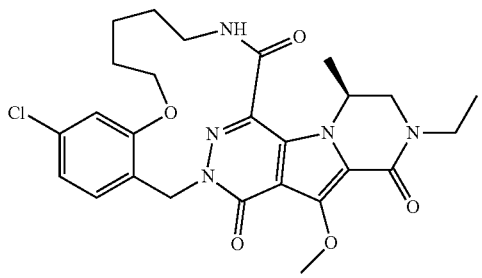

Intermediate I-108 was obtained following analogous procedures as described in Examples 101-103, using Intermediates I-16 and I-31.

Example 107

Intermediate I-109

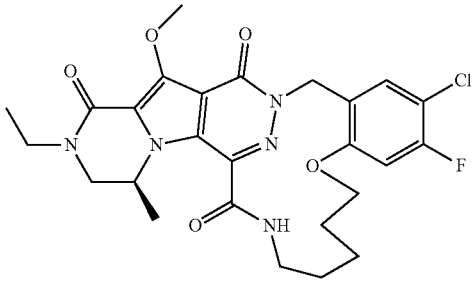

Intermediate I-109 was obtained following analogous procedures as described in Examples 101-103, using Intermediates I-16 and I-30.

Example 108

Intermediate I-110

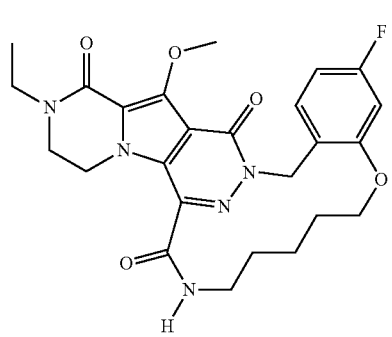

Intermediate I-110 was obtained following analogous procedures as described in Examples 101-103, using Intermediates I-23 and I-27.

Example 109

Intermediate I-111

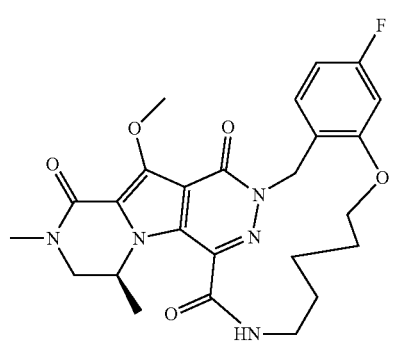

Intermediate I-111 was obtained following analogous procedures as described in Examples 101-103, using Intermediates I-18 and I-27.

Example 110

Intermediate I-112

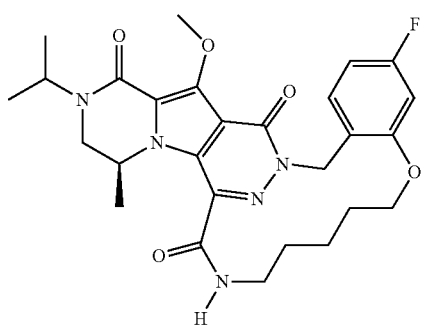

Intermediate I-112 was obtained following analogous procedures as described in Examples 101-103, using Intermediates I-17 and I-27.

Example 111

Intermediate I-113

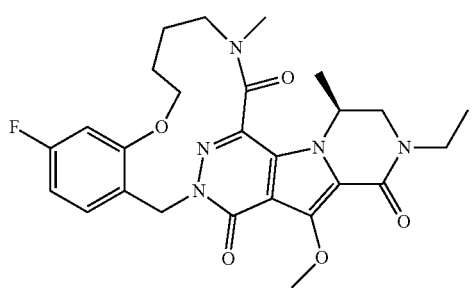

Intermediate I-106 (0.44 mmol) was dissolved in dry THF (7 ml). NaH (60%; 0.66 mmol) was added at 0° C. The mixture was stirred at 0° C. for 15 min. Then, iodo methane (0.66 mmol) was added dropwise and the mixture was stirred for 40 min at 15° C. The mixture was quenched with saturated aqueous $NH_4Cl$ and the solvent was removed under vacuum. The mixture was extracted with $CH_2Cl_2$ (2×10 ml). The combined organic layers were washed with brine and dried over $Na_2SO_4$. The solvent was removed under vacuum. The residue was washed with diethyl ether. Yield: 0.2 g (purity 89%, 88% yield).

Example 112

Intermediate I-114

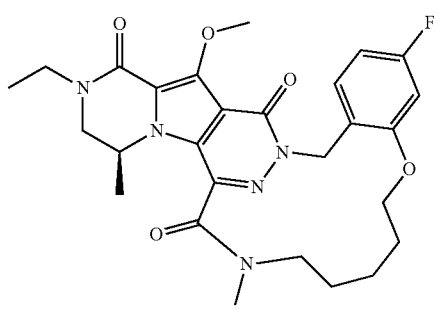

Intermediate I-114 was obtained following an analogous procedure as described in Example 111, using Intermediate I-105.

Example 113

Intermediate I-115

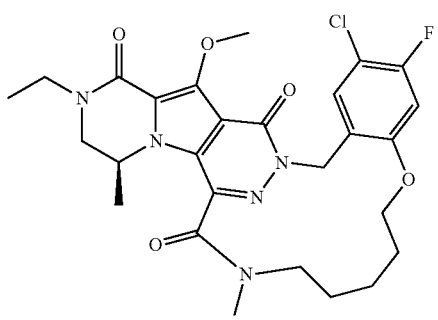

Intermediate I-115 was obtained following an analogous procedure as described in Example 111, using Intermediate I-109.

Example 114

Intermediate I-116

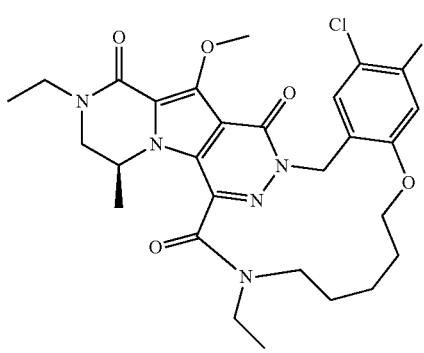

Intermediate I-116 was obtained following an analogous procedure as described in Example 111, using Intermediate I-109 and iodo ethane.

Example 115

Intermediate I-117

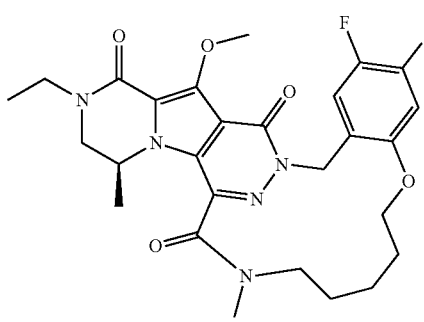

Intermediate I-117 was obtained following an analogous procedure as described in Example 111, using Intermediate I-107.

Example 116

Intermediate I-118

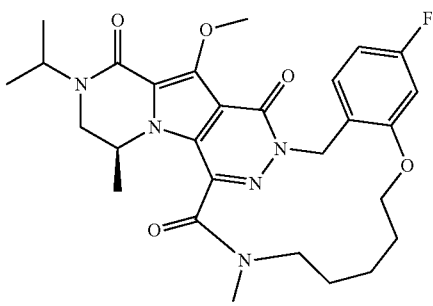

Intermediate I-118 was obtained following an analogous procedure as described in Example 111, using Intermediate I-112.

Example 117

Intermediate I-119

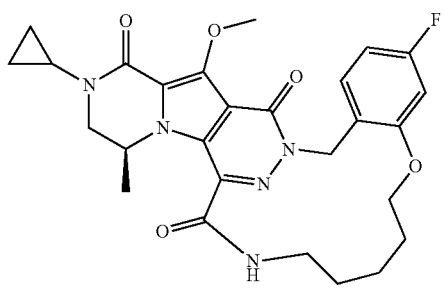

Intermediate I-119 was obtained following analogous procedures as described in Examples 101-103, using Intermediates I-24 and I-27.

Example 118

Intermediate I-120

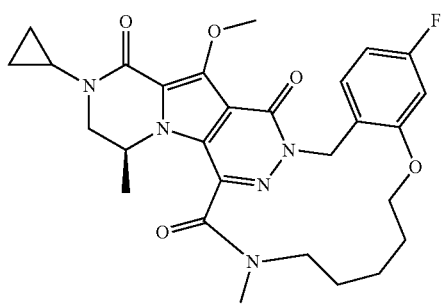

Intermediate I-120 was obtained following an analogous procedure as described in Example 111, using Intermediate I-119.

Example 119

Intermediate I-121

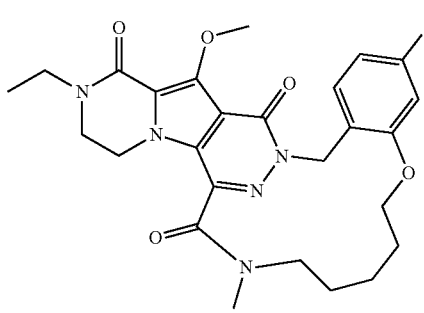

Intermediate I-121 was obtained following an analogous procedure as described in Example 111, using Intermediate I-110.

Example 120

Intermediate I-122

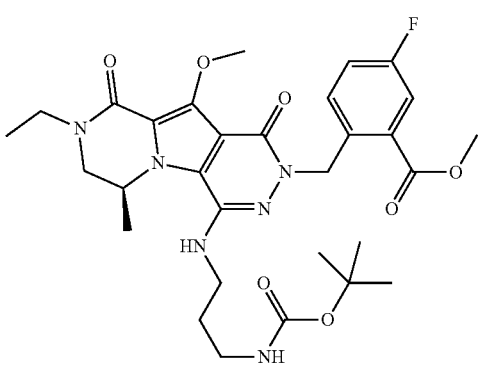

Intermediate I-95 (2.2 mmol) was dissolved in 2-propanol (30 ml). tert-Butyl 3-oxopropylcarbamate (11 mmol) and acetic acid (11 mmol) were added. The mixture was refluxed for 4 h and cooled to 0° C. Methanol (30 ml) was added, then $NaBH_4$ (22 mmol) was added at 0° C., and the mixture was stirred at 0° C. for 1 h. $NaHCO_3$ (saturated aqueous 10 ml) and $CH_2Cl_2$ (50 ml) were added. The organic layer was washed with brine and dried ($Na_2SO_4$). The solvent was removed under vacuum. The residue was purified by HPLC(C18, eluent: methanol/$H_2O$ from 15:85 to 45:55 with 0.1% TFA as buffer). The pure fractions were collected, the volatiles were removed under vacuum and the aqueous solution was basified with $NaHCO_3$ to pH 8. $CH_2Cl_2$ (200 ml) was added and the organic layer was washed with brine and dried ($Na_2SO_4$). Yield: 1.1 g (95% purity, 81% yield).

Example 121
Intermediate I-123

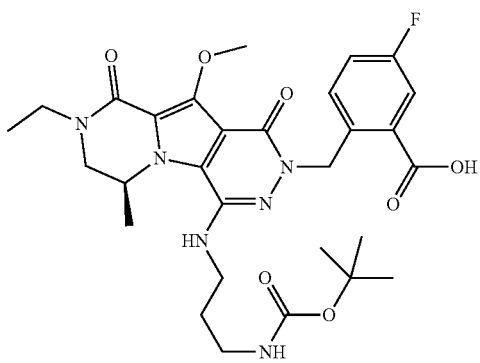

To a solution of Intermediate I-122 (1.8 mmol) in methanol (11 ml) and THF (11 ml) was added LiOH hydrate (9.0 mmol) in water (11 ml) at 20° C. The mixture was stirred at 20° C. for 5 h. The reaction mixture was concentrated in vacuo. Then water (15 ml) was added and the aqueous layer was extracted by diethyl ether (2×20 ml). The aqueous portion was acidified to pH 7 using 1 M HCl at 0° C. and extracted with ethyl acetate to remove impurities. The aqueous portion was then acidified to pH 3 using 1 M HCl at 0° C. and extracted with ethyl acetate (2×20 ml). The combined organic extracts were washed with brine, dried over $Na_2SO_4$, filtered, and concentrated in vacuo to afford the acid as a pale yellow powder. Yield: 1 g (95% purity, 94% yield).

Example 122
Intermediate I-124

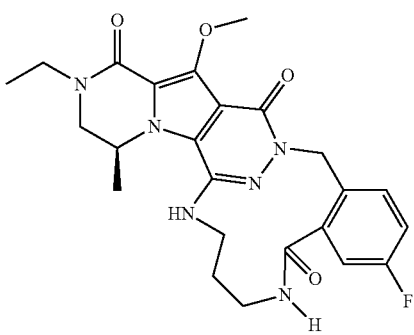

Intermediate I-124 was obtained following analogous procedures as described in Examples 97-98, using Intermediate I-123.

Example 123
Intermediate I-125

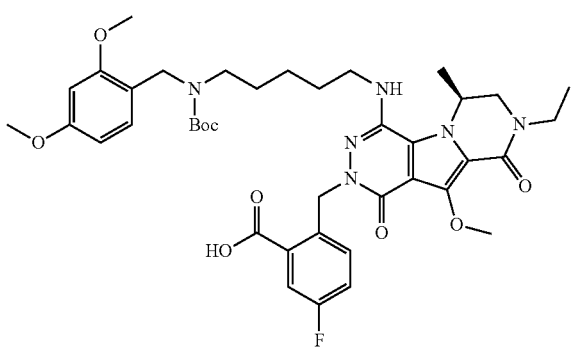

Intermediate I-125 was obtained following analogous procedures as described in Examples 120-121, using Intermediates I-95 and I-62.

Example 124
Intermediate I-126

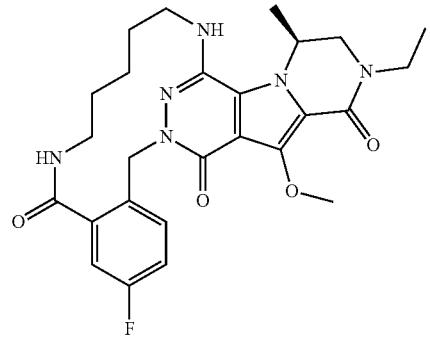

Intermediate I-126 was obtained following analogous procedures as described in Examples 97-98, using Intermediate I-125.

Example 125
Intermediate I-127

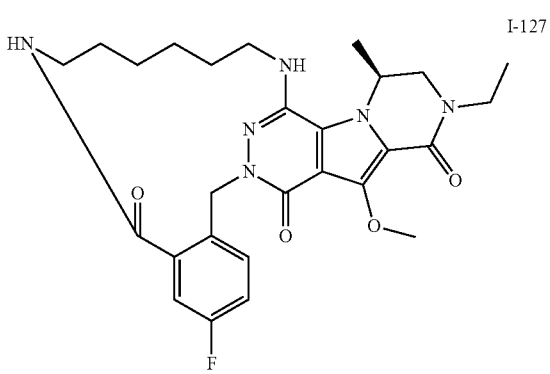 [SMILES: CCN1C[C@H](C)n2c(c(OC)c3c(=O)n4nc(c32)NCCCCCCNC(=O)c2cc(F)ccc2C4)C1=O]

Intermediate I-127 was obtained following analogous procedures as described in Examples 120-121, and Examples 97-98, using Intermediates I-95 and tert-butyl 6-oxohexylcarbamate.

Example 126
Intermediate I-128

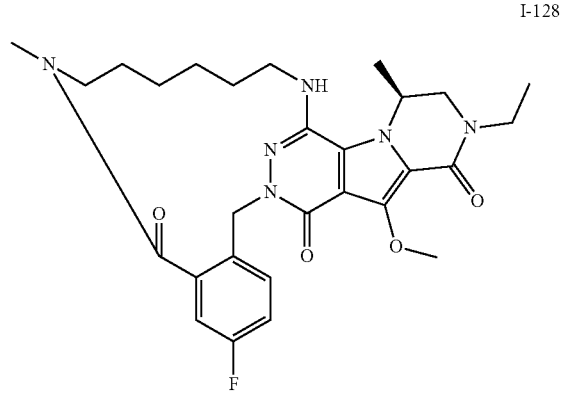 [SMILES: CCN1C[C@H](C)n2c(c(OC)c3c(=O)n4nc(c32)NCCCCCCN(C)C(=O)c2cc(F)ccc2C4)C1=O]

Intermediate I-128 was obtained following analogous procedures as described in Examples 120-121, and Examples 97-98, using Intermediates I-95 and I-67.

Example 127

Intermediate I-129

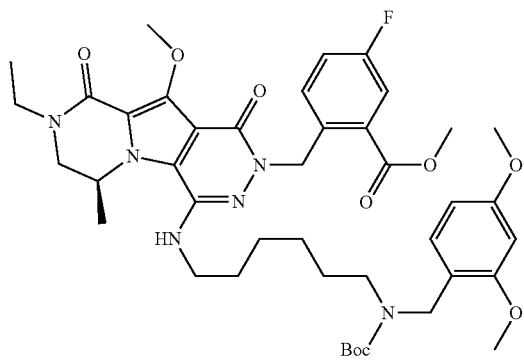

I-129

Intermediate I-129 was obtained following an analogous procedure as described in Example 120, using Intermediates I-95 and I-63.

Example 128

Intermediate I-130

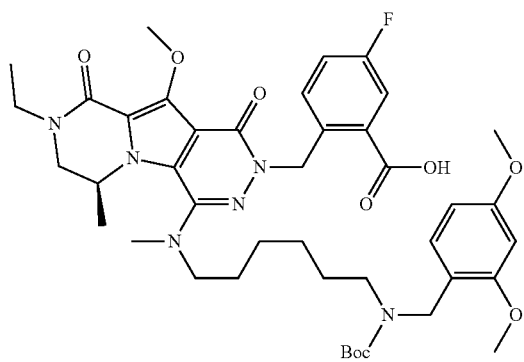

I-130

To a solution of Intermediate I-129 (0.69 mmol) in dry THF (8 ml) was added NaH (60%; 0.69 mmol) in one portion at 0° C. The reaction mixture was stirred at 0° C. for 15 min. To the reaction mixture was added iodo methane (1.6 mmol) dropwise at 0° C. The reaction mixture was allowed to warm to 20° C. and stirred for 1.5 h. To the reaction mixture was added additional NaH (60%, 0.30 mmol) at 0° C. and then the mixture was stirred for 5 min. Another batch of iodo methane (1.5 mmol) was added dropwise at 0° C., and the reaction mixture was stirred at 20° C. for a further 0.5 h. The hydrolyzed product was found by liquid chromatography-mass spectrometry (LC/MS). Water (8 ml) was added to the reaction mixture and then methyl tert-butyl ether (8 ml) was added. The aqueous layer was separated and acidified to pH 7 by using 1 N HCl and then extracted by ethyl acetate (8 ml) to remove the impurities. The aqueous layer was then separated and acidified to pH 2 by using 1 N HCl and extracted by ethyl acetate (3×8 ml). The combined organic layer was washed with saturated brine (15 ml), dried over $Na_2SO_4$. The organic solvent was filtered and concentrated under vacuum. The residue was purified by preparative HPLC (column: Gemini 200×25 mm, 0.005 mm, eluent $CH_3CN/H_2O$ from 68% to 88%, 0.05% TFA). The pure fractions were collected and the organic solvent was evaporated. The aqueous portion was extracted with $CH_2Cl_2$. The combined organic layer was washed with saturated brine, dried over $Na_2SO_4$. The organic layer was filtered and concentrated under vacuum. Yield: 300 mg (98% purity, 54% yield).

Example 129

Intermediate I-131

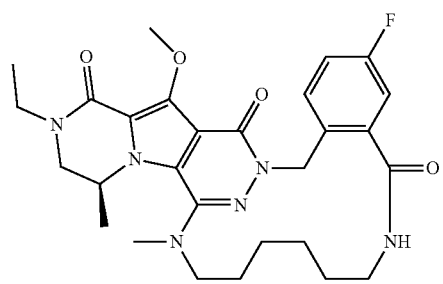

I-131

Intermediate I-131 was obtained following analogous procedures as described in Examples 97-98, using Intermediate I-130.

Example 130

Intermediates I-132 and I-133

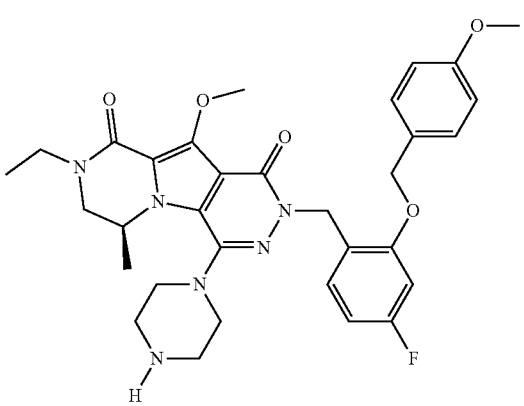

I-132

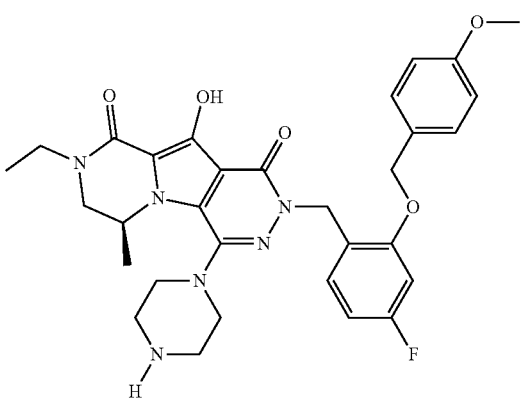

I-133

Intermediate I-72 (7.1 mmol), piperazine (141 mmol) and 4 Å molecular sieves (3.8 g) were suspended in NMP (N-methylpyrrolidone). The mixture was stirred overnight at 120° C. The molecular sieves were filtered off, after the reaction mixture was cooled to room temperature. Water (50 ml) and $CH_2Cl_2$ (100 ml) were added to the resulting filtrate. A precipitate formed, which was collected by filtration and the structure was found to be that of I-133; 1.1 g (purity 90%).

Example 131

Intermediate I-134

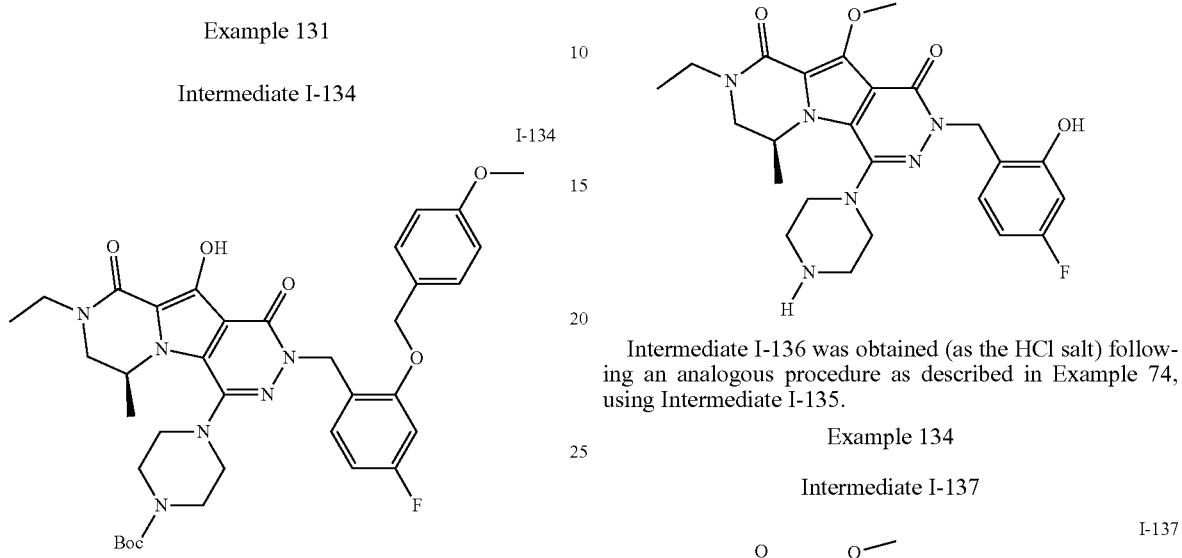

The mixture of Intermediates I-132 and I-133 (ratio 1:2; 3 g) was dissolved in methanol (30 ml). Boc₂O (1.1 g) was added at 0° C. The mixture was stirred for 1 h at 15° C. Then, another batch of Boc₂O (1.1 g) was added. The mixture was stirred overnight at 10° C., after which yet another batch of Boc₂O (3.3 g) was added. The mixture was stirred for another 3 h at 15° C. The solvent was removed under vacuum. The residue was purified with $SiO_2$ flash column (gradient eluent: $CH_2Cl_2$/methanol 100:0 to 90:10). Yield: 2.1 g (80% purity; 60% yield).

Example 132

Intermediate I-135

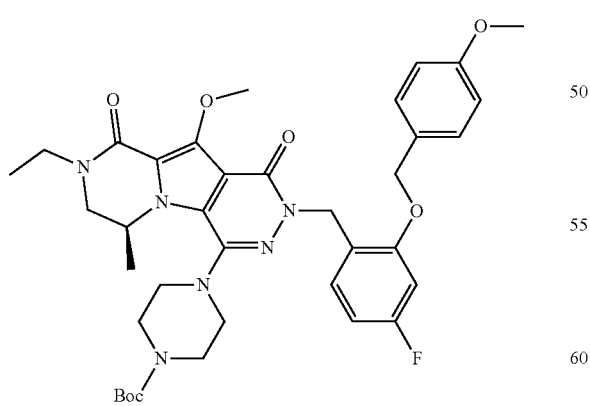

Intermediate I-134 (3.0 mmol) was dissolved in DMF (20 ml). Iodo methane (15 mmol) and $K_2CO_3$ (15 mmol) were added. The mixture was stirred overnight at 10° C. Water (20 ml) and $CH_2Cl_2$ (40 ml) were added. The organic layer was separated and washed with brine and dried over $Na_2SO_4$. The solvent was removed under vacuum. Yield: 1.7 g (85% purity).

Example 133

Intermediate I-136

Intermediate I-136 was obtained (as the HCl salt) following an analogous procedure as described in Example 74, using Intermediate I-135.

Example 134

Intermediate I-137

Intermediate I-137 was obtained following an analogous procedure as described in Example 131, using Intermediate I-136. The reaction required the presence of triethyl amine (3 eq.).

Example 135

Intermediate I-138

Intermediate I-137 (0.77 mmol) was dissolved in DMF (5 ml). Methyl 4-bromobutanoate (0.92 mmol) and K₂CO₃ (1.54 mmol) were added. The mixture was stirred overnight at 10° C. Water (10 ml) and CH₂Cl₂ (20 ml) were added. The organic layer was separated and the aqueous layer was extracted with CH₂Cl₂ (20 ml). The combined organic layers were washed with brine and dried over Na₂SO₄. The solvent was removed under vacuum. The residue was purified with SiO₂ flash column (gradient eluent: CH₂Cl₂/methanol 100:0 to 90:10). Yield: 0.45 g (90% purity, 85% yield).

Example 136

Intermediate I-139

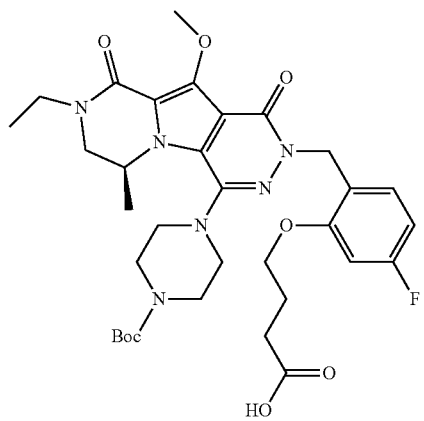

I-139

Intermediate I-138 (0.66 mmol) was dissolved in methanol (5 ml) and THF (5 ml). An aqueous solution of NaOH (1.3 mmol; 5 ml) was added. The mixture was stirred for 1 h at 15° C. The mixture was extracted with methyl tert-butyl ether (20 ml). The aqueous layer was adjusted to pH 3-4 by aqueous saturated citric acid and the resulting mixture was extracted by ethyl acetate (2×20 ml). The combined organic layers were washed with brine and dried over Na₂SO₄. The solvent was removed under vacuum. Yield: 0.49 g (crude, purity 88%).

Example 137

Intermediate I-140

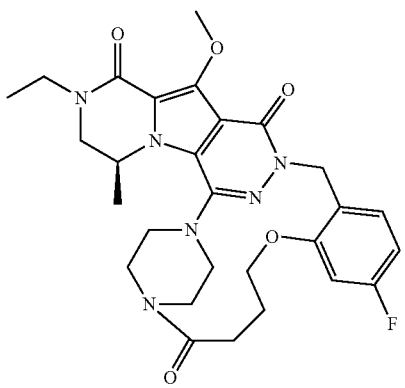

I-140

Intermediate I-140 was obtained following analogous procedures as described in Example 74, and Example 103, using Intermediate I-139.

Example 138

Intermediate I-141

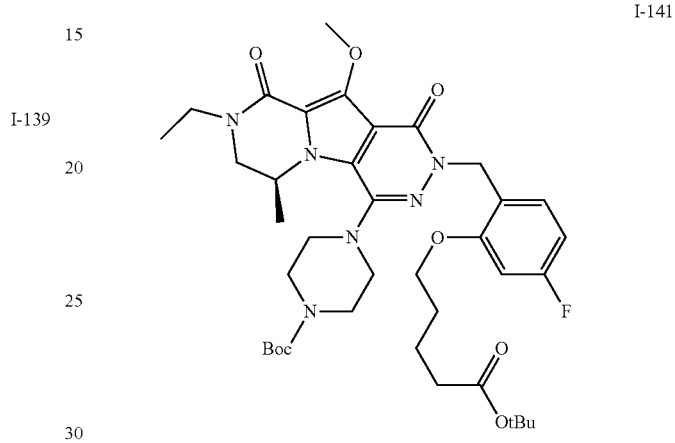

I-141

Intermediate I-141 was obtained following an analogous procedure as described in Example 135, using Intermediate I-137 and tert butyl 5-bromopentanoate.

Example 139

Intermediate I-142

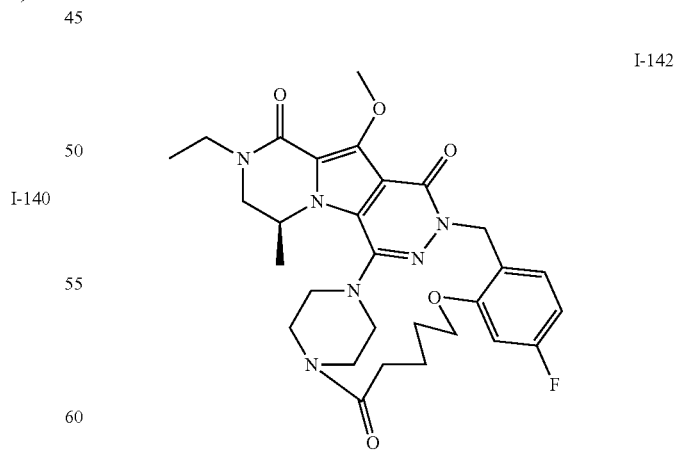

I-142

Intermediate I-142 was obtained following analogous procedures as described in Examples 102-103, using Intermediate I-141.

Example 140

Intermediate I-144

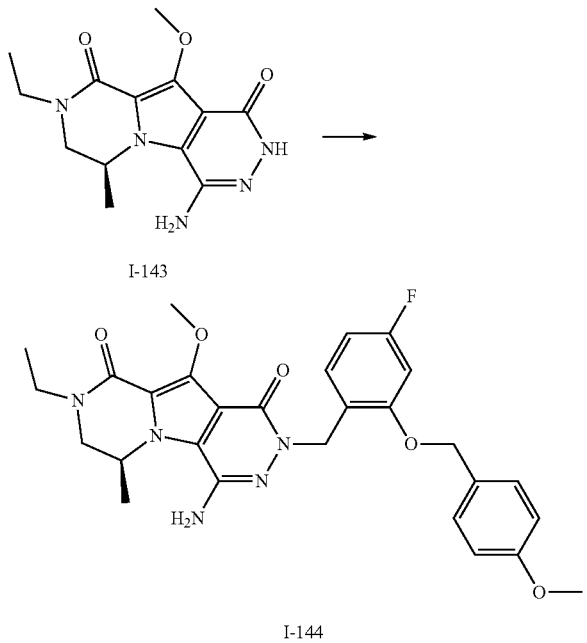

To a solution of tricyclic amine I-143 (12 mmol) in DMF (100 ml), LiHMDS (1 M in THF; 16 mmol) was added at 0° C. The mixture was stirred for 0.5 h and then was treated with Intermediate I-41 (15 mmol) in one portion. The mixture was allowed to warm to 20° C. and was stirred overnight. The solvent was removed under vacuum. The residue was dissolved in CH$_2$Cl$_2$ (50 ml) and the solution was washed with 1 M HCl solution (50 ml) and brine and dried over Na$_2$SO$_4$. The solvent was removed under vacuum. The residue was purified by HPLC(C18; eluent: methanol/H$_2$O from 15:85 to 45:55 with 0.1% TFA as buffer). The pure fractions were collected and the volatiles were removed under vacuum and the aqueous solution was basified with saturated aqueous NaHCO$_3$ to pH 8 and extracted with CH$_2$Cl$_2$ (2×50 ml). The combined organic layers were washed with brine and dried over Na$_2$SO$_4$. The solvent was removed under vacuum. Yield: 2.27 g (35% yield).

Example 141

Intermediate I-145

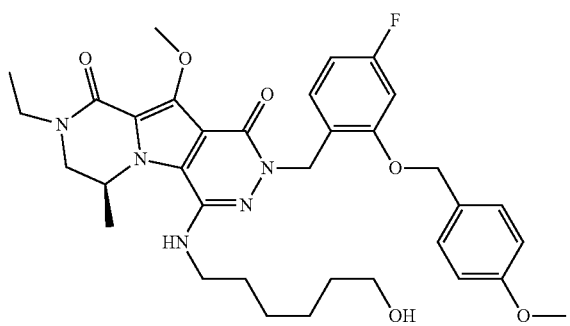

Intermediate I-145 was obtained following an analogous procedure as described in Example 120, using Intermediates I-144 and 6-hydroxyhexanal.

Example 142

Intermediate I-146

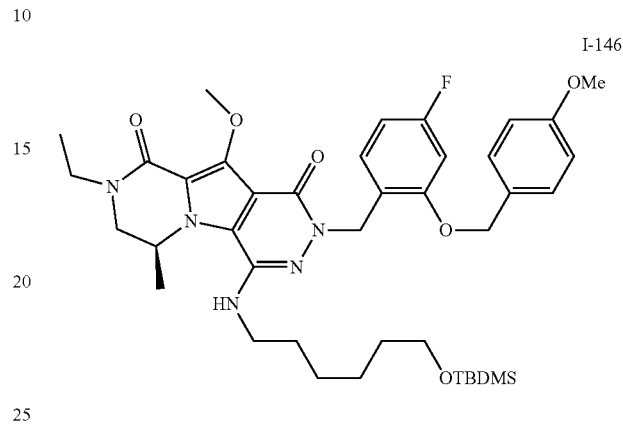

A mixture of Intermediate I-145 (1.4 mmol), tert-butylchlorodimethylsilane (TBDMSCl; 14 mmol) and imidazole (20 mmol) in CH$_2$Cl$_2$ (20 ml) was stirred at room temperature for 1 h. The reaction mixture was washed with saturated NaHCO$_3$ solution and brine. The organic layer was concentrated in vacuo. The residue was purified by SiO$_2$ flash column (eluent: CH$_2$Cl$_2$/methanol from 100:0 to 90:10) to give the pure Intermediate I-146. Yield: 1.1 g (80% yield).

Example 143

Intermediate I-147

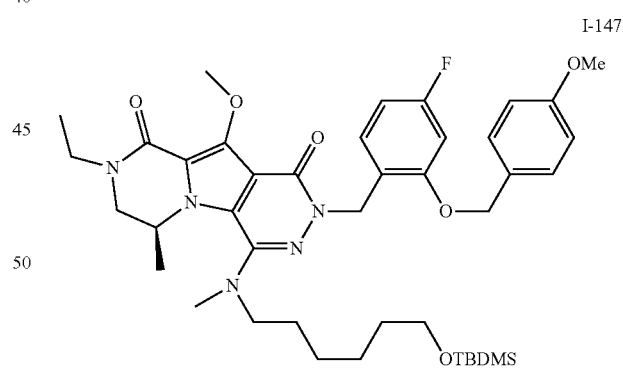

Intermediate I-146 (1.5 mmol) was dissolved in dry THF (10 ml). NaH (60%; 2.3 mmol) was added at 0° C. The mixture was stirred at 0° C. for 15 min. Iodo methane (2.3 mmol) was added dropwise and the mixture was stirred for 40 min at 15° C. The mixture was quenched with saturated aqueous NH$_4$Cl and the solvent was removed under vacuum. The mixture was extracted with CH$_2$Cl$_2$ (2×20 ml). The combined organic layers were washed with brine and dried over Na$_2$SO$_4$. The solvent was removed under vacuum. The residue was purified by SiO$_2$ flash column (eluent: CH$_2$Cl$_2$/methanol from 100:0 to 90:10) to give the pure Intermediate I-147. Yield: 0.6 g (80% yield).

Example 144

Intermediate I-148

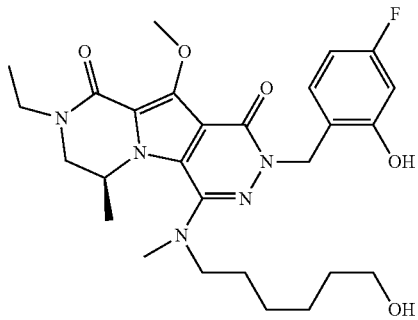

I-148

Intermediate I-148 was obtained following an analogous procedure as described in Example 74, using Intermediate I-147.

Example 145

Intermediate I-149

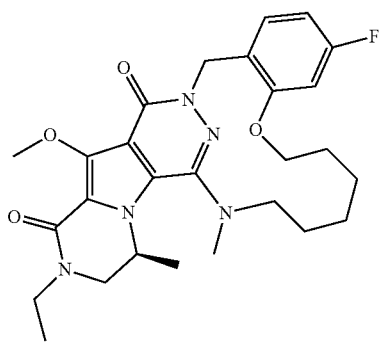

I-149

Intermediate I-149 was obtained following an analogous procedure as described in Example 75, using Intermediate I-148.

Example 146

Intermediate I-150

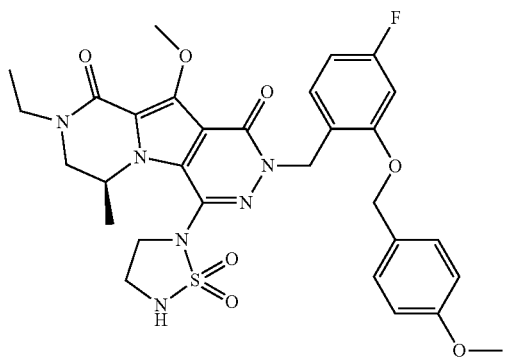

I-150

Intermediate I-150 was obtained following an analogous procedure as described in Example 72, using Intermediate I-72 and 1,2,5-thiadiazolidine, 1,1-dioxide.

Example 147

Intermediate I-151

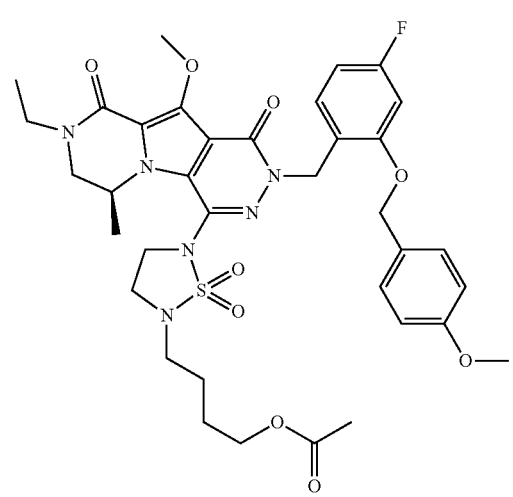

I-151

Intermediate I-151 (1.4 mmol) was dissolved in DMF (15 ml). NaH (60%; 2.8 mmol) was added and the mixture was stirred for 30 min. 4-Bromobutyl acetate (2.1 mmol) was added and the mixture was stirred at 100° C. for 5 h. 10% NH$_4$Cl and ethyl acetate were added. The organic layer was washed with brine for three times and dried over Na$_2$SO$_4$. The solvent was removed under vacuum. The residue was washed with petroleum ether. Yield 1.1 g (70% purity).

Example 148

Intermediate I-152

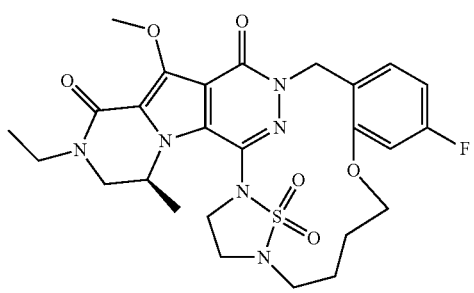

I-152

Intermediate I-152 was obtained following analogous procedures as described in Example 80, and Examples 74-75, using Intermediate I-151.

Example 149

Intermediate I-153

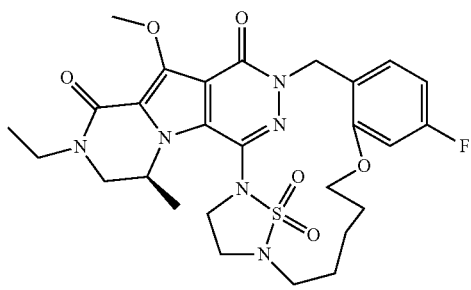

Intermediate I-153 was obtained following analogous procedures as described in Example 147, Example 80, and Examples 74-75, using 5-bromopentyl acetate and Intermediate I-150.

Example 150

Intermediate I-154

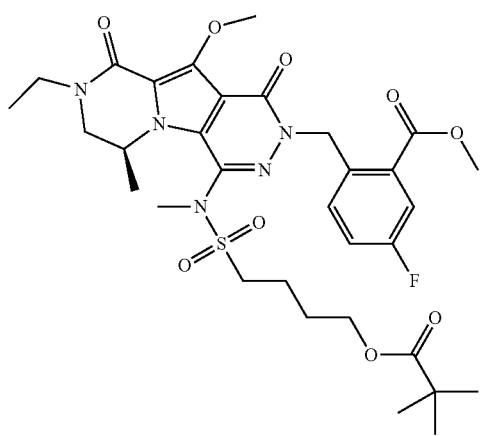

Intermediate I-154 was obtained following an analogous procedure as described in Example 95, using Intermediates I-96 and I-45.

Example 151

Intermediate I-155

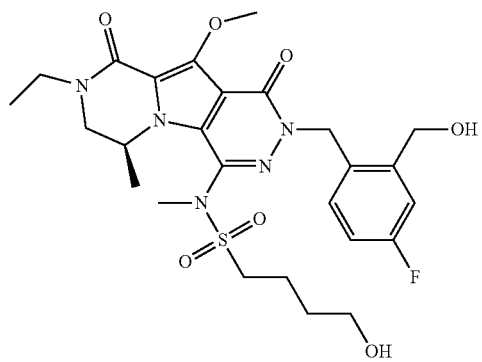

Intermediate I-154 (16.6 mmol) and NaBH$_4$ (166 mmol) were suspended in THF (225 ml). The resulting mixture was stirred for 15 min at 65° C. Methanol (90 ml) was added dropwise during 0.5 h. Stirring at 65° C. was maintained overnight. The reaction was cooled to 15° C., and quenched with a saturated aqueous NH$_4$Cl solution (200 ml). The organic layer was separated and the aqueous layer was extracted with ethyl acetate (3×200 ml). The combined organic layers were washed with brine and dried over Na$_2$SO$_4$. The solvent was removed under vacuum. The residue was purified by SiO$_2$ flash column (gradient eluent: CH$_2$Cl$_2$/methanol 100:0 to 90:10). Yield: 5.5 g (90% purity; 57% yield).

Example 152

Intermediate I-156

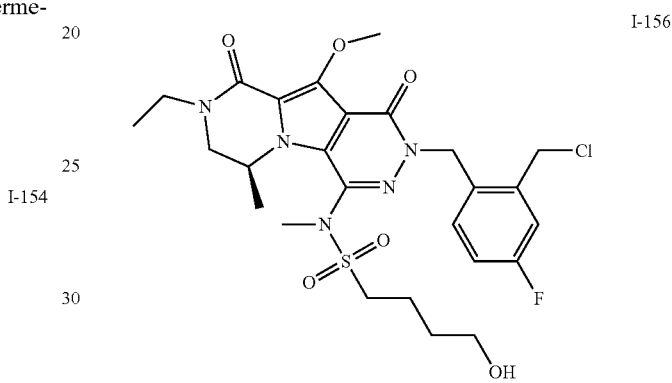

Intermediate I-155 (6.9 mmol) and triethyl amine (21 mmol) in CH$_2$Cl$_2$ (60 ml) was cooled to 0° C. Para toluene sulfonylchloride (7.6 mmol) was added at 0° C. The mixture was stirred for 2 h at 0° C. Then, another batch of para toluene sulfonylchloride (0.13 g) was added at 0° C. The mixture was stirred overnight at 20° C. Saturated aqueous NaHCO$_3$ (30 ml) was added and the organic layer was separated and dried over Na$_2$SO$_4$. The solvent was removed under vacuum. The residue was purified by HPLC(C18, eluent: methanol/H$_2$O from 15:85 to 45:55 with 0.1% TFA as buffer). The pure fractions were collected and the volatiles were removed under vacuum. Then the aqueous solution was basified by saturated aqueous NaHCO$_3$ to pH 7-8 and extracted by CH$_2$Cl$_2$ (120 ml). The combined organic layers were washed by brine and dried over Na$_2$SO$_4$. The solvent was removed under vacuum. Yield: 1.36 g (98% purity; 33% yield).

Example 153

Intermediate I-157

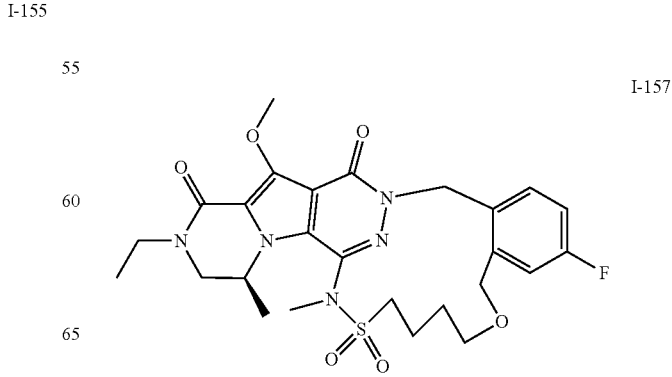

Intermediate I-156 (2.0 mmol) was dissolved in dimethylacetamide (DMA; 25 ml). Potassium tert-butoxide (2.1 mmol) was added portion wise at 0° C. The mixture was stirred at 0° C. for 1 h. The reaction mixture was poured into saturated aqueous citric acid (25 ml) and extracted with $CH_2Cl_2$ (2×50 ml). The combined organic layers were washed with brine and dried over $Na_2SO_4$. The solvent was removed under vacuum. The residue was purified with $SiO_2$ flash column (gradient eluent: $CH_2Cl_2$/methanol 100:0 to 10:1). The obtained compound was further purified by HPLC (C18, eluent: methanol/$H_2O$ from 15:85 to 45:55 with 0.1% TFA as buffer). The pure fractions were collected and the volatiles were removed under vacuum. Then the aqueous solution was basified with saturated aqueous $NaHCO_3$ to pH 7-8 and it was extracted with $CH_2Cl_2$ (2×20 ml). The combined organic layers were washed with brine and dried over $Na_2SO_4$. The solvent was removed under vacuum. Yield: 0.17 g (95% purity; 15% yield).

Example 154

Intermediate I-158

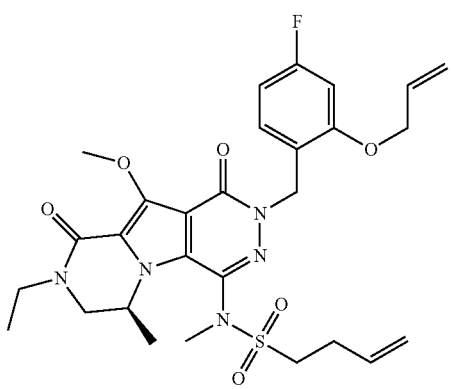

I-158

Intermediate I-158 was obtained following an analogous procedure as described in Examples 71 and 72, using the products obtained in Example 1, Example 41 and Example 52.

Example 155

Intermediate I-159

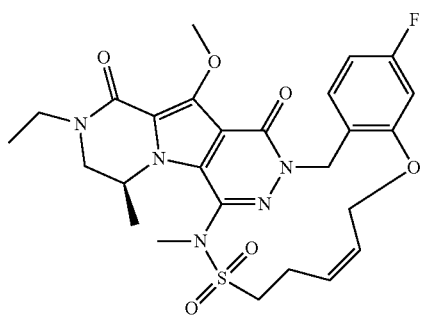

I-159

Intermediate I-158 (1.4 mmol) and 1,3-Bis-(2,4,6-trimethyl-phenyl)-2-imidazolidinylidene)(dichlorophenylmethylene) (tricyclohexylphosphine)ruthenium (0.14 mmol) in dry $CH_2Cl_2$ (200 ml) was stirred and refluxed for 2.5 h. The mixture was evaporated. The residue was purified with flash column chromatography over silica gel (eluent: petroleum ether/ethyl acetate 100:1 to 1:100). The pure fractions were collected and the organic solvent was evaporated to obtain 700 mg as a mixture of isomers. The mixture was purified by SFC separation (column: ChiralPak AS, 5 µm, Daicel Chemical Industries, Ltd 250×20 mm I.D.; mobile phase: A: Supercritical $CO_2$, B: Isopropanol, A/B 75:25 at 50 ml/min) The pure fractions were collected and the solvent was concentrated under vacuum to afford 400 mg of an isomeric mixture (57% yield), that contained two peaks present by SFC analysis. This mixture was further purified by SFC separation (Column: ChiralPak AS, 5 µm, Daicel Chemical Industries, Ltd 250×20 mm I.D.; mobile phase: A: Supercritical $CO_2$, B: Isopropanol, A/B 70:30 at 40 ml/min) The pure fractions were collected and the solvent was concentrated under vacuum. Yield: 0.10 g.

Example 156

Intermediate I-160

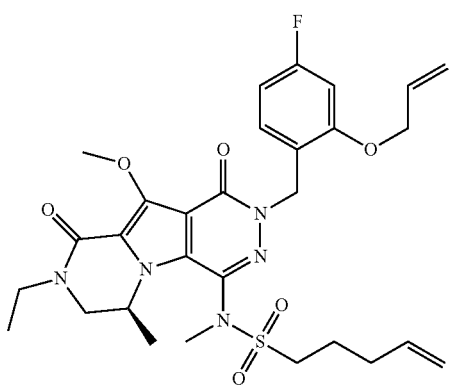

I-160

Intermediate I-160 was obtained following an analogous procedure as described in Examples 71 and 72, using the products obtained in Example 1, Example 41 and Example 53.

Example 157

Intermediate I-161 (Z-isomer) and Intermediate I-162 (E-isomer)

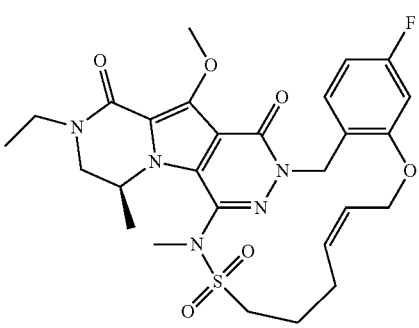

I-161

-continued

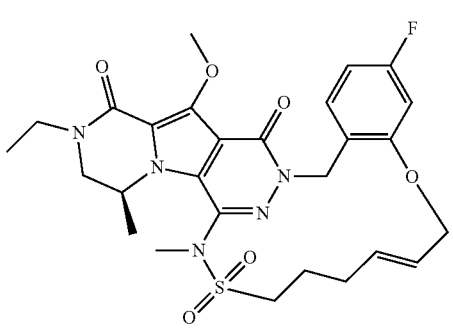

I-162

Intermediate I-160 (1.7 mmol) and Hoveyda-Grubb's 2nd generation catalyst 1,3-Bis-(2,4,6-trimethylphenyl)-2-imidazolidinylidene)dichloro(o-isopropoxyphenylmethylene)ruthenium (0.17 mmol) in dry $CH_2Cl_2$ (200 ml) was stirred and refluxed for 2.5 h under a $N_2$ atmosphere. The mixture was evaporated. The residue was purified with flash column chromatography over silica gel (eluent: petroleum ether/ethyl acetate 100:1 to 1:100). The pure fractions were collected and the organic solvent was evaporated to obtain 0.8 g as a mixture of isomers. This mixture was purified by SFC separation (column: ChiralPak AD, 5 μm, Daicel Chemical Industries, Ltd 250×30 mm I.D.; mobile phase: A: Supercritical $CO_2$, B: methanol, A/B 60:40 at 40 ml/min) The pure fractions were collected and the solvent was concentrated under vacuum to obtain Intermediate I-161 (0.4 g) and Intermediate I-162 (0.1 g).

Example 158

Compound 1 (Deprotection Method A)

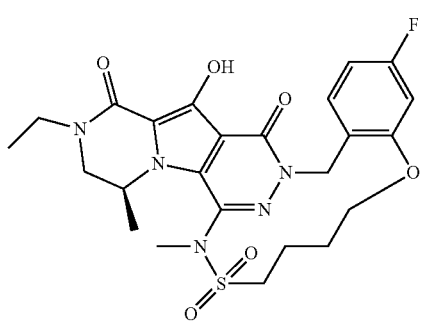

1

Intermediate I-76 (45.7 mmol) and LiCl (457 mmol) in DMF (250 ml) were stirred for 3 h at 140° C. Water was added. The mixture was extracted with $CH_2Cl_2$ (2×500 ml). The combined organic layers were washed with $H_2O$ (2×500 ml), 10% citric acid (500 ml), and brine (2×500 ml), dried over $Na_2SO_4$ and evaporated under vacuum. The residue was triturated with tert-butyl methyl ether (200 ml). The precipitate was collected by filtration and then dissolved in refluxing $CH_3CN$ (120 ml). The mixture was slowly allowed to cool to 20° C. The solid was filtered, dried under high vacuum at 45° C. for 2 h. Then the solid was suspended in $CH_3CN$ (50 ml) and refluxed for 30 min and then stirred at 0° C. for 15 min. The mixture was filtered. The precipitate was dried in vacuum oven at 45° C. overnight. The resulting product was suspended in $CH_3CN$ (30 ml) and then the mixture was stirred at 20° C. overnight. The mixture was filtered. The collected precipitate was dried under high vacuum at 20° C. for 1 h.
Yield: 10 g Compound 1 (41% yield).
e.e.: 100%.

CHN monohydrate (% based on theoretical amount): C, 52.26 (99.02%); H, 5.48 (97.23%); N, 12.70 (99.21%).
Optical rotation: α (589 nm, 20° C.)=−64.93 (solvent: $CH_2Cl_2$, c=5.06 mg/ml)

Example 159

Compounds 2a and 2b (Stable Rotamers)

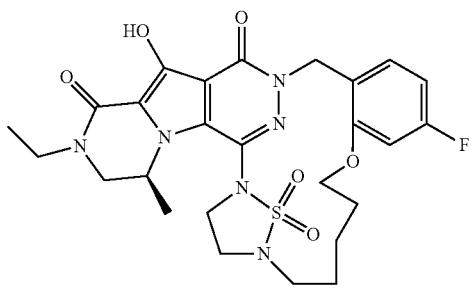

2

Compounds 2a and 2b were obtained following an analogous procedure as described for Compound 1, using Intermediate I-153. Analytical supercritical fluid chromatography revealed two baseline separated peaks, that were separated preparatively using supercritical fluid chromatography (SFC; Column. AD 250 mm×20 mm, 20 nm, Mobile phase: A: Supercritical $CO_2$, B: propan-2-ol, A/B 45:55 at 80 ml/min, Wavelength: 220 nm).
Yield 20 mg Compound 2a as fast moving isomer;
SFC: 99% pure
Yield 30 mg Compound 2b as slow moving isomer;
SFC: 96.6% pure Example 160

Compound 3 (Deprotection Method B)

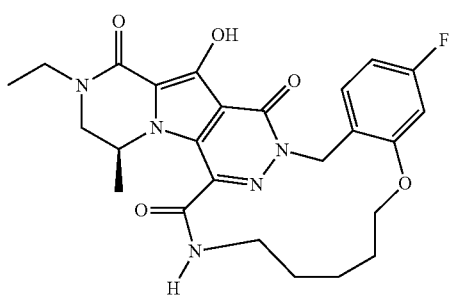

3

Intermediate I-105 (90 mmol) and NaI (174 mmol) were dissolved in a mixture of $CH_3CN$ (760 ml) and toluene (760 ml) at 30° C. Tetrachloro silane (174 mmol) was added dropwise at 0° C. The mixture was stirred for 2 h at 30° C. Then, the mixture was poured into the ice. $CH_2Cl_2$ (1500 ml) and water (1500 ml) were added. The organic layers were collected and washed with 10% $NaHCO_3$, 10% citric acid, 10% $Na_2SO_3$, 2 N HCl, then by brine. The resulting organic layer was dried over $Na_2SO_4$ and filtrated. The solvent was removed under vacuum. The resulting residue was washed with tert-butyl methyl ether and methanol. The resulting crude product was then re-crystallized from $CH_3CN$ (30 g product/300 ml of $CH_3CN$).
Yield: 18 g Compound 3 (40%, yield).
% ee by SFC-MS: 99.99%
CHN (% based on theoretical amount: C, 60.49 (100.2%). H, 5.525 (97.4%). N, 14.44 (102.6%).
Optical rotation: (589 nm, 20° C.): 53.05 (c=9.61 mg/ml, CH2Cl2)

Example 161

Compound 4 (Deprotection Method C)

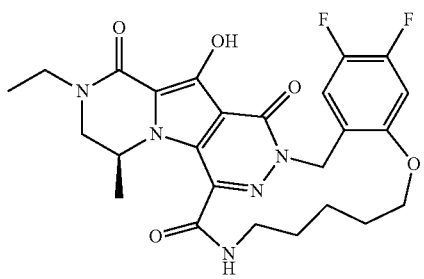

To a solution of Intermediate I-107 (0.56 mmol) in CH$_2$Cl$_2$ (25 ml), BBr$_3$ (5.6 mmol, as a 1 M solution in CH$_2$Cl$_2$) was added dropwise at −78° C. The mixture was allowed to warm to 15° C. and was stirred for 0.5 h. Water (10 ml) was added. The organic layer was separated and the aqueous layer was extracted with CH$_2$Cl$_2$ (2×30 ml). The combined organic layers were washed with brine and dried over Na$_2$SO$_4$. The solvent was removed under vacuum. The residue was purified by HPLC(C18, eluent: methanol/H$_2$O from 15:85 to 45:55 with 0.1% TFA as buffer). The pure fractions were collected and the volatiles were removed under vacuum and the aqueous solution was basified with NaHCO$_3$ to pH 8 and extracted with CH$_2$Cl$_2$ (2×80 ml). The combined organic layers were washed with brine and dried over Na$_2$SO$_4$. The solvent was removed under vacuum.

Yield: 45 mg Compound 4 (99% purity; 20% yield)
ee by SFC-MS: 100%

Example 162

Reference Compounds 52r, 53r and 54r

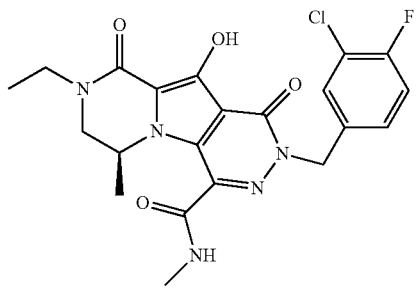

Compound 52r, also known as MK-2048, has been described in Vacca, J. P., J. S. Wai, et al. (2007; Discovery of MK-2048: subtle changes confer unique resistance properties to a series of tricyclic hydroxypyrrole integrase strand transfer inhibitors. 4th International AIDS Society (IAS) Conference, Sydney, Australia).

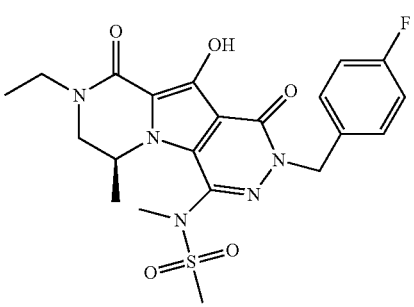

Compound 53r has been described in WO2005110414 (example number 159-A).

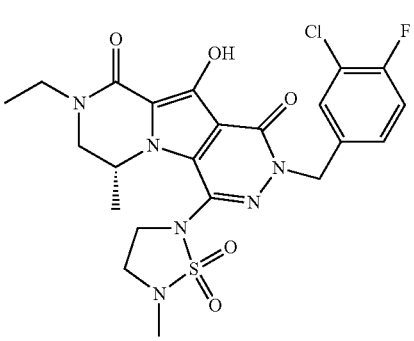

Compound 54r has been described in Wai, J. S., T. E. Fisher, et al. (2007; Next Generation of Inhibitors of HIV-1 Integrase Strand Transfer Inhibitor: Structural Diversity and Resistance Profiles. CROI, Los Angeles, Calif.).

TABLE 1

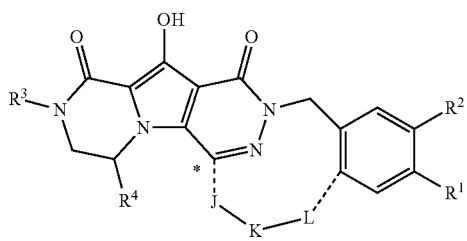

| Co. No. | *-J-K-L- | R$^1$ | R$^2$ | R$^3$ | R$^4$ | From intermediate (Deprotection Method) |
|---|---|---|---|---|---|---|
| 41 |  | F | H | / | (S)-Me | I-127 (C) |

TABLE 1-continued

| Co. No. | *-J-K-L- | R¹ | R² | R³---- | R⁴ | From intermediate (Deprotection Method) |
|---|---|---|---|---|---|---|
| 3 | *-C(=O)-NH-(CH₂)₄-O-* | F | H | / ---- | (S)-Me | I-105 (B) |
| 40 | HN-(CH₂)₅-NH-C(=O)-* | F | H | / ---- | (S)-Me | I-126 (C) |
| 24 | *-C(=O)-NH-(CH₂)₃-O-* | F | H | / ---- | (S)-Me | I-106 (C) |
| 30 | *-C(=O)-N(Me)-(CH₂)₃-O-* | F | H | / ---- | (S)-Me | I-113 (C) |
| 22 | *-N(Me)-SO₂-(CH₂)₃-NH-C(=O)-* | F | H | / ---- | (S)-Me | I-101 (C) |
| 31 | *-C(=O)-N(Me)-(CH₂)₄-O-* | F | H | / ---- | (S)-Me | I-114 (C) |
| 21 | *-N(Me)-SO₂-(CH₂)₄-NH-C(=O)-* | F | H | / ---- | (S)-Me | I-100 (C) |
| 39 | HN-(CH₂)₃-NH-C(=O)-* | F | H | / ---- | (S)-Me | I-124 (C) |
| 43 | *-N(Me)-(CH₂)₅-NH-C(=O)-* | F | H | / ---- | (S)-Me | I-131 (B) |
| 26 | *-C(=O)-NH-(CH₂)₄-O-* | F | Cl | / ---- | (S)-Me | I-109 (C) |

TABLE 1-continued

| Co. No. | *-J-K-L- | R¹ | R² | R³---- | R⁴ | From intermediate (Deprotection Method) |
|---|---|---|---|---|---|---|
| 33 | *-C(=O)-N(Et)-(CH₂)₄-O- | F | Cl | /---- | (S)-Me | I-116 (B) |
| 42 | *-NH-(CH₂)₅-N(Me)-C(=O)- | F | H | /---- | (S)-Me | I-128 (C) |
| 25 | *-C(=O)-NH-(CH₂)₄-O- | Cl | H | /---- | (S)-Me | I-108 (B) |
| 32 | *-C(=O)-N(Me)-(CH₂)₄-O- | F | Cl | /---- | (S)-Me | I-115 (B) |
| 36 | *-C(=O)-NH-(CH₂)₄-O- | F | H | ▷---- | (S)-Me | I-119 (B) |
| 27 | *-C(=O)-NH-(CH₂)₄-O- | F | H | /---- | H | I-110 (B) |
| 28 | *-C(=O)-NH-(CH₂)₄-O- | F | H | H₃C---- | (S)-Me | I-111 (B) |
| 29 | *-C(=O)-NH-(CH₂)₄-O- | F | H | iPr---- | (S)-Me | I-112 (B) |
| 37 | *-C(=O)-N(Me)-(CH₂)₄-O- | F | H | ▷---- | (S)-Me | I-120 (B) |
| 38 | *-C(=O)-N(Me)-(CH₂)₄-O- | F | H | /---- | H | I-121 (B) |

TABLE 1-continued
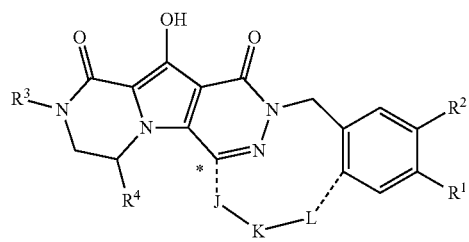
| Co. No. | *-J-K-L- | R¹ | R² | R³ ---- | R⁴ | From intermediate (Deprotection Method) |
|---|---|---|---|---|---|---|
| 5 | *-N(Me)-SO₂-(CH₂)₄-O--- | F | H | / ---- | (S)-Me | I-77 (A and B) |
| 35 | *-C(O)-N(Me)-(CH₂)₄-O--- | F | H | >---- | (S)-Me | I-118 (B) |
| 1 | *-N(Me)-SO₂-(CH₂)₃-O--- | F | H | / ---- | (S)-Me | I-76 (A) |
| 23 | *-N(Me)-SO₂-(CH₂)₃-NH-C(O)--- | F | H | / ---- | (S)-Me | I-102 (C) |
| 8 | *-N(Me)-SO₂-(CH₂)₂-O--- | F | H | / ---- | (S)-Me | I-82 (C) |
| 9 | *-N(Me)-SO₂-CH(S)(Me)-(CH₂)₃-O--- | F | H | / ---- | (S)-Me | I-83 (B) |
| 7 | *-N(Me)-SO₂-(CH₂)₄-O--- | F | H | >---- | (S)-Me | I-79 (A) |
| 47 | *-N-SO₂-N-(CH₂)₄-O--- (cyclic) | F | H | / ---- | (S)-Me | I-152 (A) |
| 10 | *-N(Me)-SO₂-CH(R)(Me)-(CH₂)₃-O--- | F | H | / ---- | (S)-Me | I-83 (B) |

TABLE 1-continued

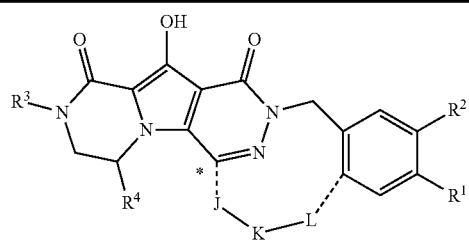

| Co. No. | *-J-K-L- | R¹ | R² | R³ | R⁴ | From intermediate (Deprotection Method) |
|---|---|---|---|---|---|---|
| 2b | N-S(O₂)-N-CH₂CH₂-O (ring) with pentyloxy chain | F | H | (isopropyl-like) | (S)-Me | I-153 (A) |
| 2a | N-S(O₂)-N-CH₂CH₂-O (ring) with pentyloxy chain | F | H | (isopropyl-like) | (S)-Me | I-153 (A) |
| 46 | Me-N-(CH₂)₅-O | F | H | (isopropyl-like) | (S)-Me | I-149 (A) |
| 6 | Me-N-SO₂-(CH₂)₄-O | F | H | (isopropyl) | (S)-Me | I-78 (A) |
| 4 | O=C(NH)-(CH₂)₅-O | F | F | (isopropyl-like) | (S)-Me | I-107 (C) |
| 11 | Et-N-SO₂-(CH₂)₄-O | F | H | (isopropyl-like) | (S)-Me | I-84 (A) |
| 15 | Et-N-SO₂-(CH₂)₅-O | F | H | (isopropyl-like) | (S)-Me | I-88 (A) |
| 34 | O=C-N(Me)-(CH₂)₅-O | F | F | (isopropyl-like) | (S)-Me | I-117 (B) |
| 48 | Me-N-SO₂-(CH₂)₄-O | F | H | (isopropyl-like) | (S)-Me | I-157 (A) |
| 16 | cyclopropyl-N-SO₂-(CH₂)₅-O | F | H | (isopropyl-like) | (S)-Me | I-89 (A) |

TABLE 1-continued

| Co. No. | *-J-K-L- | R¹ | R² | R³ | R⁴ | From intermediate (Deprotection Method) |
|---|---|---|---|---|---|---|
| 13 | (ethyl-N-sulfonyl-butyl-O) | F | H | isopropyl | (S)-Me | I-86 (A) |
| 12 | (cyclopropyl-N-sulfonyl-butyl-O) | F | H | ethyl | (S)-Me | I-85 (A) |
| 20 | (methyl-N-sulfonyl-pentyl-O) | F | F | ethyl | (S)-Me | I-93 (A) |
| 19 | (methyl-N-sulfonyl-butyl-O) | F | F | ethyl | (S)-Me | I-92 (A) |
| 18 | (methyl-N-sulfonyl-pentyl-O) | F | Cl | ethyl | (S)-Me | I-91 (A) |
| 17 | (methyl-N-sulfonyl-butyl-O) | F | Cl | ethyl | (S)-Me | I-90 (A) |
| 14 | (cyclopropyl-N-sulfonyl-butyl-O) | F | H | isopropyl | (S)-Me | I-87 (A) |
| 45 | (piperazine-carbonyl-butyl-O) | F | H | ethyl | (S)-Me | I-142 (A) |

TABLE 1-continued

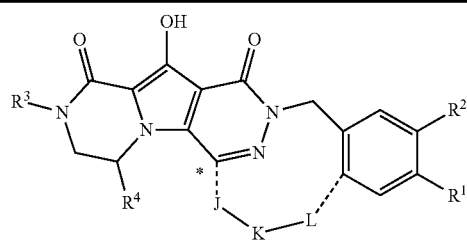

| Co. No. | *-J-K-L- | R¹ | R² | R³ - - - | R⁴ | From intermediate (Deprotection Method) |
|---|---|---|---|---|---|---|
| 44 | *-N(piperazine-C(O)-CH₂CH₂CH₂-O-) | F | H | /---- | (S)-Me | I-140 (A) |
| 51 | *-N(Me)-SO₂-CH₂CH₂CH₂-CH=CH(E)-CH₂-O- | F | H | /---- | (S)-Me | I-162 (A) |
| 49 | *-N(Me)-SO₂-CH₂CH₂CH₂-CH=CH(Z)-O- | F | H | /---- | (S)-Me | I-159 (A) |
| 50 | *-N(Me)-SO₂-CH₂CH₂CH₂-CH=CH(Z)-CH₂-O- | F | H | /---- | (S)-Me | I-161 (A) |

Example 163

LC/MS Analysis

General Procedure for M1 and M2

The HPLC measurement was performed using an Agilent 1100 module comprising a pump, a diode-array detector (DAD) (wavelength used 220 nm), a column heater and a column as specified in the respective methods below. Flow from the column was split to an Agilent MSD Series G1946 C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50V. Drying gas temperature was maintained at 350° C. at a flow of 10 l/min.

Method (M1)

In addition to the general procedure, reversed-phase HPLC was carried out on a YMC-Pack ODS-AQ, 50×2.0 mm 5 μm column with a flow rate of 0.8 ml/min. Two mobile phases (mobile phase A: water with 0.1% TFA; mobile phase B: CH₃CN with 0.05% TFA) were used. First, 100% A was hold for 1 minute. Then a gradient was applied to 40% A and 60% B in 4 minutes and hold for 2.5 minutes. Typical injection volumes of 2 μl were used. Oven temperature was 50° C. (MS polarity: positive)

Method (M2)

In addition to the general procedure, reversed-phase HPLC was carried out on a YMC-Pack ODS-AQ, 50×2.0 mm 5 μm column with a flow rate of 0.8 ml/min. Two mobile phases (mobile phase A: water with 0.1% TFA; mobile phase B: CH₃CN with 0.05% TFA) were used. First, 90% A and 10% B was hold for 0.8 minutes. Then a gradient was applied to 20% A and 80% B in 3.7 minutes and hold for 3 minutes. Typical injection volumes of 2 μl were used. Oven temperature was 50° C. (MS polarity: positive)

Method (M3)

The LC measurement was performed using an Acquity HPLC (Ultra Performance Liquid Chromatography, Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system. Reversed-phase HPLC was carried out on a bridged ethylsiloxane/silica hybrid (BEH) C18 column (1.7 nm, 2.1×50 mm; Waters Acquity) with a flow rate of 0.8 ml/min. Two mobile phases (25 mM ammonium acetate in $H_2O$/acetonitrile 95:5; mobile phase B: acetonitrile) were used to run a gradient condition from 95% A and 5% B to 5% A and 95% B in 1.3 minutes and hold for 0.3 minutes. An injection volume of 0.5 µl was used.

Cone voltage was 10 V for positive ionization mode and 20 V for negative ionization mode.

Example 164

Determination of Melting Points

DSC

For a number of compounds, melting points were determined with a DSC823e (Mettler-Toledo). Melting points were measured with a temperature gradient of 30° C./minute. Maximum temperature was 400° C.

WRS-2A

For a number of compounds, melting points were determined with a WRS-2A melting point apparatus that was purchased from Shanghai Precision and Scientific Instrument Co. Ltd. Melting points were measured with a linear heating up rate of 0.2-5.0° C./minute. The reported values are melt ranges. The maximum temperature was 300° C.

TABLE 2

LC/MS and melting points

| Co. No. | LC/MS Rt | LC-MS $[M + H]^+$ | Melting point ° C. |
|---|---|---|---|
| 1 | 5.51 (M1) | 534 | 298.6-300.6 (DSC) |
| 2b | 5.78 (M1) | 575 | 214.38-227.03 (DSC) |
| 2a | 5.76 (M1) | 575 | >280.00 (WRS-2A) |
| 3 | 4.37 (M2) | 498 | 128.21 (DSC) |
| 4 | 5.54 (M1) | 516 | 127.49-128.63 (DSC) |
| 5 | 5.63 (M1) | 548 | 233.93-238.55 (DSC) |
| 6 | 5.96 (M1) | 548 | 240.00-245.21 (DSC) |
| 7 | 6.09 (M1) | 562 | 267.04-270.76 (DSC) |

TABLE 2-continued

LC/MS and melting points

| Co. No. | LC/MS Rt | LC-MS $[M + H]^+$ | Melting point ° C. |
|---|---|---|---|
| 8 | 0.92 (M3) | 520 | 273.80 |
| 10 | 1.08 (M3) | 562 | |
| 11 | 5.57 (M1) | 548 | >229.40 (decompose, WRS-2A) |
| 12 | 5.8 (M1) | 560 | >280.00 (WRS-2A) |
| 14 | | 574 | 296.76-304.35 (DSC) |
| 15 | 5.68 (M1) | 562 | 244.87-248.94 (DSC) |
| 16 | 1.08 (M3) | 574 | |
| 17 | | 568 | 220.73233.03 (DSC) |
| 18 | 6.19 (M1) | 582 | 206.71-224.90 (DSC) |
| 19 | 4.04 (M2) | 552 | 264.43-269.61 (DSC) |
| 20 | 6.1 (M1) | 566 | 245.95-251.27 (DSC) |
| 22 | | | 236.20 (DSC) |
| 23 | 0.73 (M3) | 547 | |
| 24 | 5.22 (M1) | 484 | 267.14 (DSC) |
| 25 | 6.06 (M1) | 514 | 166.74-181.43 (DSC) |
| 26 | 1.1 (M3) | 532 | |
| 27 | 5.55 (M1) | 484 | >280.00 (WRS-2A) |
| 28 | 4.26 (M1) | 484.1 | 246.80-250.50 (WRS-2A) |
| 30 | | | 243.57 (DSC) |
| 31 | 5.62 (M1) | 512 | 219.47 (DSC) |
| 32 | 5.96 (M1) | 546 | 280.72-286.60 (DSC) |
| 33 | 6.19 (M1) | 560 | 256.56-265.21 (DSC) |
| 34 | 5.467 (M1) | 530 | 263.81-266.46 (DSC) |
| 36 | 5.77 (M1) | 510 | 215.09-228.19 (DSC) |
| 37 | 6.3 (M1) | 524.2 | 229.30 (decomposed, WRS-2A) |
| 39 | 0.65 (M3) | 469 | |
| 40 | 4.97 (M1) | 497 | 179.18 (DSC) |
| 41 | 5.19 (M1) | 511 | 181.32-197.63 (DSC) |
| 42 | 5.41 (M1) | 525 | 207.5-218.1 (WRS-2A) |
| 43 | 0.99 (M3) | 525 | |
| 44 | 5.02 (M1) | 539 | 212.04-218.62 (DSC) |
| 45 | 5.32 (M1) | 553 | >280.00 (WRS-2A) |
| 46 | 4.92 (M2) | 498 | 71.40-114.20 (WRS-2A) |
| 47 | 1 (M3) | 561 | 290.52 |
| 48 | 0.96 (M3) | 548 | |

Example 165

Determination of NMR Spectra $^1$H spectra were recorded on a Bruker AVANCE III (400 MHz), a Bruker AVANCE (600 MHz) or on a Varian 400-MR (400 MHz) spectrometer.

TABLE 3

NMR data

| Co. No. | NMR |
|---|---|
| 1 | $^1$H NMR (400 MHz, CHLOROFORM-d) δ ppm 1.21 (t, J = 7.1 Hz, 3 H), 1.37 (d, J = 6.7 Hz, 3 H), 1.80-1.92 (m, 1 H), 2.06-2.26 (m, 2 H), 2.76-2.92 (m, 1 H), 3.18-3.27 (m, 2 H), 3.36 (ddd, J = 14.1, 12.5, 5.7 Hz, 1 H), 3.49 (s × t, J = 7.00 Hz, 1 H), 3.47 (s, 3 H), 3.66 (s × t, J = 7.1 Hz, 1 H), 3.76 (td, J = 10.3, 3.6 Hz, 1 H), 3.96 (dd, J = 13.1, 4.02 Hz, 1 H), 4.13 (ddd, J = 9.3, 5.4, 3.5 Hz, 1 H), 5.09 (d, J = 13.3 Hz, 1 H), 5.35-5.42 (m, 1 H), 5.43 (d, J = 13.38 Hz, 1 H), 6.52 (dd, J = 10.9, 2.5 Hz, 1 H), 6.64 (td, J = 8.3, 2.4 Hz, 1 H), 7.85 (dd, J = 8.5, 6.9 Hz, 1 H), 8.48 (br. s., 1 H), minor rotamer observed (12%) |
| 2b | $^1$H NMR (600 MHz, CHLOROFORM-d) δ ppm 1.22 (t, J = 7.2 Hz, 3 H), 1.40 (d, J = 6.6 Hz, 3 H), 1.48-1.56 (m, 1 H), 1.66-1.75 (m, 4 H), 2.01-2.10 (m, 1 H), 3.03 (d, J = 12.6 Hz, 1 H), 3.05-3.10 (m, 1 H), 3.27 (d, J = 13.0 Hz, 1 H), 3.35-3.44 (m, 1 H), 3.47-3.55 (m, 1 H), 3.62-3.69 (m, 1 H), 3.69-3.74 (m, 1 H), 3.84-3.90 (m, 1 H), 3.90-3.94 (m, 1 H), 4.00 (dt, J = 8.3, 4.2 Hz, 1 H), 4.04 (dd, J = 13.0, 4.2 Hz, 1 H), 5.05-5.11 (m, 1 H), 5.13 (d, J = 13.5 Hz, 1 H), 5.28 (d, J = 13.6 Hz, 1 H), 6.55 (dd, J = 11.0, 2.6 Hz, 1 H), 6.62 (td, J = 8.3, 2.2 Hz, 1 H), 7.54 (t, J = 7.6 Hz, 1 H), 8.35-8.61 (m, 1 H) |

TABLE 3-continued

NMR data

| Co. No. | NMR |
|---|---|
| 2a | $^1$H NMR (600 MHz, ACETONE-d) δ ppm 1.20 (t, J = 7.2 Hz, 3 H), 1.50 (d, J = 6.6 Hz, 3 H), 1.59-1.66 (m, 1 H), 1.67-1.74 (m, 1 H), 1.76-1.87 (m, 3 H), 2.09-2.17 (m, 1 H), 3.03 (ddd, J = 12.4, 3.7, 3.4 Hz, 1 H), 3.15-3.20 (m, 1 H), 3.36 (td, J = 12.1, 4.3 Hz, 1 H), 3.42-3.49 (m, J = 13.9, 7.1, 7.1, 7.0 Hz, 1 H), 3.57 (dd, J = 13.1, 1.6 Hz, 1 H), 3.71 (dq, J = 13.9, 7.1 Hz, 1 H), 3.78-3.86 (m, 2 H), 3.94-3.98 (m, 1 H), 4.00 (td, J = 9.8, 2.7 Hz, 1 H), 4.04 (dd, J = 13.1, 3.9 Hz, 1 H), 4.16 (ddd, J = 9.1, 4.4, 4.2 Hz, 1 H), 5.09 (d, J = 13.6 Hz, 1 H), 5.37 (d, J = 13.6 Hz, 1 H), 5.39-5.44 (m, J = 6.6, 6.6, 6.6, 3.9, 1.6 Hz, 1 H), 6.63 (td, J = 8.4, 2.5 Hz, 1 H), 6.75 (dd, J = 11.4, 2.5 Hz, 1 H), 7.57 (dd, J = 8.5, 7.0 Hz, 1 H), 8.56-8.94 (m, 1 H) |
| 3 | $^1$H NMR (300 MHz, DMSO-d) δ ppm 1.11 (t, J = 6.8 Hz, 3 H), 1.24 (d, J = 6.4 Hz, 3 H), 1.60-1.77 (m, 6 H), 3.16-3.47 (m, 4 H), 3.57-3.69 (m, 1 H), 3.87-3.92 (dd, J1 = 3.2 Hz, J2 = 13.2 Hz, 1 H), 4.01 (m, 2 H), 5.09 (br s, 1 H), 5.27 (br s, 2 H), 6.68-6.74 (dt, J1 = 2.0 Hz, J2 = 8.4 Hz, 1 H), 6.86-6.91 (dd, J1 = 2.0 Hz, J2 = 11.6 Hz, 1 H), 7.61 (t, J = 7.6 Hz, 1 H), 8.38 (br s, 1 H), 9.11 (br s, 1 H) |
| 4 | $^1$H NMR (400 MHz, CDCl$_3$) δ ppm 1.17 (t, J = 7.2 Hz, 3 H), 1.38 (d, J = 6.6 Hz, 3 H), 1.56-1.80 (m, 6 H), 3.13-3.17 (d, J = 12.8 Hz, 1 H), 3.36-3.38 (br s, 1 H), 3.40-3.42 (m, 1 H), 3.43-3.60 (br s, 1 H), 3.62-3.69 (m, 1 H), 3.88-3.95 (m, 3 H), 5.28 (br s, 2 H), 5.71 (br s, 1 H), 6.70 (q, J = 9.4 Hz, 1 H), 7.16 (m, 1 H), 7.59-7.64 (t, J = 7.2 Hz, 1 H), 8.73 (br s, 1 H). |
| 5 | $^1$H NMR (600 MHz, CHLOROFORM-d) δ ppm 1.18-1.26 (m, 3 H), 1.38 (d, J = 6.7 Hz, 2 H), 1.50 (d, J = 6.5 Hz, 1 H), 1.69-1.82 (m, 2 H), 1.88-1.96 (m, 0.66 H), 1.96-2.07 (m, 1.33 H), 2.09-2.19 (m, 1 H), 2.23-2.33 (m, 0.66 H), 2.37-2.48 (m, 0.33 H), 3.22 (s, 1 H), 3.30 (s, 2 H), 3.36 (ddd, J = 10.5, 5.9, 4.2 Hz, 1.33 H), 3.44-3.59 (m, 1.66 H), 3.66 (s × t, J = 7.1 Hz, 0.66 H), 3.71 (s × t, J = 7.1 Hz, 0.33 H), 3.94-4.00 (m, 1 H), 4.00-4.08 (m, 1 H), 4.10 (ddd, J = 9.4, 6.6, 2.2 Hz, 0.33 H), 4.18 (ddd, J = 10.3, 6.2, 2.7 Hz, 0.66 H), 4.84-4.91 (m, 0.33 H), 5.22 (d, J = 13.6 Hz, 0.33 H), 5.27 (d, J = 13.4 Hz, 0.66 H), 5.29-5.34 (m, 0.66 H), 5.37 (d, J = 13.4 Hz, 0.66 H), 5.43 (d, J = 13.5 Hz, 0.33 H), 6.57 (dd, J = 11.0, 2.49 Hz, 1 H), 6.59-6.64 (m, 1 H), 7.77 (dd, J = 8.5, 6.9 Hz, 0.66 H), 7.85 (dd, J = 8.5, 6.9 Hz, 0.33 H), 8.53 (br. s., 0.66 H), 8.58 (br. s, 0.33 H) |
| 6 | The compound was present as two rotamers in a ratio of 1:9. $^1$H NMR (400 MHz, CDCl$_3$) δ ppm 1.10 (d, J = 6.9 Hz, 3 H), 1.14 (d, J = 6.9 Hz, 3 H), 1.26 (d, J = 6.7 Hz, 2.7 H), 1.40 (d, J = 6.3 Hz, 0.3 H), 1.73-1.85 (m, 0.9 H), 1.88 (br s, 0.1 H), 2.00-2.19 (m, 2 H), 2.61 (br s, 0.1 H), 2.70-2.86 (m, 0.9 H), 3.09-3.35 (m, 3.3 H), 3.40 (s, 2.7 H), 3.43-3.54 (m, 0.2 H), 3.59-3.75 (m, 1.8 H), 4.00-4.10 (m, 1 H), 4.86 (quint, J = 6.7 Hz, 1.1 H), 5.02 (d, J = 13.1 Hz, 0.9 H), 5.09 (d, J = 13.1 Hz, 0.1 H), 5.30-5.40 (m, 1 H), 5.33 (d, J = 13.5 Hz, 0.9 H), 6.44 (dd, J1 = 10.8 Hz, J2 = 2.1 Hz, 0.95 H), 6.48 (m, 0.05 H), 6.57 (dt, J1 = 8.2 Hz, J2 = 2.1 Hz, 1 H), 7.78 (t, J = 7.4 Hz, 1 H), 8.48 (br s, 0.9 H), 8.52 (br s, 0.1 H) |
| 7 | $^1$H NMR (600 MHz, CHLOROFORM-d) δ ppm 1.16-1.24 (m, 6 H), 1.34 (d, J = 6.83 Hz, 2 H), 1.47 (d, J = 6.72 Hz, 1 H), 1.66-1.82 (m, 2 H), 1.87-2.08 (m, 2 H), 2.09-2.20 (m, 1 H), 2.23-2.33 (m, 0.66 H), 2.38-2.48 (m, 0.33 H), 3.21 (s, 0.98 H), 3.30 (dd, J = 13.06, 1.61 Hz, 0.66 H), 3.30 (s, 2 H), 3.33-3.39 (m, 1.65 H), 3.44-3.51 (m, 0.33 H), 3.52-3.59 (m, 0.33 H), 3.72 (dd, J = 12.91, 4.00 Hz, 0.33 H), 3.73 (dd, J = 13.06, 3.96 Hz, 0.66 H), 4.00-4.08 (m, 1 H), 4.10 (ddd, J = 9.17, 6.68, 2.05 Hz, 0.33 H), 4.18 (ddd, J = 10.27, 6.16, 2.64 Hz, 0.66 H), 4.86-4.91 (m, 0.33 H), 4.92-5.01 (m, 1 H), 5.23 (d, J = 13.48 Hz, 0.33 H), 5.27 (d, J = 13.44 Hz, 0.66 H), 5.30-5.36 (m, 0.66 H), 5.39 (d, J = 13.42 Hz, 0.66 H), 5.45 (d, J = 13.43 Hz, 0.33 H), 6.57 (dd, J = 11.00, 2.48 Hz, 1 H), 6.62 (tt, J = 8.22, 2.35 Hz, 1 H), 7.77 (dd, J = 8.53, 6.99 Hz, 0.66 H), 7.86 (dd, J = 8.49, 6.96 Hz, 0.33 H), 8.61 (br. s., 0.66 H), 8.67 (br. s, 0.33 H) |
| 8 | $^1$H NMR (300 MHz, DMSO-d) δ ppm 1.09 (t, J = 7.1 Hz, 3 H), 1.29-1.32 (dd, J = 6.4 Hz, 6.2 Hz, 3 H), 1.85 (m, 1 H), 2.22-2.39 (m, 1 H), 3.27 (s, 3 H), 3.37-3.60 (m, 3 H), 3.66-4.08 (m, 3 H), 4.27-4.37 (m, 3 H), 4.78 (m, 1 H), 5.00 (m, 1 H), 5.02-5.06 (m, 1 H), 5.17-5.34 (m, 2 H), 6.71-6.77 (t, J = 8.4 Hz, 1 H), 6.97-7.00 (d, J = 9.6 Hz, 1 H), 7.45-7.55 (dt, J = 9.2 Hz, 6.8 Hz, 1 H), 9.05 (s, 1H). |
| 10 | The compound was present as two rotamers in a ratio of 50:50. $^1$H NMR (300 MHz, DMSO) δ ppm 1.29 (t, J = 1.8 Hz, 3 H), 1.33-1.41 (m, 6 H), 1.50-1.99 (m, 5.5 H), 2.70 (m, 0.5 H), 3.21 (s, 1.5 H), 3.25 (s, 1.5 H), 3.42 (m, 1.5 H), 3.54-3.79 (m, 3 H), 3.93-4.28 (m, 2.5 H), 4.70 (m, 0.5 H), 5.11-5.20 (m, 2 H), 5.35 (d, J = 13.5 Hz, 0.5 H), 6.73 (t, J = 8.1 Hz, 1 H), 6.85 (d, J = 10.8 Hz, 0.5 H), 6.95 (d, J = 10.8 Hz, 0.5 H), 7.62 (t, J = 7.8 Hz, 0.5 H), 7.70 (t, J = 7.8 Hz, 0.5 H), 9.09 (br, s, 1 H). |
| 11 | The compound was present as two rotamers in a ratio of 1:2. $^1$H NMR (400 MHz, DMSO-d) δ ppm 0.86-1.41 (m, 6 H), 1.21 (d, J = 6.6 Hz, 2 H), 1.27 (d, J = 6.4 Hz, 1 H), 1.75 (br s, 3 H), 2.32 (br s, 1 H), 3.35-3.59 (m, 4.33 H), 3.59-3.91 (m, 4 H), 4.01 (br s, 1.67 H), 4.87-5.04 (m, 1.33 H), 5.07-5.26 (m, 1.67 H), 6.59-6.72 (m, 1 H), 6.72-6.86 (m, 1 H), 7.50-7.61 (m, 1 H), 8.96 (br s, 0.67 H), 9.01 (br s, 0.33 H) |
| 12 | The compound was present as two rotamers in a ratio of 1:1. $^1$H NMR (400 MHz, DMSO-d) δ ppm 0.33-0.41 (m, 0.5 H), 0.46-0.61 (m, 1 H), 0.69 (p, J = 0.73 Hz, 0.5 H), 0.82-1.00 (m, 2 H), 1.08-1.19 (m, 3 H), 1.26 (d, J = 6.7 Hz, 1.5 H), 1.39 (d, J = 6.4 Hz, 1.5 H), 1.83-2.02 (m, 2 H), 2.02-2.24 (2 br s, 1 H), 2.56-2.72 (m, 1 H), 3.07-3.17 (m, 1 H), 3.17-3.32 (m, 1.5 H), 3.35-3.50 (m, 2 H), 3.50-3.66 (m, 1 H), 3.66-3.80 (m, 1 H), 3.84 (td, J1 = 12.9 Hz, J2 = 3.5 Hz, 1 H), 3.88-3.96 (m, 0.5 H), 3.96-4.06 (m. 1 H), 4.81 (br s, 0.5 H), 5.05 (d, J = 13.4, 0.5 H), 5.10 (d, J = 13.3, 0.5 H), 5.19 (br s, 0.5 H), 5.30 (d, J = 13.4 Hz, 0.5 H), 5.37 (d, J = 13.3 Hz, 0.5 H), 6.41-6.51 (m, 1 H), 6.57 (t, J = 8.2 Hz, 1 H), 7.68-7.79 (m, 1 H), 8.38 (br s, 0.5 H), 8.44 (br s, 0.5 H) |

TABLE 3-continued

NMR data

| Co. No. | NMR |
|---|---|
| 13 | The compound was present as two rotamers in a ratio of 2:3.<br>$^1$H NMR (400 MHz, DMSO-d) δ ppm 1.03 (t, J = 7.3 Hz, 1.2 H), 1.07-1.20 (m, 7.8 H), 1.26 (d, J = 6.5 Hz, 1.8 H), 1.33 (d, J = 6.2 Hz, 1.2 H), 1.84 (br s, 2 H), 1.92 (br s, 0.6 H), 2.01 (br s, 0.4 H), 2.43 (br s, 1 H), 3.45-3.72 (m, 3.3 H), 3.72-3.95 (m, 2.7 H), 4.10 (br s, 1.60 H), 4.73-4.83 (br s, 1.4 H), 4.97-5.09 (m, 1.4 H), 5.19-5.33 (m, 1.6 H), 6.75 (br s, 1 H), 6.85 (dd, J1 = 11.3 Hz, J2 = 2.6 Hz, 0.6 H), 6.91 (dd, J1 = 11.3 Hz, J2 = 2.2 Hz, 0.4 H), 7.60-7.67 (m, 1 H), 9.07 (br s, 0.6 H), 9.12 (br s, 0.4 H) |
| 14 | The compound was present as two rotamers in a ratio of 2:3.<br>$^1$H NMR (400 MHz, DMSO-d) δ ppm 0.42 (br s, 1 H), 0.53 (br s, 0.4 H), 0.65 (br s, 0.6 H), 0.72-0.94 (m, 2 H), 0.95-1.09 (m, 6 H), 1.12 (d, J = 6.0, 1.8 H), 1.21 (J = 6.3 Hz, 1.2 H), 1.81 (br s, 3 H), 2.43 (br s, 1 H), 3.07 (br s, 1 H), 3.35-3.78 (m, 3.6 H), 3.78-4.17 (m, 2.4 H), 4.60-4.84 (m, 1.6 H), 4.84-5.24 (m, 2.4 H), 6.65 (t, J = 8.3 Hz, 1 H), 6.76 (d, J = 11.4 Hz, 0.6 H), 6.83 (d, J = 11.0 Hz, 0.4 H), 7.48-7.59 (m, 1 H), 8.97 (2 br s, 1 H) |
| 15 | The compound was present as two rotamers in a ratio of 2:1.<br>$^1$H NMR (300 MHz, DMSO-d) δ ppm 0.95 (t, J = 7.2 Hz, 2 H), 1.03 (t, J = 6.9 Hz, 1 H), 1.14 (t, J = 6.9 Hz, 3 H), 1.28-1.40 (m, 3 H), 1.63 (br s, 2 H), 1.86 (br, 3 H), 2.21 (br, 0.4 H), 2.41 (br, 0.6 H), 3.37-3.81 (m, 7 H), 3.92-4.32 (m, 3 H), 4.99 (m, 0.66 H), 5.01-5.37 (m, 2.33 H), 6.75 (dt, J1 = 8.4 Hz, J2 = 2.1 Hz, 1 H), 6.92 (dd, J1 = 6.9 Hz, J2 = 2.4 Hz, 1 H), 7.52 (t, J = 7.23 Hz, 0.33 H), 7.67 (t, J = 7.8 Hz, 0.66 H), 9.09 (br s, 0.33 H), 9.14 (br s, 0.66 H) |
| 16 | The compound was present as two rotamers in a ratio of 3:2.<br>$^1$H NMR (400 MHz, DMSO-d) δ ppm 0.34-0.44 (m, 0.6 H), 0.44-0.52 (m, 0.4 H), 0.52-0.67 (m, 1 H), 0.67-0.86 (m, 2 H), 1.09-1.20 (m, 3 H), 1.29 (d, J = 6.6, 1.2 H), 1.39 (d, J = 6.7, 1.8 H), 1.54-1.77 (m, 2 H), 1.77-2.04 (m, 3 H), 2.38-2.61 (m, 1 H), 2.96 (q, 0.6 H), 3.08-3.30 (m, 2.4 H), 3.37-3.67 (m, 3 H), 3.80-4.13 (m, 3 H), 3.87 (br, 0.6 H), 5.09-5.37 (m, 2.4 H), 6.48 (d, J = 11.2 Hz, 1 H), 6.54 (t, J = 8.2 Hz, 1 H), 7.70 (t, J = 7.8 Hz, 0.4 H), 7.78 (t, t = 7.8 Hz, 0.6 H), 8.47 (br, 1 H) |
| 17 | The compound was present as two rotamers in a ratio of 1:3.<br>$^1$H NMR (400 MHz, DMSO-d) δ ppm 1.34 (t, J = 7.2 Hz, 3 H), 1.52 (d, J = 6.8 Hz, 2.25 H), 1.61 (d, J = 6.5 Hz, 0.75 H), 2.12 (br, 3 H), 2.43 (br s, 1H), 3.49 (s, 0.75 H), 3.61 (br s, 3.25 H), 3.66-3.74 (m, 0.75 H), 3.75-3.88 (m, 2.25 H), 4.00 (dd, J1 = 13.4 Hz, J2 = 4.25 Hz, 1 H), 4.03-4.22 (m, 1.75 H), 4.37 (br s, 1.25 H), 5.07 (br s, 0.25 H), 5.21 (d, J = 13.6 Hz, 0.75 H), 5.28 (d, J = 13.9, 0.25 H), 5.42-5.53 (m, 1.75 H), 7.34 (d, J = 11.8 Hz, 0.75 H), 7.41 (d, J = 11.8 Hz, 0.25 H), 7.97 (d, J = 8.3 Hz, 0.25 H), 8.01 (d, J = 8.7 Hz, 0.75 H), 9.37 (br s, 1 H) |
| 18 | The compound was present as two rotamers in a ratio of 1:2.<br>$^1$H NMR (400 MHz, CDCl$_3$) δ ppm 1.09-1.19 (m, 3 H), 1.31 (d, J = 6.7 Hz, 2 H), 1.43 (d, J = 6.4 Hz, 1 H), 1.59-1.74 (m, 2 H), 1.89 (2 br s, 2 H), 2.05 (br s, 1 H), 2.19 (br s, 0.67 H), 2.35 (br s, 0.33 H), 3.15 (br s, 1.67 H), 3.18 (br s, 0.33 H), 3.23 (s, 2 H), 3.24-3.31 (m, 1.33 H), 3.34-3.50 (m, 1.67 H), 3.52-3.70 (m, 1 H), 3.85-4.06 (m, 2.33 H), 4.06-4.15 (m, 0.67 H), 4.81 (br s, 0.33 H), 5.07-5.17 (m, 1 H), 5.24 (br s, 0.67 H), 5.28-5.40 (m, 1 H), 6.6 (d, J = 11.0 Hz, 1 H), 7.77 (d, J = 8.1 Hz, 0.67 H), 7.86 (d, J = 8.1 Hz, 0.33 H), 8.50 (br s, 0.67 H), 8.55 (br s, 0.33 H) |
| 19 | $^1$H NMR (600 MHz, CHLOROFORM-d) δ ppm 1.22 (t, J = 7.2 Hz, 3 H), 1.38 (d, J = 6.7 Hz, 3 H), 1.81-1.90 (m, 1 H), 2.07-2.21 (m, 2 H), 2.77-2.87 (m, 1 H), 3.20-3.26 (m, 2 H), 3.34 (ddd, J = 14.4, 12.6, 5.6 Hz, 1 H), 3.50 (s × t, J = 7.2 Hz, 1 H), 3.47 (s, 3 H), 3.67 (s × t, J = 7.2 Hz, 1 H), 3.72 (ddd, J = 11.0, 9.4, 3.5 Hz, 1 H), 3.96 (dd, J = 13.1, 4.0 Hz, 1 H), 4.10 (ddd, J = 9.1, 5.1, 3.4 Hz, 1 H), 5.08 (d, J = 13.4 Hz, 1 H), 5.34 (d, J = 13.4 Hz, 1 H), 5.38-5.43 (m, 1 H), 6.60 (dd, J = 12.0, 6.5 Hz, 1 H), 7.75 (dd, J = 10.3, 9.4 Hz, 1 H), 8.51 (br. s, 1 H), minor rotamer observed (12%) |
| 20 | The compound was present as two rotamers in a ratio of 50:50.<br>$^1$H NMR (300 MHz, DMSO-d) δ ppm 1.13-1.18 (m, 3 H), 1.34 (d, J = 6.5 Hz, 1.5 H), 1.39 (d, J = 6.5 Hz, 1.5 H), 1.59-1.77 (m, 2H), 1.91 (br s, 3 H), 2.23 (br s, 1 H), 2.47 (br s, 1 H), 3.22 (s, 1.5 H), 3.28 (s, 1.5 H), 3.38-3.88 (m, 4 H), 3.95-4.12 (m, 1.7 H), 4.12-4.30 (m, 1.3 H), 4.83 (br s, 0.5 H), 5.11-5.32 (m, 2.5 H), 7.14-7.28 (m, 1 H), 7.60-7.22 (m, 1 H), 9.15 (s, 0.5 H), 9.18 (s, 0.5 H) |
| 21 | The compound was present as two rotamers in a ratio of 3:2.<br>$^1$H NMR (400 MHz, DMSO-d) δ ppm 1.05-1.12 (m, 5 H), 1.27 (d, J = 6.7 Hz, 1.8 H), 1.37 (d, J = 6.7 Hz, 1.2 H), 1.48-2.08 (m, 6 H), 3.17 (s, 1.2 H), 3.21 (s, 1.8 H), 3.33-3.42 (m, 2 H), 3.42-3.51 (m, 2 H), 3.52-3.66 (m, 1 H), 3.77 (dd, J1 = 13.1 Hz, J2 = 3.3 Hz, 0.6 H), 3.95 (dd, J1 = 13.5 Hz, J2 = 3.6 Hz, 0.4 H), 4.75-4.85 (m, 0.4 H), 5.05 (d, J = 14.6 Hz, 0.6 H), 5.17 (m, 1H), 5.67 (d, J = 13.5 Hz, 0.4 H), 5.76 (d, J = 13.9 Hz, 0.6 H), 7.20-7.27 (m, 2 H), 7.63 (dd, J1 = 8.17 Hz, J2 = 5.7 Hz, 0.6H), 7.69 (br, s, 0.4 H), 8.64 (t, J = 5.3 Hz, 0.6 H), 8.70 (t, J = 5.3 Hz, 0.4 H), 9.12 (2 br s, 1 H) |
| 22 | The compound was present as two rotamers in a ratio of 3:2.<br>$^1$H NMR (300 MHz, DMSO-d) δ ppm 1.11 (t, J = 7.5 Hz, 3 H), 1.31 (d, J = 6.7 Hz, 1.2 H), 1.36 (d, J = 6.5 Hz, 1.8 H), 1.66-1.85 (m, 2 H), 1.89-2.11 (m, 2 H), 3.17 (s, 1.8 H), 3.22 (s, 1.2 H), 3.42-3.65 (m, 5 H), 3.80 (dd, J1 = 13.5 Hz, J2 = 3.2 Hz, 0.4 H), 3.96 (dd, J1 = 13.5 Hz, J2 = 3.2 Hz, 0.6 H), 4.78 (br, s, 1 H), 5.20 (d, J = 13.4 Hz, 0.6 H), 5.20-5.30 (m, 0.4 H), 5.77 (d, J = 5.8 Hz, 0.6 H), 5.82 (d, J = 6.5 Hz, 0.4 H), 7.26-7.39 (m, 2 H), 7.76 (dt, J1 = 5.8 Hz, J2 = 2.6 Hz, 0.6 H), 7.77-7.88 (m, 0.4 H), 8.55 (t, J = 4.9 Hz, 0.6 H), 8.66 (t, J = 5.3 Hz, 0.4 H), 9.18 (br, s, 1 H) |

TABLE 3-continued

NMR data

| Co. No. | NMR |
|---|---|
| 23 | The compound was present as two rotamers in a ratio of 1:1.<br>$^1$H NMR (300 MHz, DMSO-d) δ ppm 1.11 (t, J = 7.1 Hz, 3 H), 1.29-1.36 (dd, J = 6.6 Hz, 6.3 Hz, 3 H), 1.99-2.05 (m, 2 H), 3.01-3.22 (m, 1 H), 3.27-3.29 (d, J = 7.5 Hz, 2H), 3.50-3.55 (m, 4 H), 3.71-3.79 (m, 2 H), 4.68-5.41 (br s, 1 H), 5.36-5.44 (br s, 1 H), 5.66-5.77 (m, 1 H), 7.25-7.35 (m, 1 H), 7.94 (m, 1 H), 8.61-8.68 (2m, 1 H), 9.14 (br, s, 1H) |
| 24 | $^1$H NMR (400 MHz, DMSO-d) δ ppm 1.10 (t, J = 6.8 Hz, 3 H), 1.20 (d, J = 6.0 Hz, 3 H), 1.68-1.75 (m, 2 H), 1.89-1.91 (m, 2 H), 2.99-3.09 (m, 1 H), 3.17 (d, J = 4.8 Hz, 2 H), 3.41-3.47 (m, 1 H), 3.54-3.62 (m, 1 H), 3.70-3.95 (m, 2 H), 4.12-4.13 (m, 1 H), 4.92 (m, 1 H), 5.13 (d, J = 12.8 Hz, 1 H), 5.23 (d, J = 13.2 Hz, 1 H), 6.74 (t, J = 7.4 Hz, 1 H), 6.91-6.94 (dd, J1 = 2.0 Hz, J2 = 11.6 Hz, 1 H), 7.72 (t, J = 8 Hz, 1 H), 8.51 (br s, 1 H), 9.05 (s, 1 H) |
| 25 | $^1$H NMR (400 MHz, DMSO-d) δ ppm 1.10 (t, J = 6.8 Hz, 3 H), 1.24 (d, J = 6.2 Hz, 3 H), 1.61-1.77 (m, 6 H), 3.23-3.49 (m, 4 H), 3.54-3.66 (m, 1 H), 3.88-3.91 (dd, J1 = 3.6 Hz, J2 = 13.2 Hz, 1 H), 4.04 (m, 2 H), 5.10 (br s, 1 H), 5.28 (br s, 2 H), 6.95 (d, J = 8.0 Hz, 1 H), 7.06 (s, 1 H), 7.59 (d, J = 8.0 Hz, 1 H), 8.15 (m, 1 H), 9.10 (br s, 1 H) |
| 26 | $^1$H NMR (400 MHz, DMSO-d) δ ppm 1.11 (t, J = 7.2 Hz, 3 H), 1.24 (d, J = 6.4 Hz, 3 H), 1.61-1.76 (m, 6 H), 3.15-3.28 (m, 3 H), 3.45 (d, J = 12.4 Hz, 2 H), 3.58-3.67 (m, 1 H), 3.88-3.92 (dd, J1 = 3.2 Hz, J2 = 13.6 Hz, 1 H), 4.03 (m, 2 H), 5.08 (m, 1 H), 5.26 (br s, 2 H), 7.15 (d, J = 11.6 Hz, 1 H), 7.70 (d, J = 8.8 Hz, 1 H), 8.37 (m, 1 H), 9.15 (s, 1 H) |
| 27 | $^1$H NMR (400 MHz, DMSO-d) δ ppm 1.11 (t, J = 7.2 Hz, 3 H), 1.62 (m, 2 H), 1.75 (m, 4 H), 3.32 (m, 2 H), 3.47 (q, J = 7.2 Hz, 1 H), 3.68 (t, J = 5.6 Hz, 2 H), 4.01 (m, 2 H), 4.36 (m, 2 H), 5.28 (m, 2 H), 6.68-6.74 (dt, J1 = 2.4 Hz, J2 = 8.0 Hz, 1 H), 6.86-6.89 (dd, J1 = 2.8 Hz, J2 = 7.6 Hz, 1 H), 7.63 (t, J = 8.0 Hz, 1 H), 8.35 (m, 1 H), 9.07 (s, 1 H) |
| 28 | $^1$H NMR (400 MHz, CDCl$_3$-d) δ ppm 1.30 (d, J = 6.8 Hz, 3 H), 1.53-1.82 (m, 6 H), 3.05 (s, 3 H), 3.13 (d, J = 12.5 Hz, 1 H), 3.34 (m, 1 H), 3.48 (m, 1 H), 3.92-4.00 (m, 3 H), 5.30 (br s, 1 H), 5.70 (m, 1 H), 6.52 (m, 2 H), 7.19 (m, 1 H), 7.69 (t, J = 7.6 Hz, 1 H), 8.66 (br s, 1 H) |
| 29 | $^1$H NMR (300 MHz, CDCl$_3$-d) δ ppm 1.13 (t, J = 6.3 Hz, 6 H), 1.24 (d, J = 6.6 Hz, 3 H), 1.56-1.80 (m, 6 H), 3.16-3.21 (dd, J1 = 1.2 Hz, J2 = 12.9 Hz, 1 H), 3.30 (m, 1 H), 3.46 (m, 1 H), 3.62-3.68 (dd, J1 = 3.9 Hz, J2 = 13.2 Hz, 1 H), 3.92-4.01 (m, 2 H), 4.80-4.92 (p, J = 6.9 Hz, 1 H), 5.32 (br s 2 H), 5.71-5.73 (br s, 1 H), 6.50-6.56 (m, 2 H), 7.71 (t, J = 7.5 Hz, 1 H), 8.79 (br s, 1 H) |
| 30 | $^1$H NMR (400 MHz, DMSO-d) δ ppm 1.09 (t, J = 7.2 Hz, 3 H), 1.17 (d, J = 6.4 Hz, 3 H), 1.70 (m, 1 H), 1.93 (m, 1 H), 2.06 (m, 1 H), 2.33 (m, 1 H), 3.11 (s, 3 H), 3.14-3.24 (m, 2 H), 3.42 (d, J = 13.6 Hz, 1 H), 3.53-3.60 (m, 1 H), 3.64-3.69 (m, 1 H), 3.80-3.88 (m, 2 H), 4.12-4.14 (m, 1 H), 4.69-4.76 (m, 1 H), 5.11 (d, J = 13.2 Hz, 1 H), 5.22 (d, J = 13.2 Hz, 1 H), 6.71-6.75 (dt, J1 = 2.0 Hz, J2 = 8.0 Hz, 1 H), 6.92-6.95 (dd, J1 = 2.0 Hz, J2 = 11.6 Hz, 1 H), 7.68 (t, J = 7.8 Hz, 1 H), 9.02 (s, 1 H) |
| 31 | The compound was present as two rotamers in a ratio of 85:15.<br>$^1$H NMR (400 MHz, DMSO-d) δ ppm 1.11 (t, J = 7.6 Hz, 3 H), 1.20 (d, J = 6.8 Hz, 2.6 H), 1.36 (d, J = 6.4 Hz, 0.4 H), 1.40-1.57 (m, 2 H), 1.57-1.93 (m, 4 H), 3.04 (s, 3 H), 3.12-3.20 (m, 1 H), 3.29-3.50 (m, 2 H), 3.54-3.68 (m, 1 H), 3.89 (dd, J1 = 13.2 Hz, J2 = 3.6 Hz, 1 H), 4.02-4.11 (m, 1 H), 4.12-4.13 (m, 1 H), 4.23-4.37 (m, 0.85 H), 4.44 (br, s, 0.15 H), 4.56-4.67 (m, 0.85 H), 4.83 (m, 0.15 H), 5.13 (d, J = 13.6 Hz, 1 H), 5.28 (d, J = 13.6 Hz, 1 H), 6.68 (br, s, 0.15 H), 6.73 (dt, J1 = 8.4 Hz, J2 = 2.4 Hz, 0.85 H), 6.85 (d, J = 11.2 Hz, 0.15 H), 6.91 (dd, J1 = 11.2 Hz, J2 = 2.4 Hz, 0.85 H), 7.54 (t, J = 7.2 Hz, 0.85 H), 7.61 (br, s, 0.15 H), 9.08 (br s, 1 H) |
| 32 | $^1$H NMR (300 MHz, DMSO-d) δ ppm 1.16 (t, J = 7.2 Hz, 3 H), 1.26 (d, J = 6.4 Hz, 3 H), 1.42-1.62 (m, 3 H), 1.80 (m, 5 H), 3.09 (s, 3H), 3.19-3.21 (m, 1 H), 3.58-3.66 (m, 1 H), 3.75-3.95 (m, 1 H), 4.15-4.37 (m, 1 H), 4.63 (br s, 2 H), 5.15-5.30 (q, J = 7.3 Hz, 3 H), 7.20 (d, J = 4.4 Hz, 1 H), 7.77 (d, J = 14.7 Hz, 1 H), 9.17 (br s, 1 H). |
| 33 | $^1$H NMR (400 MHz, CDCl$_3$) δ ppm 1.10-1.24 (m, 11 H), 1.60-1.72 (m, 3 H), 1.87-1.98 (m, 2 H), 3.02-3.43 (m, 6 H), 3.58-3.66 (m, 1 H), 3.79-3.87 (m, 1 H), 3.91-4.00 (m, 1 H), 4.09-4.12 (m, 1 H), 4.95 (m, 1 H), 5.10-5.14 (d, J = 13.6 Hz, 1 H), 5.42-5.46 (d, J = 14.0 Hz, 1 H), 6.58-6.61 (d, J = 10.8 Hz, 1 H), 7.64-7.66 (d, J = 5.8 Hz, 1 H), 8.57 (br s, 1 H). |
| 34 | $^1$H NMR (400 MHz, CDCl$_3$) δ ppm 1.14 (t, J = 7.2 Hz, 3 H), 1.20 (d, J = 6.4 Hz, 3 H), 1.46 (m, 2 H), 1.71 (m, 2 H), 1.90 (m, 2 H), 2.87 (m, 1 H), 3.04 (s, 3 H), 3.09 (d, J = 12.0 Hz, 1 H), 3.37-3.48 (m, 2 H), 3.59-3.71 (m, 1 H), 3.89-3.95 (m, 2 H), 4.04-4.09 (m, 2 H), 4.89-4.91 (m, 1 H), 5.14 (d, J = 14.0 Hz, 1 H), 5.40 (d, J = 13.6 Hz, 1 H), 6.57-6.62 (q, J = 6.4 Hz, 1 H), 7.47 (t, J = 6.4 Hz, 1 H), 8.57 (br s, 1 H) |
| 35 | $^1$H NMR (300 MHz, DMSO-d) δ ppm 1.13-1.19 (m, 9 H), 1.77 (m, 5 H), 3.07 (s, 3 H), 3.14-3.26 (m, 2 H), 3.52 (m, 1 H), 3.66-3.70 (dd, J = 13.8 Hz, J = 3.9 Hz, 1 H), 4.11 (m, 1 H), 4.19 (m, 1 H), 4.65 (br, s, 1 H), 4.80 (m, 1 H), 5.14 (d, J = 13.5 Hz, 1 H), 5.29 (d, J = 13.5 Hz, 1 H), 4.04-4.09 (m, 1 H), 6.77 (m, 1 H), 6.92-6.97 (m, 1 H), 7.57 (t, J = 7.5 Hz, 1 H), 9.14 (s, 1 H) |
| 36 | $^1$H NMR (400 MHz, CDCl$_3$-d) δ ppm 0.46 (m, 1 H), 0.75 (m, 1 H), 0.86 (m, 1 H), 1.02 (m, 1 H), 1.21 (d, J = 6.8 Hz, 3 H), 1.64-1.80 (m, 6 H), 2.68-2.70 (m, 1 H), 3.19-3.23 (dd, J1 = 1.6 Hz, J2 = 13.2 Hz, 1 H), 3.33 (m, 1 H), 3.48 (m, 1 H), 3.86-3.90 (dd, J1 = 4.0 Hz, J2 = 13.2 Hz, 1 H), 3.97 (m, 2 H), 5.32 (br s, 2 H), 5.67 (m, 1 H), 6.53 (m, 2 H), 7.17 (m, 1 H), 7.70 (t, J = 7.6 Hz, 1 H), 8.75 (s, 1 H) |

TABLE 3-continued

NMR data

| Co. No. | NMR |
|---|---|
| 37 | The compound was present as two rotamers in a ratio of 1:1.<br>$^1$H NMR (300 MHz, DMSO-d) δ ppm 0.45 (m, 1 H), 0.66-0.69 (m, 2 H), 0.79-0.83 (m, 1 H), 1.02-1.22 (d, J = 9.6 Hz, 3 H), 1.40 (m, 3 H), 1.64 (m, 4 H), 2.68-2.73 (m, 2 H),, 2.94 (s, 3 H), 3.04-3.09 (m, 1 H), 3.76-3.77 (dd, J = 6.6 Hz, 2.2 Hz, 1 H), 3.80-4.09 (m, 2 H), 4.48 (br, s, 1 H), 5.01-5.21 (dd, J = 28.6 Hz, 13.8 Hz, 2 H), 6.64 (t, J = 2.1 Hz, 1 H), 6.66-6.81 (d, J = 12.8 Hz, 1 H), 7.42-7.47 (t, J = 15.6 Hz, 1 H), 9.03 (br, s, 1 H) |
| 38 | $^1$H NMR (400 MHz, CDCl$_3$) δ ppm 1.22-1.28 (m, 5 H), 1.84-1.95 (m, 5 H), 3.15 (s, 3 H), 3.38-3.41 (t, J = 15.6 Hz, 2 H), 3.55-3.66 (m, 6 H), 3.55-3.66 (m, 6 H), 4.09-4.12 (t, J = 5.6 Hz, 2 H), 4.26-4.29 (t, J = 5.8 Hz, 2 H), 5.43 (s, 2 H), 6.50-6.64 (m, 3 H), 7.60-7.64 (t, J = 7.6 Hz, 1 H), 8.51 (br s, 1 H). |
| 39 | $^1$H NMR (400 MHz, DMSO-d) δ ppm 1.17 (t, J = 7.2 Hz, 3 H), 1.21-1.34 (m, 5 H), 1.87-1.95 (m, 1 H), 1.95-2.10 (m, 1 H), 2.94-3.12 (m, 0.7 H), 3.16-3.28 (m, 1.3 H). 3.53 (d, J = 12.2 Hz, 1 H), 3.61-3.72 (m, 1.1 H), 3.97 (dd, J1 = 13.2 Hz, J2 = 3.7 Hz, 0.88 H), 5.16 (br s, 1 H), 5.37 (d, J = 12.6 Hz, 0.7 H), 5.41 (d, J = 12.6 Hz, 0.7 H), 5.78 (d, J = 6.5 Hz, 0.1 H), 5.81 (d, J = 6.5 Hz, 0.1 H), 5.90-5.96 (m, 0.1 H), 6.06 (t, J = 4.6 Hz, 0.68 H), 6.10-6.15 (m, 0.1 H), 7.19 (d, J = 8.9 Hz, 0.3 H), 7.25 (dd, J1 = 9.3 Hz, J2 = 2.3 Hz, 0.8 H), 7.30 (dt, J1 = 8.4 Hz, J2 = 2.5 Hz, 1 H), 7.55-7.67 (m, 1 H), 7.95 (t, J = 8, 0.24 H), 8.41 (t, J = 5.9, 0.72 H), 8.92 (br s, 0.82 H) |
| 40 | $^1$H NMR (400 MHz, DMSO-d) δ ppm 1.16 (t, J = 7.2 Hz, 3 H), 1.36 (d, J = 6.4 Hz, 3 H), 1.56 (m, 2 H), 1.67-1.83 (m, 4 H), 3.15-3.17 (m, 1 H), 3.26-3.29 (m, 1 H), 3.35-3.37 (m, 2 H), 3.53 (d, J = 12.8 Hz, 2 H), 3.62-3.71 (m, 1 H), 3.94-3.98 (dd, J1 = 3.2 Hz, J2 = 13.2 Hz, 1 H), 5.16 (m, 1 H), 5.41 (d, J = 13.6 Hz, 1 H), 5.50 (d, J = 13.6 Hz, 1 H), 6.01 (m, 1 H), 7.25-7.32 (m, 2 H), 7.94-7.97 (dd, J1 = 6.4 Hz, J2 = 8.4 Hz, 1 H), 8.59 (t, J = 5.6 Hz, 1 H), 8.98 (br s, 1 H) |
| 41 | $^1$H NMR (400 MHz, DMSO-d) δ ppm 1.12 (t, J = 7.2 Hz, 3 H), 1.21 (d, J = 6.4 Hz, 3 H), 1.33 (m, 2 H), 1.48 (m, 4 H), 1.55-1.56 (m, 2 H), 3.08 (m, 2 H), 3.26-3.40 (m, 3 H), 3.49 (d, J = 13.2 Hz, 1 H), 3.60-3.65 (m, 1 H), 3.92-3.94 (dd, J1 = 3.8 Hz, J2 = 12.6 Hz, 1 H), 5.12 (m, 1 H), 5.26 (q, J = 14.4 Hz, 2 H), 5.93 (m, 1 H), 7.20-7.25 (m, 2 H), 7.52-7.56 (dd, J1 = 5.6 Hz, J2 = 8.4 Hz, 1 H), 8.65 (t, J = 6 Hz, 1 H), 8.96 (s, 1 H) |
| 42 | $^1$H NMR (400 MHz, DMSO-d) δ ppm 1.04 (d, J = 6.3 Hz, 3 H), 1.14 (t, J = 6.7 Hz, 3 H), 1.26-1.45 (m, 6 H), 1.73-1.75 (m, 2 H), 2.77-2.84 (m, 1 H), 3.04 (s, 3 H), 3.13-3.40 (m, 4 H), 3.50 (d, J = 11.6 Hz, 1 H), 3.57-3.66 (m, 1 H), 3.97 (d, J = 12.0 Hz, 1 H), 4.20-4.25 (dd, J1 = 4.4 Hz, J2 = 15.6 Hz, 1 H), 5.13 (m, 1 H), 5.73-5.77 (dd, J1 = 2.8 Hz, J2 = 16.2 Hz, 1 H), 5.99-6.09 (m, 1 H), 6.77-6.80 (m, 1 H), 7.17 (d, J = 8.8 Hz, 2 H), 8.96 (br s, 1 H) |
| 43 | $^1$H NMR (400 MHz, CDCl$_3$-d) δ ppm 1.21-1.31 (m, 6 H), 1.40-1.59 (m, 8 H), 2.60 (s, 3 H), 3.74 (d, J = 12.8 Hz, 1 H), 3.32-3.36 (m, 2 H), 3.51-3.56 (m, 1 H), 3.60-3.70 (m, 2 H), 3.99-4.04 (dd, J1 = 4.0 Hz, J2 = 13.2 Hz, 1 H), 4.88-4.89 (m, 1 H), 4.99 (d, J = 14.8 Hz, 1 H), 5.91 (d, J = 14.4 Hz, 1 H), 6.54 (m, 1 H), 7.02-7.05 (dt, J1 = 2.8 Hz, J2 = 8.4 Hz, 1 H), 7.17-7.20 (dd, J1 = 2.8 Hz, J2 = 8.8 Hz, 1 H), 7.57-7.60 (dd, J1 = 5.6 Hz, J2 = 8.4 Hz, 1 H), 8.67 (s, 1 H) |
| 44 | $^1$H NMR (600 MHz, CHLOROFORM-d) δ ppm 1.23 (t, J = 7.2 Hz, 1.2 H), 1.22 (t, J = 7.2 Hz, 1.8 H), 1.35 (d, J = 6.6 Hz, 1.8 H), 1.36 (d, J = 6.6 Hz, 1.2 H), 2.13-2.21 (m, 1 H), 2.28 (dt, J = 16.0, 5.0 Hz, 0.4 H), 2.31-2.38 (m, 0.4 H), 2.38-2.46 (m, 1.2 H), 2.95-3.03 (m, 1 H), 3.07-3.15 (m, 1 H), 3.20 (ddd, J = 14.2, 8.3, 6.1 Hz, 0.4 H), 3.25 (d, J = 12.9 Hz, 1 H), 3.29-3.41 (m, 2.4 H), 3.43-3.56 (m, 3.2 H), 3.66-3.74 (m, 1 H), 3.82 (ddd, J = 13.6, 7.9, 5.9 Hz, 0.6 H), 3.97 (dd, J = 12.9, 4.0 Hz, 1 H), 4.06 (ddd, J = 9.6, 6.1, 3.6 Hz, 0.6 H), 4.10 (ddd, J = 9.3, 4.6, 4.4 Hz, 0.4 H), 4.28 (td, J = 8.8, 3.0 Hz, 0.6 H), 4.32-4.37 (m, 0.8 H), 4.39 (td, J = 9.9, 3.6 Hz, 0.4 H), 4.47-4.55 (m, 0.6 H), 4.91-4.97 (m, 0.6 H), 5.09 (d, J = 13.5 Hz, 0.6 H), 5.10 (d, J = 13.6 Hz, 0.4 H), 5.14-5.20 (m, 0.4 H), 5.49 (d, J = 13.5 Hz, 0.6 H), 5.52 (d, J = 13.6 Hz, 0.4 H), 6.58 (td, J = 8.3, 2.6 Hz, 1 H), 6.63 (dd, J = 11.1, 2.5 Hz, 0.6 H), 6.60 (dd, J = 11.0, 2.3 Hz, 0.4 H), 7.86 (dd, J = 8.6, 7.0 Hz, 0.6 H), 7.83 (dd, J = 8.5, 7.0 Hz, 0.4 H), 8.50 (br. s., 0.4 H), 8.52 (br. s, 0.6 H) |
| 45 | $^1$H NMR (600 MHz, CHLOROFORM-d) δ ppm 1.23 (t, J = 7.2 Hz, 3 H), 1.34 (d, J = 6.5 Hz, 2 H), 1.40 (d, J = 6.5 Hz, 1 H), 1.77-1.87 (m, 1 H), 1.90-2.15 (m, 3 H), 2.26-2.33 (m, 1 H), 2.77 (ddd, J = 13.7, 8.5, 5.1 Hz, 1 H), 2.96-3.03 (m, 1.3 H), 3.03-3.24 (m, 2.7 H), 3.24-3.29 (m, 1.35 H), 3.38-3.46 (m, 1.65 H), 3.50 (s × t, J = 7.3 Hz, 1 H), 3.66-3.75 (m, 1 H), 3.91-3.98 (m, 1.35 H), 4.01 (dd, J = 12.9, 4.1 Hz, 0.65 H), 4.02-4.07 (m, 0.35 H), 4.09-4.18 (m, 1.65 H), 4.24 (br. d, J = 13.4 Hz, 0.65 H), 4.44 (br. d, J = 13.1 Hz, 0.35 H), 4.93-5.00 (m, 0.65 H), 5.11 (br. d, J = 13.4 Hz, 0.65 H), 5.14 (br. d, J = 13.3 Hz, 0.35 H), 5.20-5.26 (m, 0.35 H), 5.45 (br. d, J = 13.5 Hz, 0.35 H), 5.50 (br. d, J = 13.5 Hz, 0.65 H), 6.53-6.63 (m, 2 H), 7.53 (dd, J = 7.9, 7.4 Hz, 0.65 H), 7.60 (t, J = 7.7 Hz, 0.35 H), 8.42 (br. s, 0.35 H), 8.52 (br. s., 0.65 H) |
| 46 | $^1$H NMR (300 MHz, CDCl3) δ ppm 0.82 (m, 1H), 1.13-1.31 (m, 12 H), 1.68 (m, 2 H), 2.57 (s, 1 H), 2.78-2.85 (m, 1 H), 3.17-3.21 (d, J = 12.6 Hz, 1 H), 3.42-3.44 (m, 1 H), 3.46-3.51 (m, 1 H), 3.54-3.62 (m, 1 H), 3.85-4.09 (m, 3 H), 4.84 (br s, 1 H), 5.17 (s, 2 H), 6.50-6.56 (m, 2 H), 7.74-7.76 (t, J = 7.2 Hz, 1 H), 8.53 (br s, 1 H). |
| 47 | $^1$H NMR (600 MHz, CHLOROFORM-d) δ ppm 1.22 (t, J = 7.2 Hz, 3 H), 1.41 (d, J = 6.6 Hz, 3 H), 1.74-1.83 (m, 2 H), 1.83-1.94 (m, 2 H), 3.27 (dd, J = 13.1, 1.5 Hz, 1 H), 3.31 (dt, J = 14.1, 5.1 Hz, 1 H), 3.52 (s × t, J = 7.1 Hz, 1 H), 3.50-3.58 (m, 2 H), 3.66 (s × t, J = 7.1 Hz, 1 H), 3.93-3.97 (m, 2 H), 3.98 (dt, J = 11.2, 7.3 Hz, 1 H), 4.01-4.07 (m, 2 H), 4.19 (ddd, J = 11.5, 8.1, 3.6 Hz, 1 H), 5.10-5.15 (m, 1 H), 5.13 (d, J = 13.6 Hz, 1 H), 5.26 (d, J = 13.6 Hz, 1 H), 6.51 (dd, J = 10.9, 2.4 Hz, 1 H), 6.63 (td, J = 8.3, 2.4 Hz, 1 H), 7.70 (dd, J = 8.5, 6.9 Hz, 1 H), 8.48 (br. s, 1 H) |

TABLE 3-continued

NMR data

| Co. No. | NMR |
|---|---|
| 48 | $^1$H NMR (600 MHz, CHLOROFORM-d) δ ppm 1.23 (t, J = 7.2 Hz, 1.8 H), 1.25 (t, J = 7.2 Hz, 1.2 H), 1.42 (d, J = 6.5 Hz, 1.8 H), 1.53 (d, J = 6.5 Hz, 1.2 H), 1.56-1.64 (m, 0.6 H), 1.64-1.72 (m, 0.4 H), 1.89-1.99 (m, 1 H), 2.01-2.16 (m, 1 H), 2.17-2.28 (m, 1 H), 3.09 (td, J = 13.7, 4.0 Hz, 0.6 H), 3.22-3.25 (m, 1.8 H), 3.28 (s, 1.8 H), 3.32 (d, J = 13.2 Hz, 0.4 H), 3.36 (td, J = 13.4, 3.7 Hz, 0.4 H), 3.48-3.57 (m, 3.2 H), 3.57-3.63 (m, 0.8 H), 3.66 (s × t, J = 6.9 Hz, 0.6 H), 3.72 (s × t, J = 7.2 Hz, 0.4 H), 3.97-4.01 (m, 1 H), 4.43 (d, J = 11.4 Hz, 0.6 H), 4.47 (d, J = 11.2 Hz, 0.4 H), 4.64 (d, J = 11.3 Hz, 0.4 H), 4.80 (d, J = 11.4 Hz, 0.6 H), 4.82-4.88 (m, 0.4 H), 5.28-5.33 (m, 0.6 H), 5.34 (d, J = 14.1 Hz, 0.6 H), 5.39 (d, J = 14.1 Hz, 0.4 H), 5.53 (d, J = 14.1 Hz, 0.4 H), 5.53 (d, J = 14.1 Hz, 0.6 H), 6.94-7.02 (m, 2 H), 7.58 (dd, J = 8.6, 5.6 Hz, 0.4 H), 7.68 (dd, J = 8.4, 5.7 Hz, 0.6 H), 8.57 (br. s., 0.6 H), 8.65 (br. s, 0.4 H) |
| 49 | $^1$H NMR (600 MHz, CHLOROFORM-d) δ ppm 1.20-1.25 (m, 3 H), 1.38 (d, J = 6.7 Hz, 2.1 H), 1.51 (d, J = 6.5 Hz, 0.9 H), 2.77-2.84 (m, 0.7 H), 2.84-2.91 (m, 0.3 H), 2.93-3.01 (m, 0.3 H), 3.01-3.08 (m, 0.7 H), 3.17-3.24 (m, 1.4 H), 3.24 (s, 0.9 H), 3.30 (dd, J = 12.9, 1.6 Hz, 0.3 H), 3.33 (s, 2.1 H), 3.34-3.39 (m, 0.7 H), 3.45-3.56 (m, 1 H), 3.60-3.75 (m, 1.6 H), 3.95 (dd, J = 12.9, 3.8 Hz, 0.3 H), 3.98 (dd, J = 12.9, 4.0 Hz, 0.7 H), 4.44 (dd, J = 12.9, 6.1 Hz, 0.7 H), 4.48 (dd, J = 11.4, 6.6 Hz, 0.3 H), 4.60 (dd, J = 11.3, 6.3 Hz, 0.3 H), 4.81 (dd, J = 12.5, 5.7 Hz, 0.7 H), 4.82-4.85 (m, 0.3 H), 5.27 (d, J = 13.8 Hz, 0.3 H), 5.29-5.33 (m, 0.7 H), 5.34 (d, J = 13.5 Hz, 0.7 H), 5.38 (d, J = 13.2 Hz, 0.7 H), 5.44 (d, J = 13.5 Hz, 0.3 H), 5.72 (dddd, J = 11.0, 9.4, 6.1, 1.8 Hz, 0.7 H), 5.85-5.91 (m, 0.3 H), 5.92-6.00 (m, 1 H), 6.57 (dd, J = 10.9, 2.4 Hz, 0.7 H), 6.61 (dd, J = 11.0, 2.3 Hz, 0.3 H), 6.63 (td, J = 8.3, 2.4 Hz, 1 H), 7.66 (dd, J = 8.5, 6.9 Hz, 0.7 H), 7.81 (dd, J = 8.2, 7.1 Hz, 0.3 H), 8.53 (br. s, 0.7 H), 8.57 (br. s., 0.3 H) |
| 50 | $^1$H NMR (400 MHz, CHLOROFORM-d) δ ppm 1.23 (t, J = 7.2 Hz, 3 H), 1.37 (d, J = 6.8 Hz, 3 H), 1.85-1.96 (m, 1 H), 2.00-2.11 (m, 1 H), 2.29-2.47 (m, 2 H), 3.05-3.15 (m, 1 H), 3.10 (s, 3 H), 3.16-3.32 (m, 2 H), 3.45-3.57 (m, 1 H), 3.61-3.75 (m, 1 H), 3.99 (dd, J = 12.8, 4.1 Hz, 1 H), 4.45 (d, J = 8.1 Hz, 2 H), 5.20 (d, J = 13.6 Hz, 1 H), 5.31 (d, J = 13.6 Hz, 1 H), 5.28-5.36 (m, 1 H), 5.75-5.86 (m, 1 H), 6.00 (ddd, J = 10.9, 7.6, 7.4 Hz, 1 H), 6.61-6.70 (m, 2 H), 7.61 (t, J = 7.7 Hz, 1 H), 8.52 (br. s, 1 H), minor rotamer observed. |
| 51 | $^1$H NMR (400 MHz, CHLOROFORM-d) δ ppm 1.22 (t, J = 7.0 Hz, 3 H), 1.38 (d, J = 6.6 Hz, 3 H), 1.88-2.27 (m, 3 H), 2.38-2.53 (m, 1 H), 3.07 (ddd, J = 13.8, 8.7, 5.2 Hz, 1 H), 3.21-3.34 (m, 1 H), 3.27 (s, 3 H), 3.40 (ddd, J = 13.7, 9.2, 6.9 Hz, 1 H), 3.47-3.58 (m, 1 H), 3.59-3.77 (m, 1 H), 4.00 (dd, J = 13.1, 4.0 Hz, 1 H), 4.39 (d, J = 6.9 Hz, 2 H), 5.02 (d, J = 13.7 Hz, 1 H), 5.27-5.35 (m, 1 H), 5.39 (d, J = 13.7 Hz, 1 H), 5.61 (dt, J = 15.3, 6.8 Hz, 1 H), 5.76 (dt, J = 15.6, 7.3 Hz, 1 H), 6.56 (dd, J = 10.8, 2.5 Hz, 1 H), 6.65 (td, J = 8.2, 2.4 Hz, 1 H), 7.67 (dd, J = 8.4, 6.8 Hz, 1 H), 8.50 (br. s, 1 H), minor rotamer observed. |

B. Biological Activity of Compounds of Formula I

Example 166

Determination of Inhibitory Activity on HIV Replication Wild Type, Q148R mutant, N155H Mutant, and G140S-Q148H Mutant MT4-LTR-enhanced green fluorescent protein (EGFP) cells were obtained by transfecting MT4 cells with a selectable construct encompassing the coding sequences for the HIV LTR as a promoter for the expression of EGFP and subsequent selection of permanently transfected cells. MT4-cytomegalovirus (CMV)-EGFP cells were obtained by selection for permanently transformed MT4 cells with a CMV-EGFP reporter gene. Cell lines were maintained in RPMI 1640 medium supplemented with 10% heat-inactivated fetal calf serum, 2 mM L-glutamine, 0.1% NaHCO$_3$, and antibiotics (0.02% gentamicin and 0.8% G418) and incubated in a humidified incubator with a 5% CO$_2$ atmosphere at 37° C.

N155H and Q148R mutant Integrase coding sequences were constructed in the pUC19-5'HXB2D vector (XbaI-SalI fragment of pHXB2D), containing the HIV-1 clone HXB2D IN coding sequence, by using a QuikChange site-directed mutagenesis kit (Stratagene, La Jolla, Calif.) and HPLC-purified primers (Genset Oligos, La Jolla, Calif.). Altered plasmid sequences were confirmed by dideoxyribose sequencing. For generation of site-directed mutant (SDM) virus stocks, MT4 cells were subcultured at a density of 250,000 cells/ml on the day before transfection. Cells were pelleted and resuspended in phosphate-buffered saline at a concentration of $3.1 \times 10^6$ cells/ml. A 0.8-ml portion ($2.5 \times 10^6$ cells/ml) was used for each transfection. Transfections were performed with a Bio-Rad Gene Pulser (Bio-Rad, Hercules, Calif.) with 0.4-cm electrode cuvettes (Bio-Rad). Cells were electroporated with 10 μg of SalI-linearized pUC19-3'HXB2D (SalI-XbaI fragment of pHXB2D) and 5 μg of SalI-digested SDM at 250 μF and 300 V, followed by a 30-min incubation at room temperature. Ten ml of fresh culture medium was then added to the suspension of transfected cells, and incubation was performed at 37° C. in a humidified atmosphere with 5% CO$_2$. Cell cultures were monitored for the appearance of cytopathic effect (CPE). At virus breakthrough (full CPE), culture supernatant was harvested by centrifugation (typically at 8 to 10 days after transfection) and was stored at −80° C. for subsequent drug susceptibility determination.

The inhibitory antiviral activity of different compounds was determined in a cell-based HIV-1 replication assay. MT4-LTR-EGFP cells (150,000 cells/ml) were infected with HIV-1 (IIIB or SDM strains Q148R, N155H, or G140S-Q148H; multiplicity of infection [MOI] of 0.0025) in the presence or absence of inhibitor. After 3 days of incubation, the inhibition of HIV replication was quantified by measuring EGFP fluorescence, and expressed as the compound concentration required for 50% inhibition of HIV-1 replication in cell culture (EC$_{50}$). The antiviral activities of the different compounds are reported in Table 4 and expressed as EC$_{50}$ for the inhibition of wild type HIV (IIIB EC$_{50}$) and as fold change in activity against the mutant strains (FC-Q148R, FC-N155H, FC-G140S-Q148H) compared to the activity against wild type HIV.

Example 167

Determination of Inhibitory Activity on Replication of HIV Wild Type in the Presence of Human Serum For the antiviral assay in the presence of 50% human serum, MT-4-LTR-EGFP cells were infected with HIV-1 LAI (IIIB) at a MOI of 0.001 to 0.01 $CCID_{50}$/cell in RPMI1640 medium. Following 1 h of incubation, cells were washed and plated into a 96-well plate containing serial dilutions of test compound in the presence of 10% fetal calf serum or 50% human serum. After 4 days of incubation, the $EC_{50}$ in the presence of 50% human serum ($EC_{50}$/HS) was determined by a cell viability assay using resazurin (as described by Fields, R. D., and M. V. Lancaster (1993) Am. Biotechnol. Lab. 11:48-50).

TABLE 4

| | Biological activity against HIV replication | | | |
|---|---|---|---|---|
| Cpd Nr | IIIB $EC_{50}$ (μM) | FC-Q148R | FC-N155H | FC-G140S-Q148H | $EC_{50}$/HS (μM) |
| 1 | 0.92 | 0.7 | 3.2 | 2.6 | 0.003 |
| 2b | 2.29 | 0.9 | 8.0 | 6.2 | 0.008 |
| 2a | 55.55 | 0.7 | 25.3 | 3.3 | 0.682 |
| 3 | 2.35 | 0.9 | 3.9 | 8.1 | 0.013 |
| 4 | 2.61 | 1.2 | 6.1 | 10.9 | 0.010 |
| 5 | 1.67 | 0.5 | 2.4 | 1.2 | 0.016 |
| 6 | 1.14 | 0.7 | 3.2 | 1.7 | 0.005 |
| 7 | 2.29 | 0.4 | 2.2 | 1.0 | 0.012 |
| 8 | 2.55 | 3.3 | 11.7 | 11.3 | 0.010 |
| 9 | 379.06 | 0.4 | 2.0 | 1.2 | 1.927 |
| 10 | 2.24 | 0.5 | 2.8 | 1.2 | 0.017 |
| 11 | 2.20 | 2.1 | 5.1 | 14.3 | 0.009 |
| 12 | 2.88 | 0.7 | 3.5 | 5.1 | 0.013 |
| 13 | 3.09 | 0.7 | 3.5 | 2.6 | 0.011 |
| 14 | 3.49 | 1.0 | 3.5 | 4.3 | 0.018 |
| 15 | 2.68 | 0.5 | 3.4 | 1.4 | 0.033 |
| 16 | 2.21 | 0.6 | 3.5 | 1.3 | 0.043 |
| 17 | 3.48 | 0.6 | 4.7 | 1.9 | 0.024 |
| 18 | 2.76 | 0.8 | 4.7 | 1.8 | 0.047 |
| 19 | 1.81 | 1.1 | 4.9 | 3.6 | 0.008 |
| 20 | 1.53 | 0.6 | 4.8 | 1.5 | 0.017 |
| 21 | 36.11 | 0.6 | 6.6 | 1.9 | 0.054 |
| 22 | 19.29 | 0.5 | 6.0 | 1.7 | 0.014 |
| 23 | 5.19 | 0.7 | 9.6 | 2.1 | 0.007 |
| 24 | 3.67 | 4.3 | 10.4 | 179.1 | 0.011 |
| 25 | 17.36 | 0.3 | 3.5 | 3.7 | 0.138 |
| 26 | 5.93 | 0.8 | 4.3 | 4.1 | 0.032 |
| 27 | 1.49 | 3.0 | 8.6 | 668.8 | 0.005 |
| 28 | 1.92 | 0.9 | 4.5 | 17.0 | 0.014 |
| 29 | 2.81 | 0.4 | 3.8 | 2.2 | 0.019 |
| 30 | 13.87 | 41.1 | 410.4 | 572.0 | 0.028 |
| 31 | 4.36 | 0.6 | 4.6 | 7.0 | 0.021 |
| 32 | 11.89 | 0.3 | 4.3 | 2.6 | 0.077 |
| 33 | 23.08 | 0.5 | 5.1 | 2.5 | 0.147 |
| 34 | 2.85 | 0.4 | 7.4 | 5.9 | 0.018 |
| 35 | 3.67 | 0.4 | 4.8 | 2.7 | 0.030 |
| 36 | 3.29 | 2.4 | 5.8 | 60.1 | 0.018 |
| 37 | 3.05 | 0.8 | 8.8 | 109.5 | 0.022 |
| 38 | 7.20 | 1.2 | 6.8 | 106.3 | 0.029 |
| 39 | 1207.79 | 1.1 | 4.6 | 2.8 | 3.367 |
| 40 | 796.86 | 0.4 | 6.2 | 3.1 | 1.097 |
| 41 | 993.53 | 0.4 | 6.0 | 2.8 | 1.110 |
| 42 | 1192.42 | 0.5 | 3.3 | 2.6 | 3.171 |
| 43 | 152.14 | 0.5 | 2.0 | 0.8 | 0.101 |
| 44 | 3.01 | 0.7 | 3.9 | 1.3 | 0.006 |
| 45 | 3.07 | 0.8 | 4.3 | 1.6 | 0.006 |
| 46 | 82.56 | 0.3 | 40.8 | 3.6 | 1.492 |
| 47 | 0.98 | 0.7 | 4.4 | 3.2 | 0.004 |
| 48 | 2.53 | 0.5 | 4.7 | 1.3 | 0.004 |
| 49 | 0.59 | 0.5 | 5.3 | 1.6 | 0.008 |
| 50 | 3.00 | 0.3 | 2.8 | 1.2 | 0.011 |
| 51 | 2.54 | 0.4 | 9.6 | 3.4 | 0.013 |
| 52r | 3.40 | 1.2 | 6.8 | 56.9 | 0.029 |
| 53r | 0.99 | 0.4 | 4.9 | 2.0 | 0.003 |
| 54r | 2.04 | 0.4 | 4.4 | 3.1 | 0.007 |

Example 168

Pharmacokinetic Evaluation in the Rat

For determining the pharmacokinetic properties in rat, each HIV integrase inhibitor was dissolved in PEG400/normal saline (70:30 (v/v)) at a nominal concentration of 1 mg/ml and administered (2 ml/kg) to male Sprague-Dawley rats (n=3 per test compound) as an intravenous bolus via a saphenous vein at a dose level of 2 mg/kg. Blood samples were collected via a tail vein at serial time points up to 24 h after dosing. Plasma was obtained by centrifugation and stored at −20° C. prior to analysis. Analysis was performed using liquid chromatography (LC) with tandem mass spectrometric detection (MS/MS) in positive ion mode. Each HIV integrase inhibitor was eluted from a reversed-phase column with a gradient of acetonitrile and water containing 0.1% (v/v) formic acid. At the time of analysis plasma samples (50 p. 1) were thawed and deprotonated with 200 μl of acetonitrile containing 0.1% (v/v) formic acid and centrifuged. Aliquots of the supernatant (100 μl) were diluted with 200 μl of water containing 25% (v/v) methanol and 0.1% (v/v) formic acid and injected via an electrospray interface directly into the Mass Spectrometer. Calibration standards and quality controls were prepared in rat plasma at the same time as the samples and analyzed before and after the samples containing HIV integrase inhibitor. Non-compartmental pharmacokinetic analysis of the plasma concentration-time curves was performed using WinNonLin software to provide estimates of the plasma clearance ($CL_p$), volume of distribution at steady-state ($V_{ss}$) and terminal phase elimination half-life ($t_{1/2}$).

TABLE 5

| Pharmacokinetic evaluation in the rat | | | |
|---|---|---|---|
| Compound number | $CL_p$ (ml/min/kg) | $V_{ss}$ (l/kg) | $t_{1/2}$ (h) |
| 1 | 8 | 0.8 | 4.8 |
| 3 | 6, 8 (n = 2) | 1.2, 4.0 (n = 2) | 4.4, 7.8 (n = 2) |
| 5 | 8 | 1.5 | 4.9 |
| 6 | 5 | 0.7 | 5.5 |
| 7 | 7 | 0.9 | 4.8 |
| 22 | 12 | 0.6 | nd |
| 31 | 13 | 6 | 8.1 |
| 33 | 11 | 1.3 | 4.2 |
| 41 | 7 | 0.7 | 5.4 |
| 44 | 16 | 1.8 | 5.2 |
| 45 | 8 | 0.9 | 4.2 |
| 48 | 20 | 0.7 | 1.4 |
| 52r | 5 | 0.2 | 1.6 |
| 53r | 75 | 2.9 | 1.7 |
| 54r | 40 | 2.2 | 1.5 |

Example 169

Metabolic Stability in Rat and Human Hepatocytes

For determining in vitro metabolic stability, cryopreserved hepatocytes from Sprague Dawley rats and of human subjects (pool of male and female) were obtained from an external supplier (Cellz Direct Inc., Paisly, UK). Tested compounds were dissolved in DMSO and this stock solution was used to spike rat and human hepatocyte cell cultures ($10^6$ cells/ml) at a final concentration of 1 μM (final percentage of DMSO was 0.02% (v/v)). Incubations were performed for up to 60 min at approximately 37° C. and terminated by the addition of two volumes of DMSO. Samples were then centrifuged and aliquots of the supernatant analyzed using liquid chromatography (LC) with electrospray mass spectrometric detection (MS/MS) to monitor the disappearance of parent compound by single reaction monitoring (SRM) and reverse-phase chromotatography with a gradient of acetonitrile and water containing 0.1% (v/v) formic acid. Based on peak area, the percentage of parent compound remaining after 15 and 60 min incubation was calculated and the results, expressed as percentage turnover (TO) relative to time zero controls.

TABLE 6

Metabolic stability in rat and human hepatocytes

| Compound Number | Rat (% TO) | | Human (% TO) | |
|---|---|---|---|---|
| | 15 min | 60 min | 15 min | 60 min |
| 1 | 30 | 42 | 16 | 31 |
| 5 | 15 | 20 | 12 | 38 |
| 6 | 20 | 33 | 23 | 36 |
| 7 | 21 | 31 | 2 | 12 |
| 44 | 48 | 70 | 20 | 43 |
| 48 | 65 | 86 | 38 | 72 |
| 52r | 38 | 76 | 25 | 44 |
| 53r | 60 | 89 | 41 | 84 |
| 54r | 32 | 46 | 16 | 23 |

The invention claimed is:

1. A compound having formula I

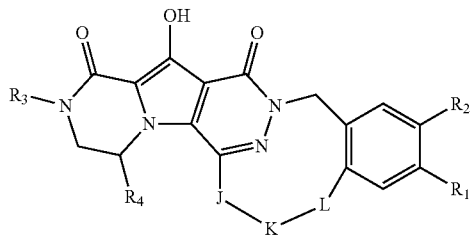

or a stereochemically isomeric form thereof, wherein,
$R_1$ is F or Cl;
$R_2$ is H, F or Cl;
$R_3$ is $C_{1-4}$alkyl, $C_{1-4}$alkoxyC$_{1-4}$alkyl, cyclopropyl or tetrahydrofuranyl;
$R_4$ is hydrogen or methyl;
J is —N($R_5$)—SO$_2$—, —C(=O)—N($R_5$)—, —N($R_5$)—,

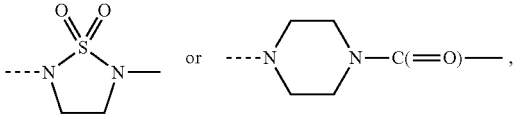

wherein the dashed line denotes the point of attachment to the pyridazinone ring;
K is —(CHR$_6$)$_p$—, *-(CH$_2$)$_q$—CH=CH—CH$_2$— or *-(CH$_2$)$_q$—CH=CH—CH$_2$— wherein * denotes to point of attachment to the J moiety;
L is —O—, —O—CH$_2$-* or —N($R_5$)—C(=O)-* wherein * denotes the point of attachment to the phenyl ring; and,
$R_5$ is hydrogen, $C_{1-4}$alkyl or $C_{3-5}$cycloalkyl;
each $R_6$ independently is hydrogen or $C_{1-3}$alkyl;
p is 3, 4, 5 or 6;
q is 0, 1, 2 or 3;
or a pharmaceutically acceptable salt thereof.

2. A compound according to claim 1 wherein $R_1$ is F and $R_2$ is H.

3. A compound according to claim 2 wherein $R_3$ is ethyl, isopropyl or cyclopropyl.

4. A compound according to claim 3 wherein $R_4$ is methyl.

5. A compound according to claim 4 wherein J is —N($R_5$)—SO$_2$— or

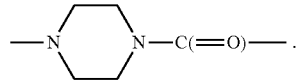

6. A compound according to claim 5 wherein K is —(CHR$_6$)$_p$— wherein p is 3, 4, 5 or 6 and each $R_6$ is independently H or CH$_3$.

7. A compound according to claim 5 wherein K is *-(CH$_2$)$_q$—CH=CH—CH$_2$— wherein q is 2 or 3.

8. A compound according to claim 6 wherein $R_5$ is methyl, ethyl or cyclopropyl.

9. A compound according to claim 8 wherein L is —O— or —O—CH$_2$—.

10. A compound according to claim 9 wherein the -JKL-linking chain is 8 to 11 atoms long.

11. A pharmaceutical composition comprising an anti-virally effective amount of a compound of formula I as defined in claim and a carrier.

12. A pharmaceutical composition according to claim 11, further comprising at least one additional anti-retroviral compound.

13. A compound according to claim 7 wherein R5 is methyl, ethyl or cyclopropyl.

14. A compound according to claim 13 wherein L is —O— or —O—CH$_2$—.

15. A compound according to claim 14 wherein the -JKL-linking chain is 8 to 11 atoms long.

16. A method of treating HIV infection comprising administering to a subject in need thereof a therapeutically effective amount of the composition of claim 11.

17. A method of treating HIV infection comprising administering to a subject in need thereof a therapeutically effective amount of the composition of claim 12.

* * * * *